US008765683B2

(12) United States Patent
Peled et al.

(10) Patent No.: US 8,765,683 B2
(45) Date of Patent: Jul. 1, 2014

(54) T-140 PEPTIDE ANALOGS HAVING CXCR4 SUPER-AGONIST ACTIVITY FOR CANCER THERAPY

(75) Inventors: Amnon Peled, Tel-Aviv (IL); Michal Begin, Jerusalem (IL); Katia Beider, Jerusalem (IL); Michal Abraham, Mevasseret Zion (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 0 days.

(21) Appl. No.: 13/360,751

(22) Filed: Jan. 29, 2012

(65) Prior Publication Data

US 2012/0207748 A1 Aug. 16, 2012

Related U.S. Application Data

(62) Division of application No. 12/520,803, filed as application No. PCT/IL2007/001597 on Dec. 23, 2007, now abandoned.

(60) Provisional application No. 60/876,145, filed on Dec. 21, 2006.

(51) Int. Cl.
*A61K 38/00* (2006.01)
*A61P 35/00* (2006.01)
*A61K 39/00* (2006.01)
*A61K 38/10* (2006.01)

(52) U.S. Cl.
USPC .................. 514/19.2; 424/133.1; 514/21.5

(58) Field of Classification Search
CPC . A61K 2300/00; A61K 38/10; A61K 38/193; A61K 35/28
See application file for complete search history.

(56) References Cited

U.S. PATENT DOCUMENTS

| 4,179,337 | A | 12/1979 | Davis et al. |
|---|---|---|---|
| 4,342,828 | A | 8/1982 | Takaku et al. |
| 5,206,018 | A | 4/1993 | Sehgal et al. |
| 5,250,732 | A | 10/1993 | Kogan et al. |
| 5,492,126 | A | 2/1996 | Hennige et al. |
| 5,595,756 | A | 1/1997 | Bally et al. |
| 6,128,522 | A | 10/2000 | Acker et al. |
| 6,365,583 | B1 | 4/2002 | MacFarland et al. |
| 6,576,875 | B1 | 6/2003 | Kleffner et al. |
| 6,747,036 | B2 * | 6/2004 | Gourdeau et al. ............ 514/274 |
| 6,875,738 | B1 | 4/2005 | Clark-Lewis et al. |
| 6,946,445 | B1 | 9/2005 | Clark-Lewis et al. |
| 7,138,488 | B2 | 11/2006 | Fujii |
| 7,169,750 | B2 | 1/2007 | Bridger et al. |
| 7,291,631 | B2 | 11/2007 | Bridger et al. |
| 7,419,667 | B2 * | 9/2008 | Hatake et al. ............ 424/155.1 |
| 7,423,007 | B2 | 9/2008 | Fujii et al. |
| 7,595,298 | B2 | 9/2009 | Fujii |
| 7,630,750 | B2 | 12/2009 | Liang et al. |
| 8,017,585 | B2 | 9/2011 | Fujii et al. |
| 2002/0156034 | A1 | 10/2002 | Tudan et al. |
| 2002/0159996 | A1 * | 10/2002 | Hariharan et al. ......... 424/142.1 |
| 2002/0516034 | | 10/2002 | Tudan et al. |
| 2004/0116655 | A1 | 6/2004 | Fujii |
| 2004/0197305 | A1 | 10/2004 | Garzino-Demo et al. |
| 2004/0209921 | A1 | 10/2004 | Bridger et al. |
| 2005/0002939 | A1 | 1/2005 | Zlotnik et al. |
| 2005/0043367 | A1 | 2/2005 | Bridger et al. |
| 2006/0008465 | A1 | 1/2006 | Steinaa et al. |
| 2006/0035829 | A1 | 2/2006 | Bridger et al. |
| 2006/0079492 | A1 | 4/2006 | Ahlem et al. |
| 2006/0264378 | A1 | 11/2006 | Fujii et al. |
| 2006/0264605 | A1 | 11/2006 | Fujii |
| 2007/0129760 | A1 | 6/2007 | Demarais et al. |
| 2007/0167459 | A1 | 7/2007 | Habashita et al. |
| 2009/0181897 | A1 | 7/2009 | Fujii et al. |
| 2010/0143334 | A1 | 6/2010 | Peled et al. |
| 2010/0166715 | A1 | 7/2010 | Peled et al. |
| 2010/0184694 | A1 | 7/2010 | Peled et al. |
| 2010/0222256 | A1 | 9/2010 | Fujii |
| 2011/0269686 | A1 | 11/2011 | Fujii et al. |
| 2012/0094907 | A1 | 4/2012 | Abraham et al. |
| 2013/0303460 | A1 | 11/2013 | Peled |

FOREIGN PATENT DOCUMENTS

| CA | 1297007 | 3/1992 |
|---|---|---|
| EP | 0243153 | 10/1987 |
| EP | 0396158 | 11/1990 |
| EP | 0215126 | 7/1991 |
| EP | 0220520 | 9/1991 |
| EP | 0459516 | 12/1991 |
| EP | 0459795 | 12/1991 |
| EP | 0231819 | 4/1992 |
| EP | 0355811 | 12/1993 |
| EP | 0373679 | 6/1994 |
| EP | 0331186 | 8/1994 |
| EP | 0344796 | 9/1994 |

(Continued)

OTHER PUBLICATIONS

Notification of Office Action and Search Report Dated Mar. 6, 2013 From the State Intellectual Property Office of the People's Republic of China Re. Application No. 201080035931.5 and Its Summary in English.

(Continued)

*Primary Examiner* — Marcela M Cordero Garcia

(57) ABSTRACT

The present invention is directed to novel therapeutic uses of T-140 analog peptides and compositions comprising same. Specifically, the invention provides compositions and methods useful in cancer therapy.

6 Claims, 28 Drawing Sheets
(6 of 28 Drawing Sheet(s) Filed in Color)

(56) References Cited

FOREIGN PATENT DOCUMENTS

| EP | 0263490 | 1/1995 |
|---|---|---|
| EP | 0230980 | 3/1996 |
| EP | 0401384 | 3/1996 |
| EP | 0272703 | 10/1997 |
| EP | 0370205 | 7/1998 |
| EP | 0459630 | 8/1998 |
| EP | 0217404 | 1/1999 |
| EP | 0237545 | 8/1999 |
| EP | 0169566 | 7/2000 |
| EP | 0335423 | 3/2003 |
| EP | 1323730 | 7/2003 |
| EP | 0473268 | 10/2003 |
| EP | 1541585 | 6/2005 |
| EP | 2058395 | 5/2009 |
| JP | 2002-506830 | 3/2002 |
| JP | 2002-247843 | 8/2002 |
| WO | WO 2010/146578 | 0/2010 |
| WO | WO 91/07988 | 6/1991 |
| WO | WO 93/15211 | 8/1993 |
| WO | WO 95/10534 | 4/1995 |
| WO | WO 99/47158 | 9/1999 |
| WO | WO 00/06086 | 2/2000 |
| WO | WO 00/09152 | 2/2000 |
| WO | WO 01/38352 | 5/2001 |
| WO | WO 01/64716 | 9/2001 |
| WO | WO 01/85196 | 11/2001 |
| WO | WO 02/20561 | 3/2002 |
| WO | WO 2004/020462 | 3/2004 |
| WO | WO 2004/024178 | 3/2004 |
| WO | WO 2004/087068 | 10/2004 |
| WO | WO 2008/017025 | 2/2008 |
| WO | WO 2008/075369 | 6/2008 |
| WO | WO 2008/075370 | 6/2008 |
| WO | WO 2008/075371 | 6/2008 |
| WO | WO 2010/146584 | 12/2010 |
| WO | WO 2012/095849 | 7/2012 |
| WO | WO 2013/160895 | 10/2013 |

OTHER PUBLICATIONS

Official Action Dated Mar. 5, 2012 From the US Patent and Trademark Office Re. U.S. Appl. No. 12/520,803.
Heredia et al. "Rapamycin Causes Down-Regulation of CCR5 and Accumulation of Anti-HIV Beta-Chemokines: An Approach to Suppress R5 Strains of HIV-1 ", Proc. Natl. Acad. Sci. USA, PNAS, 100(18): 10411-10416, Sep. 2, 2003.
Ulvatne et al. "Short Antibacterial Peptides and Erythromycin Act Synergically Against *Escherichia coli*", Journal of Antimicrobial Chemotherapy, 48: 203-208, 2001.
Translation of Office Action Dated Feb. 1, 2013 From the Japanese Patent Office Re. Application No. 2011-060367.
HIV "Report of the Investigation for Development of HIV Medicaments (Year 2000)", p. 16-21, 2001. Japanese Only.
Office Action Dated Mar. 13, 2013 From the Israel Patent Office Re. Application No. 199468 and Its Translation Into English.
Notice of Allowance Dated Jan. 4, 2013 From the US Patent and Trademark Office Re. U.S. Appl. No. 12/583,746.
Official Action Dated May 4, 2012 From the US Patent and Trademark Office Re. U.S. Appl. No. 12/520,699.
Bork "Powers and Pitfalls in Sequence Analysis: The 70% Hurdle", Genome Research, 10: 398-400, 2000.
Brenner "Errors in Genome Annotation", Trends in Genetics, TIG, 15(4): 132-133, Apr. 1999.
Doerks et al. "Protein Annotation: Detective Work for Function Predicition", Trends in Genetics, 14(6): 248-250, Jun. 1998.
Ngo et al. "Computational Complexity, Protein Structure Prediction, and the Levinthal Paradox", The Protein Folding Problem and Tertiary Structure Prediction, Chap.14: 433-440, 492-495, 1994.
Skolnick et al. "From Genes to Protein Structure and Function: Novel Applications of Computational Approaches in the Genomic Era", Trends in Biotechnology, TIBTECH, 18(1): 34-39, Jan. 2000.

Wells "Additivity of Mutational Effects in Proteins", Biochemistry, 29(37): 8509-8517, Sep. 18, 1990.
Official Action Dated Jun. 25, 2012 From the US Patent and Trademark Office Re. U.S. Appl. No. 12/520,811.
Kucia et al. "Trafficking of Normal Stem Cells and Metastasis of Cancer Stem Cells Involve Similar Mechanisms: Pivotal Role of the SDF-1-CXCR4 Axis", Stem Cells, 23(7): 879-894, Aug. 2005.
Voermans et al. "Migratory Behavior of Leukemic Cells From Acute Myeloid Leukemia Patients", Leukemia, 16(4): 650-657, Apr. 2002.
Official Action Dated Dec. 7, 2012 From the US Patent and Trademark Office Re. U.S. Appl. No. 12/520,699.
Notice of Allowance Dated Dec. 10, 2012 From the US Patent and Trademark Office Re. U.S. Appl. No. 13/178,737.
Supplementary European Search Report and the European Search Opinion Dated Jan. 3, 2013 From the European Patent Office Re. U.S. Appl. No. 10789103.8.
Official Action Dated Sep. 12, 2012 From the US Patent and Trademark Office Re. U.S. Appl. No. 12/520,803.
Advisory Action Before the Filing of an Appeal Brief Dated Nov. 16, 2012 From the US Patent and Trademark Office Re. U.S. Appl. No. 12/520,699.
International Preliminary Report on Patentability Dated Jun. 24, 2009 From the International Bureau of WIPO Re. Application No. PCT/IL2007/001596.
International Preliminary Report on Patentability Dated Jun. 24, 2009 From the International Bureau of WIPO Re. Application No. PCT/IL2007/001598.
International Search Report and the Written Opinion Dated Jun. 4, 2008 From the International Searching Authority Re. Application No. PCT/IL2007/001598.
International Search Report and the Written Opinion Dated Dec. 5, 2008 From the International Searching Authority Re. Application No. PCT/IL2007/001596.
Office Action Dated May 4, 2010 From the Israel Patent Office Re. Application No. 199468.
Office Action Dated May 4, 2010 From the Israel Patent Office Re. Application No. 199469.
Office Action Dated Sep. 4, 2011 From the Israel Patent Office Re. Application No. 199468 and Its Translation Into English.
Office Action Dated Oct. 31, 2011 From the Israel Patent Office Re. Application No. 199469 and Its Translation Into English.
Requisition—Sequence Listing Dated Jan. 5, 2011 From the Canadian Intellectual Property Office Re. Application No. 2,673,719.
Respone Dated Jan. 4, 2012 to Office Action of Sep. 4, 2011 From the Israel Patent Office Re. Application No. 199468 and Its Translation Into English.
Response Dated Oct. 21, 2010 to Office Action of May 4, 2010 From the Israel Patent Office Re. Application No. 199468.
Response Dated Oct. 21, 2010 to Office Action of May 4, 2010 From the Israel Patent Office Re. Application No. 199469.
Response Dated Mar. 22, 2011 to Requisition-Sequence Listing of Jan. 5, 2011 From the Canadian Intellectual Property Office Re. Application No. 2,673,719.
Restriction Official Action Dated Dec. 28, 2011 From the US Patent and Trademark Office Re. U.S. Appl. No. 12/520,803.
AACR "97th Annual Meeting 2006: Publications", AACR, American Association fo Cancer Research, Retreived From the Internet, 2006.
Avniel et al. "Involvement of the CXCL12/CXCR4 Pathway in the Recovery of Skin Following Burns", Journal of Investigative Dermatology, 126(2): 468-476, 2006.
Balkwill "The Significance of Cancer Cell Expression of the Chemokine Receptor CXCR4", Seminars in Cancer Biology, 14: 171-179, 2004.
Broxmeyer et al. "Rapid Mobilization of Murine and Human Hematopoietic Stem and Progenitor Cells With AMD3100, A CXCR4 Antagonist", The Journal of Experimental Medicine, 201(8): 1307-1318, Apr. 18, 2005.
Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, 106(5): 1824-1830, Sep. 1, 2005.

(56) References Cited

OTHER PUBLICATIONS

Dar et al. "Chemokine Receptor CXCR4-Dependent Internalization and Resecretion of Functional Chemokine SDF-1 by Bone Marrow Endothelial and Stromal Cells", Nature Immunology, 6(10): 1038-1046, Oct. 2005.
Darash-Yahana et al. "Role of High Expression Levels of CXCR4 in Tumor Growth, Vascularization, and Metastatis", The FASEB Journal, 18: 1240-1242, 2004.
Flomenberg et al. "The Use of AMD3100 Plus G-CSF for Autologous Hematopoietic Progenitor Cell Mobilization Is Superior to G-CSF Alone", Blood, 106(5): 1867-1874, 2005.
Ghobrial et al. "Molecular Mechanisms Involved in Homing and Migration of Plasma Cells in Response to CXCR4", Blood, XP002629051, 104(11): 1-33, Apr. 12, 2005.
Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.
Kollet et al. "Human CD34 CXCR4—Sorted Cells Harbor Intracellular CXCR4, Which Can Be Functionally Expressed and Provide NOD/SCID Repopulation", Blood, 100(8): 2778-2786, 2002.
Lack et al. "A Pharmacokinetic-Pharmacodynamic Model for the Mobilization of CD34+ Hematopoietic Progenitor Cells by AMD3100", Clinical Pharmacology and Therapeutics, 77(5): 427-436, 2005.
Lapidot et al. "How Do Stem Cells Find Their Way Home?", Blood, 106(6): 1901-1910, 2005.
Lapidot et al. "The Essential Roles of the Chemokine SDF-1 and Its Receptor CXCR4 in Human Stem Cell Homing and Repopulation of Transplanted Immune-Deficient NOD/SCID and NOD/SCID/B2m<Null> Mice", Leukemia, 16(10): 1992-2003, 2002.
Levesque et al. "Disruption of the CXCR4/CXCL12 Chemotactic Interaction During Hematopoietic Stem Cell Mobilization Induced by GCSF or Cyclophosphamide", Journal of Clinical Investigation, 111(2): 187-196, Jan. 2003.
Martin et al. "Chemokines Acting Via CXCR2 and CXCR4 Control the Release of Neutrophils From the Bone Marrow and Their Return Following Senescence", Immunity, 19(4): 583-593, Oct. 2003.
Menu et al. "The Involvement of Stromal Derived Factor 1Alpha in Homing and Progression of Multiple Myeloma in the 5TMM Model", Haematologica/The Hematology Journal, 91(5): 605-612, 2006.
Mueller et al. "Involvement of Chemokine Receptors in Breast Cancer Metastasis", Nature, 410: 50-56, Mar. 2001.
Nagasawa et al. "Molecular Cloning and Structure of A Pre-B-Cell Growth-Stimulating Factor", Proc. Natl. Acad. sci. USA, 91: 2305-2309, Mar. 1994.
Peled et al. "Dependence of Human Stem Cell Engraftment and Repopulation of NOD/SCID Mice on CXCR4", Science, 283(5403): 845-848, 1999.
Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinase/PTEN/AKT/Mammalian Target of Rapamycin Signaling Pathway and Activation of Hypoxia Inducible Factor-1Alpha", The Journal of Biological Chemistry, 280(23): 22473-22481, 2005.
Phillips et al. "The Stromal Derived Factor-1/CXCL12-CXC Chemokine Receptor 4 Biological Axis in Non-Small Cell Lung Cancer Metastasis", 167: 1676-1686, 2003.
Princen et al. "HIV Chemokine Receptor Inhibitors as Novel Anti-HIV Drugs", Cytokine & Growth Factor Reviews, 16(6): 659-677, 2005.
Ratajczak et al. "T140 Enhances G-CSF-Induced Mobilization of Hematopoietic Stem Cells", Experimental Hematology, 31: 154, Abstract #280, 2003.
Rossi et al. "The Biology of Chemokines and Their Receptors", Annual Reviews of Immunology, 18: 217-242, 2000.
Tamamura et al. "A Low-Molecular-Weight Inhibitor Against the Chemokine Receptor CXCR4: A Strong Anti-HIV Paptide T140", Biochemical and Biophysical Research Communications, 253(3): 877-882, 1998.
Tamamura et al. "Enhancement of the T140-Based Pharmacophores Leads to the Development of More Potent and Bio-Stable CXCR4 Antagonists", Organic Biomolecular Chemistry, 1: 3663-3669, 2003.
Tamamura et al. "T140 Analogs as CXCR4 Antagonists Identified as Anti-Metastatic Agents in the Treatment of Breast Cancer", FEBS Letters, 550: 79-83, 2003.
Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.
Tsutsumi et al. "Therapeutic Potential of the Chemokine Receptor CXCR4 Antagonists as Multifunctional Agents", Biopolymers (Peptide Science), XP002629052, 88(2): 279-289, 2006.
Weekes et al. "Stromal Derived Factorl Alpha Mediates Resistance to mTOR Inhibition by the Preservation of Hypoxia Inducible Factor-1Alpha (HIF-1Alpha) Expression", Proceedings of the Annual Meeting of the American Association for Cancer Research, AACR, 47: 553, Abstract #2341, 2006.
Zannettino et al. "Elevated Serum Levels of Stromal-Derived Factor-1Alpha Are Associated With Increased Osteoclast Activity and Osteolytic Bone Disease in Multiple Myeloma Patients", Cancer Research, 65(5): 1700-1709, Mar. 1, 2005.
Zhou et al. "CXCR4 Is a Major Chemokine Receptor on Glioma Cells and Mediates Their Survival", The Journal of Biological Chemistry, 277(51): 49481-49487, Dec. 29, 2002.
Zuluaga et al. "Neutropenia Induced in Outbred Mice by A Simplified Low-Dose Cyclophosphamide Regimen: Characterization and Applicability to Diverse Experimental Models of Infectious Diseases", BMC Infectious Diseases, 6(55): 1-10, Mar. 17, 2006.
Restriction Official Action Dated Mar. 1, 2012 From the US Patent and Trademark Office Re. U.S. Appl. No. 12/520,699.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Translation of Notification of Office Action Dated Mar. 6, 2013 From the State Intellectual Property Office of the People's Republic of China Re. Application No. 201080035931.5.
Translation of Search Report Dated Mar. 6, 2013 From the State Intellectual Property Office of the People's Republic of China Re. Application No. 201080035931.5.
Restriction Official Action Dated Mar. 28, 2012 From the US Patent and Trademark Office Re. U.S. Appl. No. 12/520,811.
Notice of Allowance Dated Feb. 8, 2013 From the US Patent and Trademark Office Re. U.S. Appl. No. 12/520,699.
International Search Report and the Written Opinion Dated Jun. 24, 2009 From the International Searching Authority Re. Application No. PCT/IL2007/001597.
Communication Pursuant to Rules 70(2) and 70a(2) EPC Dated Jan. 22, 2013 From the European Patent Office Re. Application No. 10789103.8.
Official Action Dated Jan. 31, 2013 From the US Patent and Trademark Office Re. U.S. Appl. No. 12/520,811.
Amendment Dated May 15, 2008 After Notice of Allowance of Apr. 14, 2008 From the US Patent and Trademark Office Re. U.S. Appl. No. 10/525,838.
Communication Pursuant to Article 94(3) EPC Dated Oct. 4, 2010 From the European Patent Office Re. Application No. 03791288.8.
Communication Pursuant to Article 94(3) EPC Dated Apr. 9, 2008 From the European Patent Office Re. Application No. 03791288.8.
Communication Pursuant to Article 94(3) EPC Dated Dec. 15, 2008 From the European Patent Office Re. Application No. 03791288.8.
Communication Pursuant to Article 94(3) EPC Dated Sep. 15, 2009 From the European Patent Office Re. Application No. 03791288.8.
Communication Pursuant to Article 96(2) EPC Dated Feb. 6, 2006 From the European Patent Office Re. Application No. 10963414.6.
Communication Pursuant to Article 96(2) EPC Dated Mar. 17, 2005 From the European Patent Office Re. Application No. 10963414.6.

(56) References Cited

OTHER PUBLICATIONS

Communication Pursuant to Article 96(2) EPC Dated Jul. 18, 2006 From the European Patent Office Re. Application No. 10963414.6.
Communication Pursuant to Article 96(2) EPC Dated Jul. 26, 2007 From the European Patent Office Re. Application No. 10963414.6.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Mar. 12, 2012 From the European Patent Office Re. Application No. 10176632.7.
Communication Under Rule 71(3) EPC Dated Apr. 16, 2012 From the European Patent Office Re. Application No. 03791288.8.
European Search Report and the European Search Opinion Dated Feb. 3, 2012 From the European Patent Office Re. Application No. 10176632.7.
International Preliminary Report on Patentability Dated Apr. 19, 2002 From the International Preliminary Examining Authority Re. PCT/JP2001/007668.
International Preliminary Report on Patentability Dated Aug. 19, 2004 From the International Preliminary Examining Authority Re. Application No. PCT/JP2003/010753.
International Preliminary Report on Patentability Dated Dec. 29, 2011 From the International Bureau of WIPO Re. Application No. PCT/IL2010/000466.
International Search Report and the Written Opinion Dated Oct. 15, 2010 From the International Searching Authority Re. Application No. PCT/IL2010/000466.
International Search Report and the Written Opinion Dated May 30, 2012 From the International Searching Authority Re. Application No. PCT/IL2012/050008.
International Search Report Dated Nov. 4, 2003 From the International Searching Authority Re. Application No. PCT/JP2003/010753.
International Search Report Dated Dec. 11, 2001 From the International Searching Authority Re. Application No. PCT/JP2001/007668.
Interview Summary Dated May 3, 2005 From the US Patent and Trademark Office Re. U.S. Appl. No. 10/363,209.
Interview Summary Dated Feb. 21, 2006 From the US Patent and Trademark Office Re. U.S. Appl. No. 10/363,209.
Notice of Allowance Dated Mar. 9, 2006 From the US Patent and Trademark Office Re. U.S. Appl. No. 10/363,209.
Notice of Allowance Dated Apr. 11, 2011 From the US Patent and Trademark Office Re. U.S. Appl. No. 12/172,007.
Notice of Allowance Dated Apr. 14, 2008 From the US Patent and Trademark Office Re. U.S. Appl. No. 10/525,838.
Notice of Allowance Dated May 21, 2009 From the US Patent and Trademark Office Re. U.S. Appl. No. 11/497,225.
Official Action Dated Jul. 1, 2010 From the US Patent and Trademark Office Re. U.S. Appl. No. 12/172,007.
Official Action Dated Nov. 3, 2005 From the US Patent and Trademark Office Re. U.S. Appl. No. 10/363,209.
Official Action Dated Jul. 11, 2007 From the US Patent and Trademark Office Re. U.S. Appl. No. 10/525,838.
Official Action Dated Jun. 15, 2005 From the US Patent and Trademark Office Re. U.S. Appl. No. 10/363,209.
Official Action Dated May 18, 2012 From the US Patent and Trademark Office Re. U.S. Appl. No. 13/178,737.
Official Action Dated Jan. 24, 2011 From the US Patent and Trademark Office Re. U.S. Appl. No. 12/172,007.
Official Action Dated Aug. 28, 2008 From the US Patent and Trademark Office Re. U.S. Appl. No. 11/497,225.
Official Action Dated Dec. 28, 2011 From the US Patent and Trademark Office Re. U.S. Appl. No. 12/583,746.
Requisition by the Examiner Dated Jul. 6, 2012 From the Canadian Intellectual Property Office Re. Application No. 2,421,183.
Requisition by the Examiner Dated Mar. 8, 2011 From the Canadian Intellectual Property Office Re. Application No. 2,421,183.
Requisition by the Examiner Dated Oct. 17, 2011 From the Canadian Intellectual Property Office Re. Application No. 2,537,158.
Requisition by the Examiner Dated May 19, 2011 From the Canadian Intellectual Property Office Re. Application No. 2,421,183.
Requisition by the Examiner Dated Aug. 25, 2009 From the Canadian Intellectual Property Office Re. Application No. 2,421,183.
Requisition by the Examiner Dated May 25, 2010 From the Canadian Intellectual Property Office Re. Application No. 2,537,158.
Response Dated Jul. 1, 2005 to Communication Pursuant to Article 96(2) EPC of Mar. 17, 2005 From the European Patent Office Re. Application No. 10963414.6.
Response Dated Nov. 1, 2010 to Official Action of Jul. 1, 2010 From the US Patent and Trademark Office Re. U.S. Appl. No. 12/172,007.
Response Dated Feb. 3, 2006 to Official Action of Nov. 3, 2005 From the US Patent and Trademark Office Re. U.S. Appl. No. 10/363,209.
Response Dated Jun. 4, 2008 to Restriction Official Action of Apr. 8, 2008 From the US Patent and Trademark Office Re. U.S. Appl. No. 11/497,225.
Response Dated Sep. 7, 2011 to Requisition by the Examiner of Mar. 8, 2011 From the Canadian Intellectual Property Office Re. Application No. 2,421,183.
Response Dated Dec. 8, 2009 to Office Action of Aug. 11, 2009 From the Japanese Patent Office Re. Application No. 2003-301176.
Response Dated Jan. 8, 2008 to Official Action of Jul. 11, 2007 From the US Patent and Trademark Office Re. U.S. Appl. No. 10/525,838.
Response Dated May 9, 2006 to Communication Pursuant to Article 96(2) EPC of Feb. 6, 2006 From the European Patent Office Re. Application No. 10963414.6.
Response Dated Jun. 10, 2009 to Restriction Official Action of Mar. 26, 2009 From the US Patent and Trademark Office Re. U.S. Appl. No. 12/172,007.
Response Dated Oct. 12, 2010 to Communication Pursuant to Article 94(3) EPC of Oct. 4, 2010 From the European Patent Office Re. Application No. 03791288.8.
Response Dated Oct. 14, 2011 to Restriction Official Action of Sep. 14, 2011 From the US Patent and Trademark Office Re. U.S. Appl. No. 12/583,746.
Response Dated Apr. 15, 2009 to Communication Pursuant to Article 94(3) EPC of Dec. 15, 2008 From the European Patent Office Re. Application No. 03791288.8.
Response Dated Oct. 15, 2008 to Communication Pursuant to Article 94(3) EPC of Apr. 9, 2008 From the European Patent Office Re. Application No. 03791288.8.
Response Dated Sep. 15, 2005 to Official Action of Jun. 15, 2005 From the US Patent and Trademark Office Re. U.S. Appl. No. 10/363,209.
Response Dated Nov. 16, 2007 to Communication Pursuant to Article 96(2) EPC of Jul. 26, 2007 From the European Patent Office Re. Application No. 10963414.6.
Response Dated Apr. 18, 2005 to Restriction Official Action of Mar. 18, 2005 From the US Patent and Trademark Office Re. U.S. Appl. No. 10/363,209.
Response Dated Jan. 21, 2010 to Communication Pursuant to Article 94(3) EPC of Sep. 15, 2009 From the European Patent Office Re. Application No. 03791288.8.
Response Dated Mar. 23, 2011 to Official Action of Jan. 24, 2011 From the US Patent and Trademark Office Re. U.S. Appl. No. 12/172,007.
Response Dated Feb. 24, 2010 to Requisition by the Examiner of Aug. 25, 2009 From the Canadian Intellectual Property Office Re. Application No. 2,421,183.
Response Dated May 25, 2007 to Restriction Official Action of Feb. 6, 2007 From the US Patent and Trademark Office Re. U.S. Appl. No. 10/525,838.
Response Dated Nov. 25, 2011 to Requisition by the Examiner of May 25, 2010 From the Canadian Intellectual Property Office Re. Application No. 2,537,158.
Response Dated Jan. 26, 2009 to Official Action of Aug. 28, 2008 From the US Patent and Trademark Office Re. U.S. Appl. No. 11/497,225.
Response Dated Jan. 29, 2007 to Communication Pursuant to Article 96(2) EPC of Jul. 18, 2006 From the European Patent Office Re. Application No. 10963414.6.

(56) References Cited

OTHER PUBLICATIONS

Response Dated Jun. 30, 2010 to Requisition by the Examiner of May 19, 2011 From the Canadian Intellectual Property Office Re. Application No. 2,421,183.
Response Dated Jan. 31, 2011 to Office Action of Oct. 19, 2010 From the Japanese Patent Office Re. Application No. 2003-301176.
Restriction Official Action Dated Feb. 6, 2007 From the US Patent and Trademark Office Re. U.S. Appl. No. 10/525,838.
Restriction Official Action Dated Apr. 8, 2008 From the US Patent and Trademark Office Re. U.S. Appl. No. 11/497,225.
Restriction Official Action Dated Sep. 14, 2011 From the US Patent and Trademark Office Re. U.S. Appl. No. 12/583,746.
Restriction Official Action Dated Feb. 16, 2012 From the US Patent and Trademark Office Re. U.S. Appl. No. 13/178,737.
Restriction Official Action Dated Mar. 18, 2005 From the US Patent and Trademark Office Re. U.S. Appl. No. 10/363,209.
Restriction Official Action Dated Mar. 26, 2009 From the US Patent and Trademark Office Re. U.S. Appl. No. 12/172,007.
Second Amendment Dated Jul. 14, 2008 to Amendment of May 15, 2008 After Notice of Allowance of Apr. 14, 2008 From the US Patent and Trademark Office Re. U.S. Appl. No. 10/525,838.
Supplementary European Search Report Dated Nov. 19, 2004 From the European Patent Office Re. Application No. 01963414.6.
Supplementary Partial European Search Report Dated Nov. 28, 2007 From the European Patent Office Re. Application No. 03791288.8.
Translation of Office Action Dated Aug. 11, 2009 From the Japanese Patent Office Re. Application No. 2003-301176.
Translation of Office Action Dated Oct. 19, 2010 From the Japanese Patent Office Re. Application No. 2003-301176.
Arakaki et al. "T134, A Small-Molecule CXCR4 Inhibitor, Has No Cross-Drug Resistance With AMD3100, A CXCR4 Antagonist With a Different Structure", Journal of Virology, XP002199036, 73(2): 1719-1723, Feb. 1999.
Auerbach et al. "Angiogenesis Assays: Problems, Pitfalls and Potential", Cancer and Metastasis Reviews, 19: 167-172, 2000.
Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, p. 5, Right Col., Last Para.
Fransen et al. "Suppression of Dualtropic Human Immunodeficiency Virus Type 1 by the CXCR4 Antagonist AMD3100 Is Associated With Efficiency of CXCR4 Use and Baseline Virus Composition", Antimicrobial Agents and Chemotherapy, 52(7): 2608-2615, Apr. 28, 2008.
Fujii et al. "Peptide-Lead CXCR4 Antagonists With High Anti-HIV Activity", Current Opinion in Investigational Drugs, 2(9): 1198-1202, 2001.
Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.
Gura "Cancer Models: Systems for Identifying New Drugs Are Often Faulty", Science, 278(5340): 1041-1042, Nov. 7, 1997.
Hatse et al. "CXC-ChemokineReceptor 4 as a Potential New Therapeutic Target for Neuroblastoma and Breast Cancer", International Journal of Cancer, XP001156644, Supplement, 13: 349, Abstract # P 669, Jul. 2002.
Hendrix et al. "Safety, Pharmacokinetics, and Antiviral Activity of AMD3100, A Selective CXCR4 Receptor Inhibitor, in HIV-1 Infection", Journal of Aquired Immune Deficiency Syndromes, JAIDS, 37(2): 1253-1261, Oct. 1, 2004.
Hesselgesser et al. "Neuronal Apoptosis Induced by HIV-1 Gp120 and the Chemokine SDF-1Alpha Is Mediated by the Chemokine Receptor CXCR4", Current Biology, 8: 595-598, Apr. 27, 1998.
Hiramatsu et al. "Synthesis of CXCR4 Antagonists, T140 Derivatives With Improved Biostability, and Their SAR Study", Peptide Science, XP009092185, 203: 213-216, 2002. Abstract, Fig. 1.
Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, p. 58-65, Jul. 1994.
Koshiba et al. "Expression of Stromal Cell-Derived Factor 1 and CXCR4 Ligand Receptor System in Pancreatic Cancer: A Possible Role for Tumor Progression", Clinical Cancer Research, 6(9): 3530-3535, Sep. 2000.
Matthys et al. "AMD3100, A Potent and Specific Antagonist of the Stromal Cell-Derived Factor-1 Chemokine Receptor CXCR4, Inhibits Autoimmune Joint Inflammation in IFN-Gamma Receptor-Deficient Mice", The Journal of Immunology, 167(8): 4686-4692, 2001.
Merck "Clinical Aspects of Cancer", The Merck Manual, Jun. 26, 2007.
Merck "Introduction: Overview of Cancer", The Merck Manual, Jun. 26, 2007.
Merck "Rheumatoid Arthritis (RA)", The Merck Manual, 18th Ed., 2005.
Mori et al. "Involvement of Stromal Cell-Derived Factor 1 and CXCR4 Receptor System in Pancreatic Cancer", Gastroenterology, XP009021758, 122(4/Suppl.1): A490, Abstract # T1608, Apr. 2002.
Nakashima et al. "Anti-Human Immunodeficiency Virus Activity of a Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.
Neidl "Failure Modes in the Discovery Process", Cancer Drug Design and Discovery, Chap.18.2.2: 427-431, 2008.
Omagari et al. "Development of Specific CXCR4 Inhibitors Based on An Anti-HIV Peptide, T140, and Their Structure-Activity Relationships Study", Peptide Science, 2000(37): 129-132, 2001.
Sporn et al. "Chemoprevention of Cancer", Carcinogenesis, 21(3): 525-530, 2000.
Tamamura "Development of Selective Antagonists Against an HIV Second Receptor", Yakugaku Zasshi, 121(11): 781-792, 2001. Abstract in English.
Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.
Tamamura et al. "A Low-Molecular-Weight Inhibitor Against the Chemokine Receptor CXCR4: A Strong Anti-HIV Peptide T140", Biochemic and Biophysical Research Communications, XP002169961, 253(3): 877-882, Jan. 1, 1998. Abstract, Fig. 1.
Tamamura et al. "A Low-Molecular-Weight Inhibitor Against the Chemokine Receptor CXCR4: A Strong Anti-HIV Peptide T140", Biochemical and Biophysical Research Communications, 253(3): 877-882, 1998.
Tamamura et al. "Certification of the Critical Importance of L-3-(2-Naphtyl)Alanine at Position 3 of a Specific CXCR4 Inhibitor, T140, Leads to An Exploratory Performance of Its Downsizing Study", Bioorganic & Medicinal Chemistry, 10: 1417-1426, 2002.
Tamamura et al. "Development of Specific CXCR4 Inhibitors Possessing High Selectivity Indexes as Well as Complete Stability in Serum Based on An Anti-HIV Peptide T140", Bioorganic & Medicinal Chemistry Letters, XP002265743, 11(14): 1897-1902, Jul. 23, 2001. Abstract, Fig.1, p. 1901, r-h Col., Last Sentence Before 'Acknowledgements'.
Tamamura et al. "Downsizing of An HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.
Tamamura et al. "Downsizing of An HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, XP002458598, 6(4): 473-479, Apr. 1998. Abstract, Fig.1.
Tamamura et al. "Effective Lowly Cytotoxic Analogs of An HIV-Cell Fusion Inhibitor, T22 ([Tyr5,12, Lys7]-Polyphemusin II)", Bioorganic & Medicinal Chemistry, 6(2): 231-238, 1998.
Tamamura et al. "Effective Lowly Cytotoxic Analogs of An HIV-Cell Fusion Inhibitor, T22 ([Tyr5,12, Lys7]-Polyphemusin II)", Bioorganic & Medicinal Chemistry, XP002906341, 6(2): 231-238, Jan. 1, 1998. Abstract, Fig. 1.

(56) References Cited

OTHER PUBLICATIONS

Tamamura et al. "Efficient Analogs of An Anti-HIV Peptide, T22 ([Tyr5,12, Lys7]-Polyphemusin II), Having Low Cytotoxicity", Peptide Science—Present and Future, Proceedings of the 1st International Peptide Symposium, XP002973954, 1997: 427-429, Jan. 1, 1999. Abstract, Fig.2.
Tamamura et al. "HIV-Cell Fusion Inhibitors Targeted to the HIV Second Receptor: T22 and Its Downsized Analogs With High Activity", Peptide Science, 1998(35): 49-52, 1999.
Tamamura et al. "Pharmacophore Identification of a Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.
Tamamura et al. "T140 Analogs as CXCR4 Antagonists Identified as Anti-Metastatic Agents in the Treatment of Breast Cancer", FEBS Letters, XP004448372, 550: 79-83, Aug. 28, 2003.
Restriction Official Action Dated Oct. 3, 2013 From the US Patent and Trademark Office Re. U.S. Appl. No. 13/378,061.
Communication Pursuant to Article 94(3) EPC Dated Sep. 11, 2013 From the European Patent Office Re. Application No. 10176632.7.
Requisition by the Examiner Dated Jul. 8, 2013 From the Canadian Intellectual Property Office Re. Application No. 2,421,183.
Requisition—Sequence Listing Dated May 9, 2013 From the Canadian Intellectual Property Office Re. Application No. 2,673,719.
Completion Requirement Letter Dated Oct. 24, 2013 From the Canadian Intellectual Property Office Re. Application No. 2,765,345.
Communication Under Rule 71(3) EPC Dated Oct. 23, 2013 From the European Patent Office Re. Application No. 10789103.8.
Communication Pursuant to Article 94(3) EPC Dated Oct. 4, 2013 From the European Patent Office Re. Application No. 07849623.9.
Abraham et al. "Enhanced Unique Pattern of Hematopoietic Cell Mobilization Induced by the CXCR4 Antagonist 4F-Benzoyl-TN14003", Stem Cells, 25: 2158-2166, 2007.
Requisition by the Examiner Dated Jun. 18, 2013 From the Canadian Intellectual Property Office Re. Application No. 2,673,484.
Communication Pursuant to Article 94(3) EPC Dated May 3, 2013 From the European Patent Office Re. Application No. 10176632.7.
Notice of Allowance Dated Sep. 23, 2013 From the US Patent and Trademark Office Re. U.S. Appl. No. 12/520,811.
International Search Report and the Written Opinion Dated Sep. 2, 2013 From the International Searching Authority Re. Application No. PCT/IL2013/050352.
Requisition by the Examiner Dated Jul. 4, 2013 From the Canadian Intellectual Property Office Re. Application No. 2,537,158.
Burger et al. "CXCR4 Chemokine Receptor Antagonists: Perspectives in SCLC", Expert Opinion on Investigational Drugs, XP002711650, 18(4): 481-490, Apr. 2009.
Burger et al. "Potential of CXCR4 Antagonists for the Treatment of Metastatic Lung Cancer", Expert Reviews of Anticancer Therapy, XP009152669, 1(4): 621-630, Apr. 1, 2011.
Su et al. "Differential Expression of CXCR4 Is Associated With the Metastatic Potential of Human Non-Small Cell Lung Cancer Cells", Clinical Cancer Research, XP055076137, 11(23): 8273-8280, Dec. 1, 2005.
Office Action Dated Jul. 28, 2013 From the Israel Patent Office Re. Application No. 199469 and Its Translation Into English.
Office Action Dated May 20, 2013 From the Israel Patent Office Re. Application No. 216912 and Its Translation Into English.
International Preliminary Report on Patentability Dated Jul. 18, 2013 From the International Bureau of WIPO Re. Application No. PCT/IL2012/050008.
Official Action Dated Jul. 5, 2013 From the US Patent and Trademark Office Re. U.S. Appl. No. 12/520,811.
HIV "Strategic Generation of Anti-AIDS Agents Based on HIV Secondary Receptor Antagonists and Modification of the Agents for Pharmaceutical Use", Report of the Investigation for Development of HIV Medicaments (Year 2000), p. 16-21, 2001. English Translation.
Tamamura et al. "Development of Selective Antagonists Against An HIV Second Receptor", Yakugaku Zasshi, 121(11): 781-792, 2001. English Translation.
Official Action Dated Dec. 17, 2013 From the US Patent and Trademark Office Re. U.S. Appl. No. 13/378,061.
Official Action Dated Sep. 5, 2012 From the US Patent and Trademark Office Re. U.S. Appl. No. 12/520,699.
Official Action Dated Sep. 10, 2012 From the US Patent and Trademark Office Re. U.S. Appl. No. 12/583,746.
Restriction Official Action Dated Feb. 4, 2014 From the US Patent and Trademark Office Re. U.S. Appl. No. 13/978,740.
Communication Pursuant to Article 94(3) EPC Dated Oct. 4, 2013 From the European Patent Office Re. Application No. 07849622.1.
Notification of Office Action and Search Report Dated Nov. 5, 2013 From the State Intellectual Property Office of the People's Republic of China Re. Application No. 201080035931.5 and Its Translation into English.

\* cited by examiner

SEQUENCE LISTING

```
<160> NUMBER OF SEQ ID NOS: 77

<210> SEQ ID NO 1
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 1

Xaa Arg Xaa Cys Tyr Xaa Lys Xaa Pro Tyr Arg Xaa Cys Arg
1               5                   10

<210> SEQ ID NO 2
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
```

-continued

<400> SEQUENCE: 2

Arg Arg Xaa Cys Tyr Xaa Lys Xaa Pro Tyr Arg Xaa Cys Arg
1               5                   10

<210> SEQ ID NO 3
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 3

Arg Arg Xaa Cys Tyr Arg Lys Xaa Pro Tyr Arg Xaa Cys Arg
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 4

Arg Arg Xaa Cys Tyr Xaa Lys Xaa Pro Tyr Arg Xaa Cys Arg
1               5                   10

<210> SEQ ID NO 5
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:

```
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 5

Arg Arg Xaa Cys Tyr Xaa Lys Xaa Pro Tyr Xaa Xaa Cys Arg
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 6

Xaa Arg Xaa Cys Tyr Xaa Lys Xaa Pro Tyr Arg Xaa Cys Arg
1               5                   10

<210> SEQ ID NO 7
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 7
```

```
Xaa Arg Xaa Cys Tyr Arg Lys Xaa Pro Tyr Arg Xaa Cys Arg
1               5                   10
```

<210> SEQ ID NO 8
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline

<400> SEQUENCE: 8

```
Arg Arg Xaa Cys Tyr Arg Lys Xaa Pro Tyr Xaa Xaa Cys Arg
1               5                   10
```

<210> SEQ ID NO 9
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 9

```
Xaa Arg Xaa Cys Tyr Arg Lys Xaa Pro Tyr Xaa Xaa Cys Arg
1               5                   10
```

<210> SEQ ID NO 10
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES -continued

```
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 10

Arg Arg Xaa Cys Tyr Xaa Lys Xaa Pro Tyr Arg Xaa Cys Arg
 1               5                   10

<210> SEQ ID NO 11
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 11

Arg Arg Xaa Cys Tyr Xaa Lys Xaa Pro Tyr Xaa Xaa Cys Arg
 1               5                   10

<210> SEQ ID NO 12
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
```

```
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: AMIDATED

<400> SEQUENCE: 12

Xaa Arg Xaa Cys Tyr Xaa Lys Xaa Pro Tyr Arg Xaa Cys Arg
 1               5                  10

<210> SEQ ID NO 13
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 13

Xaa Arg Xaa Cys Tyr Arg Lys Xaa Pro Tyr Arg Xaa Cys Arg
 1               5                  10

<210> SEQ ID NO 14
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 14

Arg Arg Xaa Cys Tyr Arg Lys Xaa Pro Tyr Xaa Xaa Cys Arg
```

<210> SEQ ID NO 15
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 15

Xaa Arg Xaa Cys Tyr Arg Lys Xaa Pro Tyr Xaa Xaa Cys Arg
1               5                   10

<210> SEQ ID NO 16
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide

```
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 17

Arg Glu Xaa Cys Tyr Arg Lys Xaa Pro Tyr Arg Xaa Cys Arg
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 18

Arg Arg Xaa Cys Tyr Glu Lys Xaa Pro Tyr Arg Xaa Cys Arg
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 19

Arg Arg Xaa Cys Tyr Arg Glu Xaa Pro Tyr Arg Xaa Cys Arg
1               5                   10

<210> SEQ ID NO 20
<211> LENGTH: 14
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline

<400> SEQUENCE: 20

Arg Arg Xaa Cys Tyr Arg Lys Xaa Pro Tyr Arg Xaa Cys Arg
1               5                   10

<210> SEQ ID NO 21
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 21

Arg Arg Xaa Cys Tyr Arg Lys Xaa Pro Tyr Glu Xaa Cys Arg
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
```

<400> SEQUENCE: 22

Arg Arg Xaa Cys Tyr Arg Lys Xaa Pro Tyr Arg Xaa Cys Glu
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 23

Arg Arg Xaa Cys Tyr Xaa Lys Xaa Pro Tyr Arg Xaa Cys Arg
1               5                   10

<210> SEQ ID NO 24
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 24

Arg Arg Xaa Cys Tyr Xaa Lys Xaa Pro Tyr Arg Xaa Cys Arg
1               5                   10

```
<210> SEQ ID NO 25
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 25

Arg Arg Xaa Cys Tyr Xaa Lys Xaa Pro Tyr Arg Xaa Cys Arg
1               5                   10

<210> SEQ ID NO 26
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 26

Xaa Arg Xaa Cys Tyr Xaa Lys Xaa Pro Tyr Arg Xaa Cys Arg
1               5                   10

<210> SEQ ID NO 27
<211> LENGTH: 14
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 27

Arg Arg Xaa Cys Tyr Xaa Lys Xaa Pro Xaa Arg Xaa Cys Arg
1               5                   10

<210> SEQ ID NO 28
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 28

Arg Arg Xaa Cys Tyr Xaa Lys Xaa Pro Tyr Arg Xaa Cys Arg
1               5                   10

<210> SEQ ID NO 29
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED D-glutamic acid
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 29

Xaa Arg Xaa Cys Tyr Xaa Lys Xaa Pro Tyr Arg Xaa Cys Arg
1               5                   10

<210> SEQ ID NO 30
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 30

Arg Arg Xaa Cys Tyr Xaa Lys Xaa Pro Xaa Arg Xaa Cys Arg
1               5                   10

<210> SEQ ID NO 31
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
```

```
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 31

Arg Arg Xaa Cys Tyr Xaa Lys Xaa Pro Tyr Arg Xaa Cys Arg
1               5                   10

<210> SEQ ID NO 32
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 32

Arg Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
```

```
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 33

Xaa Arg Xaa Cys Tyr Xaa Lys Xaa Pro Tyr Arg Xaa Cys Arg
1               5                   10

<210> SEQ ID NO 34
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 34

Xaa Arg Xaa Cys Tyr Xaa Lys Xaa Pro Tyr Arg Xaa Cys Arg
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
```

```
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 35

Xaa Xaa Cys Tyr Xaa Lys Xaa Pro Tyr Arg Xaa Cys Arg
1               5                   10

<210> SEQ ID NO 36
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: amidated

<400> SEQUENCE: 36

Xaa Arg Xaa Cys Tyr Xaa Lys Xaa Pro Tyr Arg Xaa Cys Arg
1               5                   10

<210> SEQ ID NO 37
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 2-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
```

<223> OTHER INFORMATION: c' amidated

<400> SEQUENCE: 37

Xaa Arg Xaa Cys Tyr Xaa Lys Xaa Pro Tyr Arg Xaa Cys Arg
1               5                   10

<210> SEQ ID NO 38
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 5-aminopentanoyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 38

Xaa Xaa Cys Tyr Xaa Lys Xaa Pro Tyr Arg Xaa Cys Arg
1               5                   10

<210> SEQ ID NO 39
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 2-desamino-arginyl
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 39

Xaa Arg Xaa Cys Tyr Xaa Lys Xaa Pro Tyr Arg Xaa Cys Arg

<210> SEQ ID NO 40
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 40

Xaa Xaa Cys Tyr Xaa Lys Xaa Pro Tyr Arg Xaa Cys Arg
1               5                   10

<210> SEQ ID NO 41
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Succinyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 41

Xaa Xaa Cys Tyr Xaa Lys Xaa Pro Tyr Arg Xaa Cys Arg
1               5                   10

<210> SEQ ID NO 42
<211> LENGTH: 13

```
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Glutaryl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 42

Xaa Xaa Cys Tyr Xaa Lys Xaa Pro Tyr Arg Xaa Cys Arg
1               5                   10

<210> SEQ ID NO 43
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: DesaminoTMG
<220> FEATURE:
<221> NAME/KEY: MOD_RES
<222> LOCATION: (2)..(2)
<223> OTHER INFORMATION: APA (5-aminopentanoyl)
<220> FEATURE:
<221> NAME/KEY: MOD_RES
<222> LOCATION: (4)..(4)
<223> OTHER INFORMATION: 3-((2-naphthyl) alanine
<220> FEATURE:
<221> NAME/KEY: MOD_RES
<222> LOCATION: (7)..(7)
<223> OTHER INFORMATION: citrulline
<220> FEATURE:
<221> NAME/KEY: MOD_RES
<222> LOCATION: (9)..(9)
<223> OTHER INFORMATION: D-glutamic acid
<220> FEATURE:
<221> NAME/KEY: MOD_RES
<222> LOCATION: (13)..(13)
<223> OTHER INFORMATION: citrulline
<220> FEATURE:
<221> NAME/KEY: MOD_RES
<222> LOCATION: (15)..(15)
<223> OTHER INFORMATION: c' amidated

<400> SEQUENCE: 43

Xaa Xaa Arg Xaa Cys Tyr Xaa Lys Xaa Pro Tyr Arg Xaa Cys Arg
1               5                   10                  15

<210> SEQ ID NO 44
<211> LENGTH: 13
<212> TYPE: PRT
```

```
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: R-CH2-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 44

Arg Xaa Cys Tyr Xaa Lys Xaa Pro Tyr Arg Xaa Cys Arg
1               5                   10

<210> SEQ ID NO 45
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' deaminated peptide
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 45

Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 46

Xaa Arg Xaa Cys Tyr Xaa Lys Xaa Pro Tyr Arg Xaa Cys Arg
1               5                   10

<210> SEQ ID NO 47
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 47

Xaa Arg Xaa Cys Tyr Xaa Lys Xaa Pro Tyr Arg Xaa Cys Arg
1               5                   10

<210> SEQ ID NO 48
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 48

Xaa Arg Xaa Cys Tyr Arg Lys Xaa Pro Tyr Arg Xaa Cys Arg
1               5                   10

<210> SEQ ID NO 49
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 49

Arg Arg Xaa Cys Tyr Xaa Arg Xaa Pro Tyr Arg Xaa Cys Arg
1               5                   10

<210> SEQ ID NO 50
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated
```

<400> SEQUENCE: 50

Arg Arg Xaa Cys Tyr Xaa Arg Xaa Pro Tyr Arg Xaa Cys Arg
1               5                   10

<210> SEQ ID NO 51
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 51

Arg Arg Xaa Cys Tyr Xaa Lys Xaa Pro Tyr Arg Xaa Cys Arg
1               5                   10

<210> SEQ ID NO 52
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 52

Arg Arg Xaa Cys Tyr Arg Lys Xaa Pro Tyr Arg Xaa Cys Arg
1               5                   10

<210> SEQ ID NO 53
<211> LENGTH: 14

```
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: misc_feature
<222> LOCATION: (14)..(14)
<223> OTHER INFORMATION: derivatization by a NH-methyl group

<400> SEQUENCE: 53

Xaa Arg Xaa Cys Tyr Xaa Lys Xaa Pro Tyr Arg Xaa Cys Arg
1               5                   10

<210> SEQ ID NO 54
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: misc_feature
<222> LOCATION: (14)..(14)
<223> OTHER INFORMATION: derivatization by a NH-ethyl group

<400> SEQUENCE: 54

Xaa Arg Xaa Cys Tyr Xaa Lys Xaa Pro Tyr Arg Xaa Cys Arg
1               5                   10

<210> SEQ ID NO 55
<211> LENGTH: 14
<212> TYPE: PRT
<213> ORGANISM: Artificial sequence
<220> FEATURE:
<223> OTHER INFORMATION: Synthetic peptide
<220> FEATURE:
```

<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: misc_feature
<222> LOCATION: (14)..(14)
<223> OTHER INFORMATION: derivatization by NH-isopropyl

<400> SEQUENCE: 55

Xaa Arg Xaa Cys Tyr Xaa Lys Xaa Pro Tyr Arg Xaa Cys Arg
1               5                   10

<210> SEQ ID NO 56
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: misc_feature
<222> LOCATION: (14)..(14)
<223> OTHER INFORMATION: derivatization with a tyramine residue

<400> SEQUENCE: 56

Xaa Arg Xaa Cys Tyr Xaa Lys Xaa Pro Tyr Arg Xaa Cys Arg
1               5                   10

<210> SEQ ID NO 57
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES

```
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 57

Ala Arg Xaa Cys Tyr Arg Lys Xaa Pro Tyr Arg Xaa Cys Arg
1               5                   10

<210> SEQ ID NO 58
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 58

Arg Arg Xaa Cys Tyr Ala Lys Xaa Pro Tyr Arg Xaa Cys Arg
1               5                   10

<210> SEQ ID NO 59
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 59

Arg Arg Xaa Cys Tyr Arg Ala Xaa Pro Tyr Arg Xaa Cys Arg
1               5                   10

<210> SEQ ID NO 60
<211> LENGTH: 14
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-alanine
<220> FEATURE:
<221> NAME/KEY: MOD_RES
<222> LOCATION: (12)..(12)
<223> OTHER INFORMATION: citrulline

<400> SEQUENCE: 60

Arg Arg Xaa Cys Tyr Arg Lys Xaa Pro Tyr Arg Xaa Cys Arg
1               5                   10

<210> SEQ ID NO 61
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 61

Arg Arg Xaa Cys Tyr Arg Lys Xaa Ala Tyr Arg Xaa Cys Arg
1               5                   10

<210> SEQ ID NO 62
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 62
```

Arg Arg Xaa Cys Tyr Arg Lys Xaa Pro Ala Arg Xaa Cys Arg
1               5                   10

<210> SEQ ID NO 63
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 63

Arg Arg Xaa Cys Tyr Arg Lys Xaa Pro Tyr Ala Xaa Cys Arg
1               5                   10

<210> SEQ ID NO 64
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 64

Xaa Arg Xaa Cys Tyr Arg Lys Xaa Pro Tyr Arg Xaa Cys Arg
1               5                   10

<210> SEQ ID NO 65
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)

```
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (7)..(7)
<223> OTHER INFORMATION: citrulline
<220> FEATURE:
<221> NAME/KEY: MOD_RES
<222> LOCATION: (8)..(8)
<223> OTHER INFORMATION: D-lysine
```

```
<220> FEATURE:
<221> NAME/KEY: MOD_RES
<222> LOCATION: (12)..(12)
<223> OTHER INFORMATION: citrulline

<400> SEQUENCE: 67

Arg Arg Xaa Cys Tyr Arg Xaa Xaa Pro Tyr Arg Xaa Cys Arg
1               5                   10

<210> SEQ ID NO 68
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 68

Arg Arg Xaa Cys Tyr Xaa Lys Xaa Pro Tyr Arg Xaa Cys Arg
1               5                   10

<210> SEQ ID NO 69
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 69

Arg Arg Xaa Cys Tyr Arg Lys Xaa Pro Tyr Arg Xaa Cys Arg
1               5                   10

<210> SEQ ID NO 70
<211> LENGTH: 14
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 70

Arg Arg Xaa Cys Tyr Xaa Lys Xaa Pro Tyr Arg Xaa Cys Arg
1               5                   10

<210> SEQ ID NO 71
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 71

Arg Arg Xaa Cys Tyr Arg Lys Xaa Pro Tyr Arg Xaa Cys Arg
1               5                   10

<210> SEQ ID NO 72
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: misc_feature
<222> LOCATION: (1)..(1)
<223> OTHER INFORMATION: N' deaminated peptide
<220> FEATURE:
<221> NAME/KEY: MOD_RES
<222> LOCATION: (3)..(3)
<223> OTHER INFORMATION: 3-((2-naphthyl) alanine
<220> FEATURE:
```

```
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' Amidated

<400> SEQUENCE: 72

Xaa Arg Xaa Cys Tyr Arg Lys Xaa Pro Tyr Arg Xaa Cys Arg
1               5                   10

<210> SEQ ID NO 73
<211> LENGTH: 14
<212> TYPE: PRT
<213> ORGANISM: Artificial sequence
<220> FEATURE:
<223> OTHER INFORMATION: T-140 peptide analogs and derivatives formula
<220> FEATURE:
<221> NAME/KEY: misc_feature
<222> LOCATION: (1)..(1)
<223> OTHER INFORMATION: Xaa can be  Arg, Lys, Ornithine, Citrulline,
      Ala or Glu which may be derivatized at the N-terminal, or an
      absent amino acid residue in which case the peptide will be
      deaminated.
<220> FEATURE:
<221> NAME/KEY: misc_feature
<222> LOCATION: (1)..(14)
<223> OTHER INFORMATION: L-amino acid or D-amino acid
<220> FEATURE:
<221> NAME/KEY: misc_feature
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) represent an absent
      residue, Xaa is Arg or Glu which may be derivatized at the
      N-terminal
<220> FEATURE:
<221> NAME/KEY: misc_feature
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: misc_feature
<222> LOCATION: (6)..(6)
<223> OTHER INFORMATION: Xaa is Arg, Lys, ornithine, citrulline, Ala or
      Glu.
<220> FEATURE:
<221> NAME/KEY: misc_feature
<222> LOCATION: (7)..(7)
<223> OTHER INFORMATION: Xaa is Arg, Lys, ornithine, citrulline, Ala or
      Glu.
<220> FEATURE:
<221> NAME/KEY: misc_feature
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: misc_feature
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: misc_feature
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: misc_feature
```

```
<222> LOCATION: (11)..(11)
<223> OTHER INFORMATION: Xaa is Arg, Lys, ornithine, citrulline, Ala or
      Glu.
<220> FEATURE:
<221> NAME/KEY: misc_feature
<222> LOCATION: (12)..(12)
<223> OTHER INFORMATION: Xaa is Arg, Lys, citrulline or Glu.
<220> FEATURE:
<221> NAME/KEY: misc_feature
<222> LOCATION: (14)..(14)
<223> OTHER INFORMATION: Xaa is Arg, Glu, Lys or citrulline which may be
      derivatized at the C-terminal.

<400> SEQUENCE: 73

Xaa Xaa Xaa Cys Tyr Xaa Xaa Xaa Xaa Xaa Xaa Xaa Cys Xaa
1               5                   10

<210> SEQ ID NO 74
<211> LENGTH: 14
<212> TYPE: PRT
<213> ORGANISM: Artificial sequence
<220> FEATURE:
<223> OTHER INFORMATION: T-140 peptide analogs and derivatives formula
<220> FEATURE:
<221> NAME/KEY: misc_feature
<222> LOCATION: (1)..(1)
<223> OTHER INFORMATION: Xaa is Arg, Ala or Citrulline
<220> FEATURE:
<221> NAME/KEY: misc_feature
<222> LOCATION: (3)..(3)
<223> OTHER INFORMATION: Xaa is Trp or naphtylalanine
<220> FEATURE:
<221> NAME/KEY: misc_feature
<222> LOCATION: (6)..(6)
<223> OTHER INFORMATION: Xaa is Arg, Ala or Citrulline
<220> FEATURE:
<221> NAME/KEY: misc_feature
<222> LOCATION: (7)..(7)
<223> OTHER INFORMATION: Xaa is Lys, Ala or Citrulline
<220> FEATURE:
<221> NAME/KEY: misc_feature
<222> LOCATION: (8)..(9)
<223> OTHER INFORMATION: These positions represent a dipeptide selected
      from: D-lysyl-proline, D-alanyl-proline, D-lysyl-alanine and
      D-citrullyl-proline
<220> FEATURE:
<221> NAME/KEY: misc_feature
<222> LOCATION: (10)..(10)
<223> OTHER INFORMATION: Xaa is Tyr or Ala
<220> FEATURE:
<221> NAME/KEY: misc_feature
<222> LOCATION: (11)..(11)
<223> OTHER INFORMATION: Xaa is Arg, Ala or Citrulline
<220> FEATURE:
<221> NAME/KEY: misc_feature
<222> LOCATION: (12)..(12)
<223> OTHER INFORMATION: Xaa is Citrulline

<400> SEQUENCE: 74

Xaa Arg Xaa Cys Tyr Xaa Xaa Xaa Xaa Xaa Xaa Xaa Cys Arg
1               5                   10

<210> SEQ ID NO 75
<211> LENGTH: 13
<212> TYPE: PRT
<213> ORGANISM: Artificial sequence
<220> FEATURE:
<223> OTHER INFORMATION: T-140 peptide analogs and derivatives formula
<220> FEATURE:
<221> NAME/KEY: misc_feature
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
```

```
<221> NAME/KEY: misc_feature
<222> LOCATION: (3)..(3)
<223> OTHER INFORMATION: Any aromatic amino acid
<220> FEATURE:
<221> NAME/KEY: misc_feature
<222> LOCATION: (6)..(7)
<223> OTHER INFORMATION: Each position independently represents Arg,
      Lys, Ala, ornithine or citrulline
<220> FEATURE:
<221> NAME/KEY: misc_feature
<222> LOCATION: (8)..(8)
<223> OTHER INFORMATION: D-citrulline, D-alanine, citrulline or alanine
<220> FEATURE:
<221> NAME/KEY: misc_feature
<222> LOCATION: (9)..(9)
<223> OTHER INFORMATION: Tyr, Phe, Ala, naphthylalanine or citrulline
<220> FEATURE:
<221> NAME/KEY: misc_feature
<222> LOCATION: (10)..(10)
<223> OTHER INFORMATION: Arg, Lys, Ala, ornithine or citrulline
<220> FEATURE:
<221> NAME/KEY: misc_feature
<222> LOCATION: (11)..(11)
<223> OTHER INFORMATION: citrulline
<220> FEATURE:
<221> NAME/KEY: misc_feature
<222> LOCATION: (13)..(13)
<223> OTHER INFORMATION: Lys or Arg; a carboxyl group may be amidated

<400> SEQUENCE: 75

Xaa Arg Xaa Cys Tyr Xaa Xaa Xaa Xaa Xaa Xaa Cys Xaa
1               5                   10

<210> SEQ ID NO 76
<211> LENGTH: 14
<212> TYPE: PRT
<213> ORGANISM: Artificial sequence
<220> FEATURE:
<223> OTHER INFORMATION: T-140 peptide analogs and derivatives formula
<220> FEATURE:
<221> NAME/KEY: misc_feature
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: misc_feature
<222> LOCATION: (1)..(14)
<223> OTHER INFORMATION: this sequence is structured with the proviso
      that either of the amino acid residues at positions 1, 6, 7, 10 or
      11 is Ala or citrulline
<220> FEATURE:
<221> NAME/KEY: misc_feature
<222> LOCATION: (3)..(3)
<223> OTHER INFORMATION: Any aromatic amino acid
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: misc_feature
<222> LOCATION: (6)..(7)
<223> OTHER INFORMATION: Each position independently represents Arg,
      Lys, Ala, ornithine or citrulline
<220> FEATURE:
<221> NAME/KEY: misc_feature
<222> LOCATION: (8)..(9)
<223> OTHER INFORMATION: D-orn-pro, pro-D-orn, D-lys-pro, pro-D-lys,
      D-arg-pro, pro-D-arg, D-cit-pro, D-cit-ala, D-ala-cit, pro-D-cit,
      gly-orn, orn-gly, gly-lys, lys-gly, gly-arg, arg-gly, gly-cit,
      cit-gly, D-ala-pro or D-lys-ala
<220> FEATURE:
<221> NAME/KEY: misc_feature
<222> LOCATION: (10)..(10)
<223> OTHER INFORMATION: Tyr, Phe, Ala, naphthylalanine or citrulline
<220> FEATURE:
```

```
<221> NAME/KEY: misc_feature
<222> LOCATION: (11)..(11)
<223> OTHER INFORMATION: Arg, Lys, Ala, ornithine or citrulline
<220> FEATURE:
<221> NAME/KEY: misc_feature
<222> LOCATION: (12)..(12)
<223> OTHER INFORMATION: Citrulline
<220> FEATURE:
<221> NAME/KEY: misc_feature
<222> LOCATION: (14)..(14)
<223> OTHER INFORMATION: Lys or Arg; a carboxyl group may be amidated or
      esterified

<400> SEQUENCE: 76

Xaa Arg Xaa Cys Tyr Xaa Xaa Xaa Xaa Xaa Xaa Xaa Cys Xaa
1               5                   10

<210> SEQ ID NO 77
<211> LENGTH: 18
<212> TYPE: PRT
<213> ORGANISM: Artificial sequence
<220> FEATURE:
<223> OTHER INFORMATION: T-140 peptide analogs and derivatives formula
<220> FEATURE:
<221> NAME/KEY: misc_feature
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: misc_feature
<222> LOCATION: (1)..(18)
<223> OTHER INFORMATION: this sequence is structured with the proviso
      that either of the amino acid residues at positions 1, 6, 7, 14
      and 15 is Ala or citrulline
<220> FEATURE:
<221> NAME/KEY: misc_feature
<222> LOCATION: (3)..(3)
<223> OTHER INFORMATION: Any aromatic amino acid
<220> FEATURE:
<221> NAME/KEY: DISULFID
<222> LOCATION: (4)..(17)
<223> OTHER INFORMATION: Cys at 4-position and Cys at 17-position may
      form a disulfid bond.
<220> FEATURE:
<221> NAME/KEY: misc_feature
<222> LOCATION: (6)..(7)
<223> OTHER INFORMATION: Each position independently represents Arg,
      Lys, Ala, ornithine or citrulline
<220> FEATURE:
<221> NAME/KEY: misc_feature
<222> LOCATION: (8)..(8)
<223> OTHER INFORMATION: Ala, Val, Leu, Ile, Ser, Cys or Met
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: misc_feature
<222> LOCATION: (9)..(9)
<223> OTHER INFORMATION: Any aromatic amino acid
<220> FEATURE:
<221> NAME/KEY: misc_feature
<222> LOCATION: (10)..(10)
<223> OTHER INFORMATION: Arg, Lys, Ala, ornithine or citrulline
<220> FEATURE:
<221> NAME/KEY: misc_feature
<222> LOCATION: (12)..(12)
<223> OTHER INFORMATION: Tyr, Phe, Trp, Ala, Val, Leu, Ile, Ser, Cys or
      Met
<220> FEATURE:
<221> NAME/KEY: misc_feature
<222> LOCATION: (13)..(13)
<223> OTHER INFORMATION: Ala, Val, Leu, Ile, Ser, Cys or Met
<220> FEATURE:
<221> NAME/KEY: misc_feature
```

```
<222> LOCATION: (14)..(14)
<223> OTHER INFORMATION: Tyr, Phe, Ala, naphthylalanine or citrulline
<220> FEATURE:
<221> NAME/KEY: misc_feature
<222> LOCATION: (15)..(15)
<223> OTHER INFORMATION: Arg, Lys, Ala, ornithine or citrulline
<220> FEATURE:
<221> NAME/KEY: misc_feature
<222> LOCATION: (16)..(16)
<223> OTHER INFORMATION: citrulline
<220> FEATURE:
<221> NAME/KEY: misc_feature
<222> LOCATION: (18)..(18)
<223> OTHER INFORMATION: Lys or Arg; a carboxyl group may be amidated or
      esterified

<400> SEQUENCE: 77

Xaa Arg Xaa Cys Tyr Xaa Xaa Xaa Xaa Xaa Gly Xaa Xaa Xaa Xaa Xaa
1               5                   10                  15

Cys Xaa
```

T-140 PEPTIDE ANALOGS HAVING CXCR4 SUPER-AGONIST ACTIVITY FOR CANCER THERAPY

RELATED APPLICATION DATA

This application is divisional of U.S. patent application Ser. No. 12/520,803 filed on Oct. 26, 2009, which is a National Phase of PCT Patent Application No. PCT/IL2007/001597 filed on Dec. 23, 2007, which claims the benefit of priority of U.S. Provisional Patent Application No. 60/876,145 filed on Dec. 21, 2006. The contents of all of the above applications are incorporated by reference as if fully set forth herein.

FIELD OF THE INVENTION

The present invention is directed to compositions comprising T-140 peptide analogs having CXCR4 super-agonist activity and to novel therapeutic uses thereof in cancer therapy.

BACKGROUND OF THE INVENTION

Chemokines, a family of small pro-inflammatory cytokines, and their receptors, regulate a variety of immune responses to infection, inflammation and tissue repair. Chemokines are divided between two major families on the basis of relative position of cysteine residues in the mature protein (C-C and C-X-C). Primarily, they are responsible for the directional migration, or chemotaxis, of lymphocytes to specific lymphoid tissues, and the recruitment of leukocytes to the sites of infection or tissue damage. In addition to their chemotactic function, chemokines are implicated in other biological events including embryogenesis, lymphopoiesis, vascularization, and HIV pathogenesis. More recently, it has been established that cancer cells exploit signaling through chemokine receptors for several key steps involved in initiation and progression of primary and metastatic cancer. Different types of cancers express different CC and CXC chemokine receptors. There is one chemokine receptor, however, that appears to be expressed by the majority of cancer types, namely, CXCR4.

The CXCR4/CXCL12 Axis

The chemokine receptor CXCR4 is a G-protein coupled receptor that is expressed in a wide assortment of normal tissues, and plays a fundamental role in fetal development, mobilization of hematopoietic stem cells and trafficking of naive lymphocytes (Rossi and Zlotnik, 2000). Besides normal tissues, CXCR4 appears to be expressed by at least 23 different epithelial, mesenchymal and hematopoietic cancers, including prostate cancer, and acute and chronic myeloid leukemias (Balkwill, 2004). The chemokine CXCL12 (also known as stromal-derived factor-1, or SDF-1) is CXCR4's only natural ligand. CXCL12 is expressed constitutively in a variety of tissues, including lung, liver, bone marrow and lymph nodes. These organs with highest expression of CXCL12 correlate with common metastatic destinations in many cancers. The chemokine receptor, CXCR4, and its ligand, CXCL12, appear to be an important chemokine axis regulating tumor growth and metastasis (Nagasawa et al., 1994; Muller et al., 2001; Phillips et al., 2003).

Binding of CXCL12 to CXCR4 activates a variety of intracellular signal transduction pathways and effector molecules that regulate cell chemotaxis, adhesion, survival, and proliferation. There are a number of key molecules that mediate signaling through CXCR4, and some of them will be described below.

CXCL12 and CXCR4 stimulate the phosphatidyl-inositol-3-kinase pathway that subsequently activates the protein kinase, Akt. Activated Akt phosphorylates a variety of intracellular targets, functioning to inhibit apoptosis and prolonging survival in different types of cancer cells. Beyond cell survival, Akt has also been implicated in effects of CXCR4 on migration of cells toward CXCL12 and their proliferation.

The mitogen-activated protein (MAP) kinase pathway is another signal transduction pathway regulated by CXCR4. Following stimulation with CXCL12, CXCR4 activates the kinase MEK, which in turn activates ERK1/2 MAP kinases. Activated ERK1/2 kinases phosphorylate transcription factors such as Elk-1; this process increases expression of genes that promote survival and proliferation of cancer cells.

CXCR4 also appears to regulate angiogenesis, the process that is important for both normal physiology and growth of tumors. Mice lacking CXCR4 or CXCL12 have defective formation of blood vessels in the gastrointestinal tract. Pro-angiogenic effect of CXCR4 signaling may be mediated through up-regulation of vascular-endothelial growth factor (VEGF). Thus, another potential function of CXCR4 signaling in tumor development is promotion of blood vessel production.

The CXCR4/CXCL12 Axis in Hematopoietic Stem Cell Mobilization

All mature blood cells are derived from hematopoietic stem cells (HSC) through intermediates that are termed hematopoietic progenitor cells (HPCs). Hematopoietic cells at various stages of differentiation are localized within the bone marrow (BM), their main site of production. Their mobilization between BM and blood is a physiological process, but under steady-state conditions HPCs and HSCs circulate in the blood at frequencies too low to allow for efficient collection of numbers sufficient to transplantation. Recently, the use of peripheral blood as source of HSCs for transplantations has replaced bone marrow as the preferred source of hematopoietic rescue. Stem cell frequencies in blood are considerably increased both in responses to various growth factors and during the recovery phase following myelosuppressive chemotherapy. Increased number of hematopoietic cells in the blood and amelioration of their mobilization ability will improve the efficiency of transplantation and will shorten the time of cytopenia and engraftment.

Granulocyte Colony-stimulating Factor (G-CSF)-mobilized peripheral-blood mononuclear cells are routinely used as a source of hematopoietic stem cells for transplantation. However, this mobilization results in broad inter-individual variations in circulating progenitor cell numbers. Thus, optimal methods to mobilize and collect peripheral-blood progenitor cells for hematopoietic rescue still need to be found.

Over recent years it has become apparent that the interaction between CXCL12 and its receptor, CXCR4, plays pivotal role in mobilization and engraftment of hematopoietic cells (Kollet et al., 2002; Lapidot et al., 2002; Levesque et al., 2003; Peled et al., 1999; Lapidot et al., 2005; Dar et al., 2005). The CXCR4 receptor is widely expressed on many cell types including HSCs and HPCs and the interaction with its ligand seems to be involved in their chemotaxis, homing and survival. The CXCL12/CXCR4 axis was found to be involved in the retention of hematopoietic cells within the bone marrow microenvironment (Kim et al., 1998) and consequently, it was suggested that antagonizing the interactions of marrow-produced CXCL12 with CXCR4 expressed on HSCs might be an effective HSC mobilizing strategy.

CXCR4 Modulators and T-140 Analogs

Various uses of chemokine receptor modulators, including CXCR4 agonists and antagonists, have been described in the art (Princen et al., 2005; Tamamura et al., 2005). For example, the bicyclam drug termed AMD3100, originally discovered as an anti-HIV compound, specifically interacts with CXCR4 in an antagonistic manner. Blocking CXCR4 receptor with AMD3100 results in the mobilization of hematopoietic progenitor cells; when combining AMD3100 with G-CSF, additive effects were detected (Flomenberg et al., 2005; Broxmeyer et al., 2005). AMD3100 is currently undergoing clinical trials to evaluate its ability to increase stem cells available for transplant (Lack et al., 2005). U.S. Pat. No. 6,365,583 discloses a method to treat a subject who would be benefited by elevation of white blood cell count which method comprises administering to said subject a cyclic polyamine such as AMD3100. Martin et al. (2003) show that the mobilization of neutrophils from the bone marrow by the CXCR2-chemokine, KC, was enhanced by AMD3100, examined 60 minutes after administration to normal BALB/c mice.

U.S. Patent Application Publication No. 2004/0209921 discloses heterocyclic compounds that bind to chemokine receptors, including CXCR4 and CCR5, which may possess protective effects against infection of target cells by a human immunodeficiency virus (HIV). Other potential uses for these compounds suggested by '921 are enhancing the population of progenitor and/or stem cells, stimulating the production of white blood cells, and/or effecting regeneration of cardiac tissue.

U.S. Pat. No. 6,946,445 discloses CXCR4 antagonists comprising the sequence KGVSLSYR. The antagonists disclosed by the '445 patent are suggested to be potentially useful for reducing interferon gamma production by T-cells, treatment of an autoimmune disease, treatment of multiple sclerosis, treatment of other neurological diseases, treatment of cancer, and regulation of angiogenesis. U.S. Pat. No. 6,875,738 discloses methods for treating a solid tumor in a mammal and for inhibiting angiogenesis in a mammal using these antagonists.

U.S. Patent Application Publication No. 2005/0002939 discloses a method of treating ovarian cancer in a mammal, the method comprising administering to the mammal a therapeutically effective dose of a CXCR4 inhibitor. The '939 application suggests that an anti-CXCR4 antibody may impact the survival or growth of a CXCR4-expressing tumor derived from a bladder tumor cell line in a mouse model.

T-140 is a 14-residue synthetic peptide developed as a specific CXCR4 antagonist that suppresses HIV-1 (X4-HIV-1) entry to T cells through specific binding to CXCR4 (Tamamura et al., 1998). Subsequently, peptide analogs of T-140 were developed as specific CXCR4 antagonist peptides with inhibitory activity at nanomolar levels (see Tamamura et al., 2003, WO 2002/020561 and WO 2004/020462).

WO 2002/020561 discloses novel peptide analogs and derivatives of T-140. The '561 publication demonstrates that the claimed peptides are potent CXCR4 inhibitors, manifesting high anti-HIV virus activity and low cytotoxicity.

WO 2004/020462 discloses additional novel peptide analogs and derivatives of T-140, including 4F-benzoyl-TN14003 (SEQ ID NO:1). The '462 publication further discloses novel preventive and therapeutic compositions and methods of using same utilizing T-140 analogs for the treatment of cancer and chronic rheumatoid arthritis. The specification of '462 demonstrates the ability of these peptides to inhibit cancer cell migration, including breast cancer and leukemia cells, and to inhibit metastasis formation in vivo. Further demonstrated therein is inhibition of delayed-type hypersensitivity reaction in mice and collagen-induced arthritis, an animal model of rheumatoid arthritis.

WO 2004/087068 is directed to a method for treating or preventing a CXCR4 mediated pathology comprising administering a CXCR4 peptide antagonist to a host in an amount sufficient to inhibit CXCR4 signal transduction in a cell expressing a CXCR4 receptor or homologue thereof, wherein the CXCR4 peptide antagonist is not an antibody or fragment thereof. The '068 publication discloses that exemplary CXCR4 peptide antagonists include T140 and derivatives of T140, and that the pathology includes cancer such as breast, brain, pancreatic, ovarian, prostate, kidney, and non-small lunch cancer. Other publications directed to the use of CXCR4 antagonists in cancer therapy include, for example, WO 00/09152, US 2002/0156034, and WO 2004/024178.

A recent publication by some of the inventors of the present invention (Avniel et al., 2006) discloses that blocking the CXCR4/CXCL12 axis by a T-140 analog resulted in a significant reduction in eosinophil accumulation in the dermis and improved epithelialization, thus significantly improving skin recovery after burns.

None of the prior art discloses or suggests that CXCR4 inhibitor peptides belonging to the T-140 analog family may also affect CXCR4 activity in an agonist manner. There exists a long felt need for compositions and methods useful for modulating CXCR4-mediated processes involved in pathological conditions in vivo.

SUMMARY OF THE INVENTION

The present invention is directed to novel therapeutic applications of T-140 analog peptides. The present invention discloses, for the first time, that T-140 analogs, hitherto known as CXCR4 inhibitors, unexpectedly also possess CXCR4 super-agonistic properties. The present invention thus provides compositions and methods utilizing T-140 analogs in applications in which activation of CXCR4 in an agonistic manner is beneficial, such as for inducing tumor cell death in hematopoietic and glial malignancies.

The invention is also based, in part, on the unexpected discovery that the known T-140 analog 4F-benzoyl-TN14003 (4F-benzoyl-Arg-Arg-Nal-Cys-Tyr-Cit-Lys-DLys-Pro-Tyr-Arg-Cit-Cys-Arg-NH$_2$, SEQ ID NO:1), but not the bicyclam CXCR4 inhibitor AMD3100, can selectively, specifically and rapidly stimulate multiple myeloma, glioma and leukemia cell death, both in vitro and in vivo, thus demonstrating increased anti-tumor effects particularly on tumors of hematopoietic and glial origin. Unexpectedly, 4F-benzoyl-TN14003 was also found to synergize with rapamycin in inducing multiple myeloma cell death.

According to certain embodiments of the invention, the 4F-benzoyl-TN14003 and analogs and derivatives thereof are now disclosed to be particularly useful in the treatment of hematopoietic and glial tumors. Specifically, there is provided a method for treating a subject having a tumor selected from the group consisting of multiple myeloma, microglioma and glioma, comprising administering to the subject a therapeutically effective amount of a peptide having an amino acid sequence as set forth in SEQ ID NO:1 or an analog or derivative thereof.

The 4F-benzoyl-TN14003 analogs and derivatives used in the novel compositions and methods of the invention are the structurally and functionally related peptides disclosed in patent applications WO 2002/020561 and WO 2004/020462, also known as "T-140 analogs", as detailed hereinbelow.

In various particular embodiments, the analog or derivative has an amino acid sequence as set forth in the following formula (I) or a salt thereof:

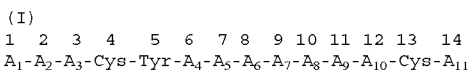

wherein:
- $A_1$ is an arginine, lysine, ornithine, citrulline, alanine or glutamic acid residue or a N-α-substituted derivative of these amino acids, or $A_1$ is absent;
- $A_2$ represents an arginine or glutamic acid residue if $A_1$ is present, or $A_2$ represents an arginine or glutamic acid residue or a N-α-substituted derivative of these amino acids if $A_1$ is absent;
- $A_3$ represents an aromatic amino acid residue;
- $A_4$, $A_5$ and $A_9$ each independently represents an arginine, lysine, ornithine, citrulline, alanine or glutamic acid residue;
- $A_6$ represents a proline, glycine, ornithine, lysine, alanine, citrulline, arginine or glutamic acid residue;
- $A_7$ represents a proline, glycine, ornithine, lysine, alanine, citrulline or arginine residue;
- $A_8$ represents a tyrosine, phenylalanine, alanine, naphthylalanine, citrulline or glutamic acid residue;
- $A_{10}$ represents a citrulline, glutamic acid, arginine or lysine residue;
- $A_{11}$ represents an arginine, glutamic acid, lysine or citrulline residue wherein the C-terminal carboxyl may be derivatized;

and the cysteine residue of the 4-position or the 13-position can form a disulfide bond, and the amino acids can be of either L or D form.

Exemplary peptides according to formula (I) are peptides having an amino acid sequence as set forth in any one of SEQ ID NOS:1-72, as presented in Table 1 hereinbelow.

In another preferable embodiment, the analog or derivative has an amino acid sequence as set forth in SEQ ID NO:65 (H-Arg-Arg-Nal-Cys-Tyr-Cit-Lys-DLys-Pro-Tyr-Arg-Cit-Cys-Arg-OH; TC14003).

In certain other particular embodiments, said analog or derivative is selected from the group consisting of:

```
                                            (SEQ ID NO: 1)
4F-benzoyl-Arg-Arg-Nal-Cys-Tyr-Cit-Lys-DLys-Pro- Tyr-Arg-Cit-Cys-Arg-NH2, (SEQ ID NO: 2)
Ac-Arg-Arg-Nal-Cys-Tyr-Cit-Lys-DLys-Pro-Tyr-Arg- Cit-Cys-Arg-OH, (SEQ ID NO: 3)
Ac-Arg-Arg-Nal-Cys-Tyr-Arg-Lys-DCit-Pro-Tyr-Arg- Cit-Cys-Arg-OH, (SEQ ID NO: 4)
Ac-Arg-Arg-Nal-Cys-Tyr-Cit-Lys-DCit-Pro-Tyr-Arg- Cit-Cys-Arg-OH, (SEQ ID NO: 10)
Ac-Arg-Arg-Nal-Cys-Tyr-Cit-Lys-DCit-Pro-Tyr-Arg- Cit-Cys-Arg-NH2, (SEQ ID NO: 46)
TMguanyl-Arg-Arg-Nal-Cys-Tyr-Cit-Lys-DCit-Pro- Tyr-Arg-Cit-Cys-Arg-NH2;, (SEQ ID NO: 47)
ACA-Arg-Arg-Nal-Cys-Tyr-Cit-Lys-DCit-Pro-Tyr-Arg- Cit-Cys-Arg-NH2, (SEQ ID NO: 51)
Ac-Arg-Arg-Nal-Cys-Tyr-Cit-Lys-DLys-Pro-Tyr-Arg- Cit-Cys-Arg-NH2, (SEQ ID NO: 52)
Ac-Arg-Arg-Nal-Cys-Tyr-Arg-Lys-DCit-Pro-Tyr-Arg- Cit-Cys-Arg-NH2, (SEQ ID NO: 53)
4F-benzoyl-Arg-Arg-Nal-Cys-Tyr-Cit-Lys-DGlu-Pro- Tyr-Arg-Cit-Cys-Arg-NHMe, (SEQ ID NO: 54)
4F-benzoyl-Arg-Arg-Nal-Cys-Tyr-Cit-Lys-DGlu-Pro- Tyr-Arg-Cit-Cys-Arg-NHEt, (SEQ ID NO: 55)
4F-benzoyl-Arg-Arg-Nal-Cys-Tyr-Cit-Lys-DGlu-Pro- Tyr-Arg-Cit-Cys-Arg-NHiPr, (SEQ ID NO: 56)
4F-benzoyl-Arg-Arg-Nal-Cys-Tyr-Cit-Lys-DGlu-Pro- Tyr-Arg-Cit-Cys-Arg-tyramine, (SEQ ID NO: 65)
H-Arg-Arg-Nal-Cys-Tyr-Cit-Lys-DLys-Pro-Tyr-Arg- Cit-Cys-Arg-OH, (SEQ ID NO: 66)
H-Arg-Arg-Nal-Cys-Tyr-Cit-Lys-DLys-Pro-Tyr-Arg- Cit-Cys-Arg-NH2

(SEQ ID NO: 68)
H-Arg-Arg-Nal-Cys-Tyr-Cit-Lys-DCit-Pro-Tyr-Arg-

Cit-Cys-Arg-NH2, (SEQ ID NO: 70)
H-Arg-Arg-Nal-Cys-Tyr-Cit-Lys-DCit-Pro-Tyr-Arg-

Cit-Cys-Arg-OH,
and (SEQ ID NO: 71)
H-Arg-Arg-Nal-Cys-Tyr-Arg-Lys-DCit-Pro-Tyr-Arg- Cit-Cys-Arg-OH.
```

In another aspect, there is provided a method for inducing hematopoietic tumor cell death in a subject in need thereof, comprising administering to the subject a therapeutically effective amount of a peptide having an amino acid sequence as set forth in SEQ ID NO:1 or an analog or derivative thereof. In another particular embodiment, the tumor is selected from leukemia, lymphoma, microglioma and multiple myeloma. In a particular embodiment, the tumor is multiple myeloma.

In another aspect, there is provided a method for inducing glial tumor cell death in a subject in need thereof, comprising administering to the subject a therapeutically effective amount of a peptide having an amino acid sequence as set forth in SEQ ID NO:1 or an analog or derivative thereof.

Without wishing to be bound by any theory or mechanism of action, the T-140 analogs of the invention are useful for inducing tumor cell apoptosis.

Other embodiments of the present invention are directed to the use of 4F-benzoyl-TN14003 or an analog or derivative thereof for sensitizing tumors to chemotherapeutic or other anti-cancer drugs.

Thus, in another aspect, there is provided a method for increasing the sensitivity of tumor cells to an anti-cancer agent in a subject in need thereof comprising administering to the subject a sensitizing-effective amount of a peptide having an amino acid sequence as set forth in SEQ ID NO:1 or an analog or derivative thereof in concurrent or sequential combination with the anti-cancer agent.

In another embodiment, the anti-cancer agent is a chemotherapeutic drug. For example, the chemotherapeutic drug may be selected from alkylators (e.g. cyclophosphamide and isophosphamide and platinum-containing compounds), anthracyclines, antibiotics (e.g. adreamaycin), aromatase inhibitors, bisphosphonates, cyclo-oxygenase inhibitors, estrogen receptor modulators, folate antagonists, inorganic aresenates, microtubule inhibitors (e.g. taxanes), nitrosoureas, nucleoside analogs, osteoclast inhibitors, retinoids, proteasome inhibitors (e.g. Velcade), topoisomerase 1 inhibitors, topoisomerase 2 inhibitors, antimetabolites (e.g. Methotrexate) and tyrosine kinase inhibitors.

In another particular embodiment, the drug is an apoptosis-inducing drug. In a preferable embodiment, the drug is rapamycin or a derivative thereof.

In another particular embodiment, the drug is an immunosuppressant used to treat hematopoietic tumors such as corticosteroids (e.g. dexamethasone) and immunosuppressive antibodies (e.g. Mabthera).

In another particular embodiment, the tumor is a hematopoietic tumor (e.g. leukemia, lymphoma, multiple myeloma and microglioma).

In another particular embodiment, the tumor is a glial tumor (e.g. ependymomas, astrocytomas, oligodendrogliomas and mixed gliomas, such as oligoastrocytomas).

In another aspect, the invention provides a pharmaceutical composition comprising as active ingredients a peptide having an amino acid sequence as set forth in SEQ ID NO:1 or an analog or derivative thereof and rapamycin or a derivative thereof.

The combinations of the invention may also be in form of a kit or a pharmaceutical pack containing one or more courses of treatment for a neoplasm in a subject in need thereof. Thus, there is provided in another aspect a kit containing i) a peptide having an amino acid sequence as set forth in SEQ ID NO:1 or an analog or derivative thereof and ii) a chemotherapeutic agent comprising rapamycin or a derivative thereof, and optionally iii) instructions for administering said peptide and said chemotherapeutic agent to a subject in need thereof, e.g. to a subject afflicted with a hematopoietic or glial tumor.

Other objects, features and advantages of the present invention will become clear from the following description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 demonstrates that 4F-benzoyl-TN14003 enhances MIP3α secretion by the prostate cancer cell line PC3 in a CXCR4-dependent manner.

FIG. 2 depicts the effect of 4F-benzoyl-TN14003 on proliferation of normal hematopoietic cells and primary keratinocytes.

FIG. 3 illustrates the effect of AMD-3100 and 4F-benzoyl-TN14003 on the proliferation of prostate carcinoma PC3 and PC3-CXCR4.5 cells.

FIG. 5 shows the effect of 4F-benzoyl-TN14003 on proliferation of K562 CML cells.

FIG. 6 illustrates the effect of 4F-benzoyl-TN14003 on proliferation of HL-60 and NB4 AML cells.

FIG. 8 demonstrates that the effect of 4F-benzoyl-TN14003 on the proliferation of RPMI8226MM cells and migration of T cell leukemia Jurkat cell is abolished upon treatment with Proteinease K.

FIG. 9 illustrates the effect of 4F-benzoyl-TN14003 on the proliferation and survival of RPMI8226MM cells over time.

FIG. 10 depicts the effect of 4F-benzoyl-TN14003 on apoptosis of RPMI8226MM cells.

FIG. 11 illustrates the effect of 4F-benzoyl-TN14003 on the proliferation and survival of BM derived primary MM cells. The effect of 4F-benzoyl-TN14003 on the survival of BM derived cells from MM patients with different percentage of CD138+ MM cells. FIGS. 11A and 11C, 100% MM cells. FIG. 11B, 80% MM cells. FIG. 11D, 5% MM cells.

FIG. 12 demonstrates the effect of 4F-benzoyl-TN14003 on the survival of BM derived MM CD138 and CD34 positive cells.

FIG. 15 presents the effect of 4F-benzoyl-TN14003 on the proliferation and survival of U87 glioma cells.

FIG. 17 presents the effect of s.c. injection of 4F-benzoyl-TN14003 (8 mg/Kg) on NB4, derived tumor growth.

FIG. 18 demonstrates detection of K562L cells in vivo using the CCCD camera, 24 hr after IP injection.

FIG. 22 demonstrates that 4F-benzoyl-TN14003 inhibits MM cell growth in vivo.

DETAILED DESCRIPTION OF THE INVENTION

Figure 1A:
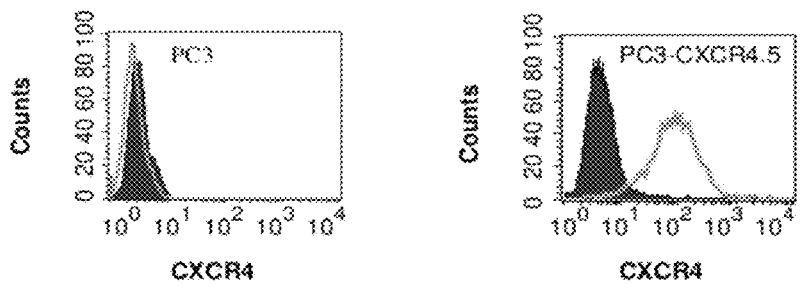
FIG. 1A illustrates FACS analysis of PC3 cells (left panel) and PC3-CXCR4.5 cells (right panel) stained for the control and CXCR4 antibodies.

The present invention is directed to novel compositions and methods wherein T-140 analog peptides, hitherto known as CXCR4 antagonists, are used to stimulate CXCR4-mediated processes in an agonistic manner.

The present invention discloses for the first time that 4F-benzoyl-TN14003 (SEQ ID NO:1), a known CXCR4 inhibitor belonging to the T-140 peptide family, mediates unique beneficial effects, which are not mediated by other CXCR4 inhibitors such as AMD3100. Unexpectedly, 4F-benzoyl-TN14003 was found to induce apoptosis in hematopoietic tumors such as glioma and multiple myeloma, and to enhance tumor cell apoptosis induced by rapamycin.

T-140 Analogs

The peptides described in this specification have an N-terminus (amino-terminal) at the left extremity and a C-terminus (carboxyl-terminal) at the right extremity in accordance with the customary practice of peptide notations.

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown below. If an optical isomer exists with respect to an amino acid, it preferably represents the L form unless otherwise expressly specified.

Gly or G: glycine; Ala or A: alanine; Val or V: valine; Leu or L: leucine; Ile or I: isoleucine; Ser or S: serine; Thr or T: threonine; Cys or C: cysteine; Met or M: methionine; Glu or E: glutamic acid; Asp or D: aspartic acid; Lys or K: lysine; Arg or R: arginine; His or H: histidine; Phe or F: phenylalanine; Tyr or Y: tyrosine; Trp or W: tryptophan; Pro or P: proline; Asn or N: asparagine; Gln or Q: glutamine; pGlu: pyroglutamic acid; Nal: 3-(2-naphthyl) alanine; Cit: citrulline; DLys: D-lysine; DCit: D-citrulline; DGlu: D-glutamic acid; Me: methyl group; Et: ethyl group; Bu: butyl group; Ph: phenyl group.

The substituents, protective group and reagents often used in this specification are indicated by the following codes.

BHA: benzhydrylamine
pMBHA: p-methylbenzhydrylamine
Tos: p-toluenesulphonyl
CHO: formyl
HONB: N-hydroxy-5-norbornene-2,3-dicarboximide
OcHex: cyclohexyl ester
Bzl: benzyl
Cl$_2$-Bzl: dichloro-benzyl
Bom: benzyloxymethyl
Z: benzyloxycarbonyl
Br—Z: 2-bromobenzyloxycarbonyl
Boc: t-butyloxycarbonyl
DCM: dichloromethane
HOBt: 1-hydroxybenzotriazole
DCC: N,N'-dicyclohexylcarbodiimide
TFA: trifluoroacetic acid
DIEA: diisopropylethylamine
Fmoc: N-9-fluorenylmethoxycarbony
DNP: dinitrophenyl
Bum: tertiarybutoxymethyl
Trt: trityl
Ac: acetyl
Guanyl: guanyl
Succinyl: succinyl
glutaryl: glutaryl
TMguanyl: tetramethylguanyl
2F-benzoyl: 2-fluorobenzoyl
4F-benzoyl: 4-fluorobenzoyl
APA: 5-aminopentanoyl
ACA: 6-aminohexanoyl
desamino-Arg: 2-desamino-arginyl
deamino TMG-APA: the following formula (IV):

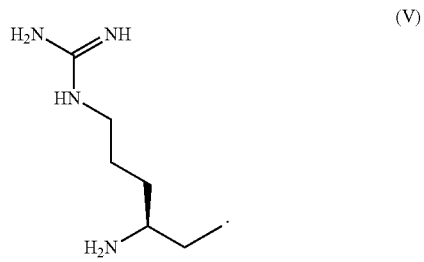

R—CH2: the following formula (V):

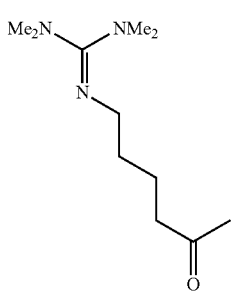

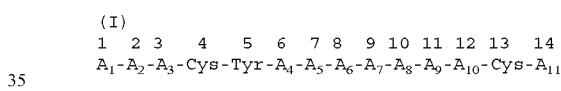

In N-terminal amino acids, [H—] indicates that the terminal amino group is not derivatized, and in C-terminal amino acids, [—OH] indicates that the terminal carboxyl group is not derivatized.

The 4F-benzoyl-TN14003 analogs and derivatives of the invention belong to a family of structurally closely related peptides, also known as T-140 analogs.

T-140 is a known peptide having the amino acid sequence H-Arg-Arg-Nal-Cys-Tyr-Arg-Lys-DLys-Pro-Tyr-Arg-Cit-Cys-Arg-OH (SEQ ID NO:69, Tamamura et al., 2003). The preferable peptides of the invention include analogs and derivatives disclosed in patent applications WO 2002/020561 and WO 2004/020462.

In one aspect, the present invention relates to the use of pharmaceutical compositions comprising as an active ingredient a peptide indicated by the following formula (I) or a salt thereof:

(I)
$$\begin{array}{cccccccccccccc}1&2&3&4&5&6&7&8&9&10&11&12&13&14\\A_1\text{-}&A_2\text{-}&A_3\text{-}&Cys\text{-}&Tyr\text{-}&A_4\text{-}&A_5\text{-}&A_6\text{-}&A_7\text{-}&A_8\text{-}&A_9\text{-}&A_{10}\text{-}&Cys\text{-}&A_{11}\end{array}$$

wherein:

$A_1$ in the above-mentioned formula (I) represents an arginine, lysine, ornithine, citrulline, alanine or glutamic acid residue (either L or D form) which may be derivatized at the N-terminus, or $A_1$ is a hydrogen atom, or it is preferable that $A_1$ is an arginine, citrulline, alanine or D-glutamic acid residue, or $A_1$ is a hydrogen atom.

Examples of "N-terminal derivatized peptides" or "N-α-substituted derivatives" include, but are not limited to, those protected by formyl group; acyl group, e.g., acetyl group, propionyl group, butyryl group, pentanoyl group, C2-6alkanoyl group e.g. hexanoyl group, benzoyl group, arylcarbonyl group e.g. substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobezoyl group, 4-nirtobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesulfonyl group, mesitylenesulfonyl group, 4-aminobenzenesulfonyl group, dansyl group, 4-bromobenzenesulfonyl group) etc. Or, the amino acid group of N-terminal may be absent.

Optionally and preferably, the peptide is derivatized at the N terminus with a substituted benzoyl group. In a particular embodiment, the substituted benzoyl group is a 4-fluorobenzoyl group. In another particular embodiment, the substituted benzoyl group is a 2-fluorobenzoyl group.

$A_2$ in the above-mentioned formula (I) represents an arginine or glutamic acid residue (either L or D form) if A1 is an arginine, lysine, ornithine, citrulline, alanine or glutamic acid residue (either L or D form) which may be derivatized at the N-terminal, or $A_2$ represents an arginine or glutamic acid residue (either L or D form) which may be derivatized at the N-terminus if $A_1$ is absent, or it is preferable that $A_2$ is an arginine or glutamic acid residue if $A_1$ is an arginine, citrulline, alanine or glutamic acid residue which may be derivatized at the N-terminal, or $A_2$ is an arginine or glutamic acid residue which may be derivatized at N-terminal if $A_1$ is absent. Examples of "peptides derivatized at the N-terminal" include, but are not limited to, the same ones as those mentioned in A1.

$A_3$ in the above-mentioned formula (I) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, $A_3$ represents phenylalanine, tryptophan or 3-(2-naphthyl)alanine.

$A_4$ in the above-mentioned formula (I) represents an arginine, lysine, ornithine, citrulline, alanine or glutamic acid residue (either L or D form), or it is preferable that $A_4$ is an arginine, citrulline, alanine or L- or D-glutamic acid residue.

$A_5$ in the above-mentioned formula (I) represents an arginine, lysine, ornithine, citrulline, alanine or glutamic acid residue (either L or D form), or it is preferable that $A_5$ is an arginine, citrulline, alanine, lysine or glutamic acid residue.

$A_6$ in the above-mentioned formula (I) represents a proline, glycine, ornithine, lysine, alanine, citrulline, arginine or glutamic acid residue (either L or D form), or it is preferable that $A_6$ is a D-lysine, D-alanine, D-citrulline or D-glutamic acid residue.

$A_7$ in the above-mentioned formula (I) represents a proline, glycine, ornithine, lysine, alanine, citrulline or arginine residue (either L or D form), or it is preferable that $A_7$ is a proline or alanine residue.

$A_8$ in the above-mentioned formula (I) represents a tyrosine, phenylalanine, alanine, naphthylalanine, citrulline or glutamic acid residue (either L or D form), or it is preferable that $A_8$ is a tyrosine, alanine or D-glutamic acid residue.

$A_9$ in the above-mentioned formula (I) represents an arginine, lysine, ornithine, citrulline, alanine or glutamic, acid residue (either L or D form), or it is preferable that $A_9$ is an arginine, citrulline or glutamic acid residue.

$A_{10}$ in the above-mentioned formula (I) represents a citrulline, glutamic acid, arginine or lysine residue (either L or D form), or it is preferable that $A_{10}$ is a citrulline or D-glutamic acid residue.

$A_{11}$ in the above-mentioned formula (I) represents an arginine, glutamic acid, lysine or citrulline residue (either L or D form) which may be derivatized at C-terminal, or it is preferable that $A_{11}$ is an arginine or glutamic acid residue which may be derivatized at C-terminal.

"C-terminal derivatization" or "C-terminal carboxyl derivatization" includes, without limitation, amidation (—$CONH_2$, —CONHR, —CONRR') and esterification (—COOR). Herein, R and R' in amides and esters include, for example, $C_{1-6}$ alkyl group e.g. methyl, ethyl, n-propyl, iso-propyl, or n-butyl, $C_{3-8}$ cycloalkyl group e.g. cyclopentyl, cyclohexyl, $C_{6-12}$ aryl group e.g. phenyl and α-naphthyl, phenyl-$C_{1-2}$ alkyl group e.g. benzyl, phenethyl or $C_{7-14}$ aralkyl group e.g. $C_{1-2}$ alkyl group e.g. α-naphthyl methyl group, and additionally, pivaloyloxymethyl group which is generally used as an oral bioavailable ester.

If a peptide of the present invention has carboxy groups (or carboxylates) at side-chain terminals other than C-terminal, the peptide having amidated or esterificated carboxy groups at side-chain terminals is included in the peptides of the present invention. As the amides and esters in this case, for example, the amides and esters exemplified in $A_{11}$ are similarly used. Also, the peptides of the present invention include peptides in which substituents (e.g. —OH, —SH, amino group, imidazole group, indole group, guanidino group, etc.) on the intramolecular amino acid side chains are protected by suitable protective group (e.g. C1-6 acyl group, C2-6 alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

In one embodiment, the composition comprises a peptide as set forth in formula (I) as defined hereinabove, wherein $A_1$ is a glutamic acid residue or is absent.

In another embodiment, the composition comprises a peptide as set forth in formula (I) as defined hereinabove, wherein $A_4$ is a glutamic acid residue.

In another embodiment, the composition comprises a peptide as set forth in formula (I) as defined hereinabove, wherein $A_6$ is a glutamic acid residue.

In another embodiment, the composition comprises a peptide as set forth in formula (I) as defined hereinabove, wherein $A_8$ is a glutamic acid residue.

In another embodiment, the composition comprises a peptide as set forth in formula (I) as defined hereinabove, wherein $A_9$ is a glutamic acid residue.

In another embodiment, the composition comprises a peptide as set forth in formula (I) as defined hereinabove, wherein $A_5$ is an arginine or glutamic acid residue.

In another embodiment, the composition comprises a peptide as set forth in formula (I) as defined hereinabove, wherein $A_{10}$ is a glutamic acid, arginine or lysine residue.

In another embodiment, the composition comprises a peptide as set forth in formula (I) as defined hereinabove, wherein $A_{11}$ is a glutamic acid, lysine or citrulline residue.

In another embodiment, the peptide has an amino acid sequence as set forth in any one of SEQ ID NOS:1-72 presented in Table 1 herein:

TABLE 1

T-140 and currently preferred T-140 analogs

| Analog | SEQ ID NO: | Amino acid sequence |
|---|---|---|
| 4F-benzoyl-TN14003 | 1 | 4F-benzoyl-Arg-Arg-Nal-Cys-Tyr-Cit-Lys-DLys-Pro-Tyr-Arg-Cit-Cys-Arg-$NH_2$ |
| AcTC14003 | 2 | Ac-Arg-Arg-Nal-Cys-Tyr-Cit-Lys-DLys-Pro-Tyr-Arg-Cit-Cys-Arg-OH |

TABLE 1-continued

T-140 and currently preferred T-140 analogs

| Analog | SEQ ID NO: | Amino acid sequence |
|---|---|---|
| AcTC14005 | 3 | Ac-Arg-Arg-Nal-Cys-Tyr-Arg-Lys-DCit-Pro-Tyr-Arg-Cit-Cys-Arg-OH |
| AcTC14011 | 4 | Ac-Arg-Arg-Nal-Cys-Tyr-Cit-Lys-DCit-Pro-Tyr-Arg-Cit-Cys-Arg-OH |
| AcTC14013 | 5 | Ac-Arg-Arg-Nal-Cys-Tyr-Cit-Lys-DLys-Pro-Tyr-Cit-Cit-Cys-Arg-OH |
| AcTC14015 | 6 | Ac-Cit-Arg-Nal-Cys-Tyr-Cit-Lys-DLys-Pro-Tyr-Arg-Cit-Cys-Arg-OH |
| AcTC14017 | 7 | Ac-Cit-Arg-Nal-Cys-Tyr-Arg-Lys-DCit-Pro-Tyr-Arg-Cit-Cys-Arg-OH |
| AcTC14019 | 8 | Ac-Arg-Arg-Nal-Cys-Tyr-Arg-Lys-DCit-Pro-Tyr-Cit-Cit-Cys-Arg-OH |
| AcTC14021 | 9 | Ac-Cit-Arg-Nal-Cys-Tyr-Arg-Lys-DLys-Pro-Tyr-Cit-Cit-Cys-Arg-OH |
| AcTC14012 | 10 | Ac-Arg-Arg-Nal-Cys-Tyr-Cit-Lys-DCit-Pro-Tyr-Arg-Cit-Cys-Arg-NH$_2$ |
| AcTC14014 | 11 | Ac-Arg-Arg-Nal-Cys-Tyr-Cit-Lys-DLys-Pro-Tyr-Cit-Cit-Cys-Arg-NH$_2$ |
| AcTC14016 | 12 | Ac-Cit-Arg-Nal-Cys-Tyr-Cit-Lys-DLys-Pro-Tyr-Arg-Cit-Cys-Arg-NH$_2$ |
| AcTC14018 | 13 | Ac-Cit-Arg-Nal-Cys-Tyr-Arg-Lys-DCit-Pro-Tyr-Arg-Cit-Cys-Arg-NH$_2$ |
| AcTC14020 | 14 | Ac-Arg-Arg-Nal-Cys-Tyr-Arg-Lys-DCit-Pro-Tyr-Cit-Cit-Cys-Arg-NH$_2$ |
| AcTC14022 | 15 | Ac-Cit-Arg-Nal-Cys-Tyr-Arg-Lys-DLys-Pro-Tyr-Cit-Cit-Cys-Arg-NH$_2$ |
| TE14001 | 16 | H-DGlu-Arg-Nal-Cys-Tyr-Arg-Lys-DLys-Pro-Tyr-Arg-Cit-Cys-Arg-OH |
| TE14002 | 17 | H-Arg-Glu-Nal-Cys-Tyr-Arg-Lys-DLys-Pro-Tyr-Arg-Cit-Cys-Arg-OH |
| TE14003 | 18 | H-Arg-Arg-Nal-Cys-Tyr-Glu-Lys-DLys-Pro-Tyr-Arg-Cit-Cys-Arg-OH |
| TE14004 | 19 | H-Arg-Arg-Nal-Cys-Tyr-Arg-Glu-DLys-Pro-Tyr-Arg-Cit-Cys-Arg-OH |
| TE14005 | 20 | H-Arg-Arg-Nal-Cys-Tyr-Arg-Lys-DGlu-Pro-Tyr-Arg-Cit-Cys-Arg-OH |
| TE14006 | 21 | H-Arg-Arg-Nal-Cys-Tyr-Arg-Lys-DLys-Pro-Tyr-Glu-Cit-Cys-Arg-OH |
| TE14007 | 22 | H-Arg-Arg-Nal-Cys-Tyr-Arg-Lys-DLys-Pro-Tyr-Arg-Cit-Cys-Glu-OH |
| TE14011 | 23 | H-Arg-Arg-Nal-Cys-Tyr-Cit-Lys-DGlu-Pro-Tyr-Arg-Cit-Cys-Arg-NH$_2$ |
| TE14012 | 24 | H-Arg-Arg-Nal-Cys-Tyr-DGlu-Lys-DCit-Pro-Tyr-Arg-Cit-Cys-Arg-NH$_2$ |
| TE14013 | 25 | H-Arg-Arg-Nal-Cys-Tyr-DGlu-Lys-DGlu-Pro-Tyr-Arg-Cit-Cys-Arg-NH$_2$ |
| TE14014 | 26 | H-DGlu-Arg-Nal-Cys-Tyr-Cit-Lys-DGlu-Pro-Tyr-Arg-Cit-Cys-Arg-NH$_2$ |
| TE14015 | 27 | H-Arg-Arg-Nal-Cys-Tyr-Cit-Lys-DGlu-Pro-DGlu-Arg-Cit-Cys-Arg-NH$_2$ |
| TE14016 | 28 | H-Arg-Arg-Nal-Cys-Tyr-Cit-Lys-DGlu-Pro-Tyr-Arg-DGlu-Cys-Arg-NH$_2$ |
| AcTE14014 | 29 | Ac-DGlu-Arg-Nal-Cys-Tyr-Cit-Lys-DGlu-Pro-Tyr-Arg-Cit-Cys-Arg-NH$_2$ |
| AcTE14015 | 30 | Ac-Arg-Arg-Nal-Cys-Tyr-Cit-Lys-DGlu-Pro-DGlu-Arg-Cit-Cys-Arg-NH$_2$ |
| AcTE14016 | 31 | Ac-Arg-Arg-Nal-Cys-Tyr-Cit-Lys-DGlu-Pro-Tyr-Arg-DGlu-Cys-Arg-NH$_2$ |
| TF1: AcTE14011 | 32 | Ac-Arg-Arg-Nal-Cys-Tyr-Cit-Lys-DGlu-Pro-Tyr-Arg-Cit-Cys-Arg-NH$_2$ |
| TF2: guanyl-TE14011 | 33 | guanyl-Arg-Arg-Nal-Cys-Tyr-Cit-Lys-DGlu-Pro-Tyr-Arg-Cit-Cys-Arg-NH$_2$ |
| TF3: TMguanyl-TE14011 | 34 | TMguanyl-Arg-Arg-Nal-Cys-Tyr-Cit-Lys-DGlu-Pro-Tyr-Arg-Cit-Cys-Arg-NH$_2$ |
| TF4: | 35 | TMguanyl-Arg-Nal-Cys-Tyr-Cit-Lys-DGlu-Pro-Tyr-Arg-Cit-Cys-Arg- |

TABLE 1-continued

T-140 and currently preferred T-140 analogs

| Analog | SEQ ID NO: | Amino acid sequence |
|---|---|---|
| TMguanyl-TE14011 (2-14) | | NH₂ |
| TF5: 4F-benzoyl-TE14011 | 36 | 4F-benzoyl-Arg-Arg-Nal-Cys-Tyr-Cit-Lys-DGlu-Pro-Tyr-Arg-Cit-Cys-Arg-NH₂ |
| TF6: 2F-benzoyl-TE14011 | 37 | 2F-benzoyl-Arg-Arg-Nal-Cys-Tyr-Cit-Lys-DGlu-Pro-Tyr-Arg-Cit-Cys-Arg-NH₂ |
| TF7: APA-TE14011 (2-14) | 38 | APA-Arg-Nal-Cys-Tyr-Cit-Lys-DGlu-Pro-Tyr-Arg-Cit-Cys-Arg-NH₂ |
| TF8: desamino-R-TE14011 (2-14) | 39 | desamino-R-Arg-Nal-Cys-Tyr-Cit-Lys-DGlu-Pro-Tyr-Arg-Cit-Cys-Arg-NH₂ |
| TF9: guanyl-TE14011 (2-14) | 40 | Guanyl-Arg-Nal-Cys-Tyr-Cit-Lys-DGlu-Pro-Tyr-Arg-Cit-Cys-Arg-NH₂ |
| TF10: succinyl-TE14011 (2-14) | 41 | succinyl-Arg-Nal-Cys-Tyr-Cit-Lys-DGlu-Pro-Tyr-Arg-Cit-Cys-Arg-NH₂ |
| TF11: glutaryl-TE14011 (2-14) | 42 | glutaryl-Arg-Nal-Cys-Tyr-Cit-Lys-DGlu-Pro-Tyr-Arg-Cit-Cys-Arg-NH₂ |
| TF12: deaminoTMG-APA-TE14011 (2-14) | 43 | deaminoTMG-APA-Arg-Nal-Cys-Tyr-Cit-Lys-DGlu-Pro-Tyr-Arg-Cit-Cys-Arg-NH₂ |
| TF15: H-Arg-CH2NH-RTE14011 (2-14) | 44 | R-CH2-Arg-Nal-Cys-Tyr-Cit-Lys-DGlu-Pro-Tyr-Arg-Cit-Cys-Arg-NH₂ |
| TF17: TE14011 (2-14) | 45 | H-Arg-Nal-Cys-Tyr-Cit-Lys-DGlu-Pro-Tyr-Arg-Cit-Cys-Arg-NH₂ |
| TF18: TMguanyl-TC14012 | 46 | TMguanyl-Arg-Arg-Nal-Cys-Tyr-Cit-Lys-DCit-Pro-Tyr-Arg-Cit-Cys-Arg-NH₂ |
| TF19: ACA-TC14012 | 47 | ACA-Arg-Arg-Nal-Cys-Tyr-Cit-Lys-DCit-Pro-Tyr-Arg-Cit-Cys-Arg-NH₂ |
| TF20: ACA-T140 | 48 | ACA-Arg-Arg-Nal-Cys-Tyr-Arg-Lys-DLys-Pro-Tyr-Arg-Cit-Cys-Arg-OH |
| TZ14011 | 49 | H-Arg-Arg-Nal-Cys-Tyr-Cit-Arg-DLys-Pro-Tyr-Arg-Cit-Cys-Arg-NH₂ |
| AcTZ14011 | 50 | Ac-Arg-Arg-Nal-Cys-Tyr-Cit-Arg-DLys-Pro-Tyr-Arg-Cit-Cys-Arg-NH₂ |
| AcTN14003 | 51 | Ac-Arg-Arg-Nal-Cys-Tyr-Cit-Lys-DLys-Pro-Tyr-Arg-Cit-Cys-Arg-NH₂ |
| AcTN14005 | 52 | Ac-Arg-Arg-Nal-Cys-Tyr-Arg-Lys-DCit-Pro-Tyr-Arg-Cit-Cys-Arg-NH₂ |
| 4F-benzoyl-TN14011-Me | 53 | 4F-benzoyl-Arg-Arg-Nal-Cys-Tyr-Cit-Lys-DGlu-Pro-Tyr-Arg-Cit-Cys-Arg-NHMe |
| 4F-benzoyl-TN14011-Et | 54 | 4F-benzoyl-Arg-Arg-Nal-Cys-Tyr-Cit-Lys-DGlu-Pro-Tyr-Arg-Cit-Cys-Arg-NHEt |

TABLE 1-continued

T-140 and currently preferred T-140 analogs

| Analog | SEQ ID NO: | Amino acid sequence |
|---|---|---|
| 4F-benzoyl-TN14011-1Pr | 55 | 4F-benzoyl-Arg-Arg-Nal-Cys-Tyr-Cit-Lys-DGlu-Pro-Tyr-Arg-Cit-Cys-Arg-NHiPr |
| 4F-benzoyl-TN14011-tyramine | 56 | 4F-benzoyl-Arg-Arg-Nal-Cys-Tyr-Cit-Lys-DGlu-Pro-Tyr-Arg-Cit-Cys-Arg-tyramine |
| TA14001 | 57 | H-Ala-Arg-Nal-Cys-Tyr-Arg-Lys-DLys-Pro-Tyr-Arg-Cit-Cys-Arg-OH |
| TA14005 | 58 | H-Arg-Arg-Nal-Cys-Tyr-Ala-Lys-DLys-Pro-Tyr-Arg-Cit-Cys-Arg-OH |
| TA14006 | 59 | H-Arg-Arg-Nal-Cys-Tyr-Arg-Ala-DLys-Pro-Tyr-Arg-Cit-Cys-Arg-OH |
| TA14007 | 60 | H-Arg-Arg-Nal-Cys-Tyr-Arg-Lys-DAla-Pro-Tyr-Arg-Cit-Cys-Arg-OH |
| TA14008 | 61 | H-Arg-Arg-Nal-Cys-Tyr-Arg-Lys-DLys-Ala-Tyr-Arg-Cit-Cys-Arg-OH |
| TA14009 | 62 | H-Arg-Arg-Nal-Cys-Tyr-Arg-Lys-DLys-Pro-Ala-Arg-Cit-Cys-Arg-OH |
| TA14010 | 63 | H-Arg-Arg-Nal-Cys-Tyr-Arg-Lys-DLys-Pro-Tyr-Ala-Cit-Cys-Arg-OH |
| TC14001 | 64 | H-Cit-Arg-Nal-Cys-Tyr-Arg-Lys-DLys-Pro-Tyr-Arg-Cit-Cys-Arg-OH |
| TC14003 | 65 | H-Arg-Arg-Nal-Cys-Tyr-Cit-Lys-DLys-Pro-Tyr-Arg-Cit-Cys-Arg-OH |
| TN14003 | 66 | H-Arg-Arg-Nal-Cys-Tyr-Cit-Lys-DLys-Pro-Tyr-Arg-Cit-Cys-Arg-NH$_2$ |
| TC14004 | 67 | H-Arg-Arg-Nal-Cys-Tyr-Arg-Cit-DLys-Pro-Tyr-Arg-Cit-Cys-Arg-OH |
| TC14012 | 68 | H-Arg-Arg-Nal-Cys-Tyr-Cit-Lys-DCit-Pro-Tyr-Arg-Cit-Cys-Arg-NH$_2$ |
| T-140 | 69 | H-Arg-Arg-Nal-Cys-Tyr-Arg-Lys-DLys-Pro-Tyr-Arg-Cit-Cys-Arg-OH |
| TC14011 | 70 | H-Arg-Arg-Nal-Cys-Tyr-Cit-Lys-DCit-Pro-Tyr-Arg-Cit-Cys-Arg-OH |
| TC14005 | 71 | H-Arg-Arg-Nal-Cys-Tyr-Arg-Lys-DCit-Pro-Tyr-Arg-Cit-Cys-Arg-OH |
| TC14018 | 72 | H-Cit-Arg-Nal-Cys-Tyr-Arg-Lys-DCit-Pro-Tyr-Arg-Cit-Cys-Arg-NH$_2$ |

In each one of SEQ ID NOS:1-72, two cysteine residues are preferably coupled in a disulfide bond.

Currently preferred peptides according to the present invention are peptides having an amino acid sequence as set forth in any one of SEQ ID NOS:1-72. More preferably, it has been previously reported that the T-140 derivatives having an amino acid sequence as set forth in any one of SEQ ID NOS: 1-68 and 70-71 presented in Table 1 may have improved stability in serum and reduced cytotoxicity relative to T-140 (SEQ ID NO:69). However, T-140 may be suitable for use in the methods of the present invention, e.g. when applied by local administration routes.

In another preferable embodiment, the peptide used in the compositions and methods of the invention consists essentially of an amino acid sequence as set forth in SEQ ID NO: 1. In another preferable embodiment, the peptide used in the compositions and methods of the invention is of an amino acid sequence as set forth in SEQ ID NO:1. In another embodiment, the peptide is at least 60%, preferably at least 70% and more preferably at least 80% homologous to SEQ ID NO:1. In another embodiment, the peptide is at least about 90% homologous to SEQ ID NO:1. In another embodiment, the peptide is at least homologous to SEQ ID NO:1. In another embodiment, the peptide is at least about 95% homologous to SEQ ID NO:1. Each possibility represents a separate embodiment of the present invention.

In various other particular embodiments, the peptide is selected from SEQ ID NOS:1-72, wherein each possibility represents a separate embodiment of the present invention.

In another particular embodiment, said peptide has an amino acid sequence as set forth in any one of SEQ ID NOS:1-4, 10, 46, 47, 51-56, 65, 66, 68, 70 and 71. In another particular embodiment, said peptide has an amino acid sequence as set forth in any one of SEQ ID NOS:4, 10, 46, 47, 68 and 70. In another particular embodiment, said peptide has an amino acid sequence as set forth in any one of SEQ ID NOS:1, 2, 51, 65 and 66. In another particular embodiment, said peptide has an amino acid sequence as set forth in any one of SEQ ID NOS:53-56.

In a preferable particular embodiment, said peptide has an amino acid sequence as set forth in SEQ ID NO: 1. In another particular embodiment, said peptide has an amino acid sequence as set forth in SEQ ID NO:2. In another particular embodiment, said peptide has an amino acid sequence as set forth in SEQ ID NO:51. In another particular embodiment, said peptide has an amino acid sequence as set forth in SEQ ID NO:66.

In another aspect, the invention relates to the use of a pharmaceutical composition comprising a peptide indicated by the following formula (II) or a salt thereof:

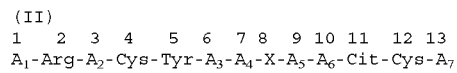

wherein:

$A_1$ represents a hydrogen atom, or an arginine, lysine, ornithine, citrulline or alanine residue or a N-α-substituted derivative of these amino acids;

$A_2$ represents an aromatic amino acid residue;

$A_3$, $A_4$ and $A_6$ each independently represent an arginine, lysine, ornithine, citrulline or alanine residue;

$A_5$ represents a tyrosine, phenylalanine, alanine, naphthylalanine or citrulline residue;

$A_7$ represents a lysine or arginine residue in which a carboxyl group may be amidated or esterified;

X is selected from the group consisting of:

(i) a peptide residue represented by the following formula (III):

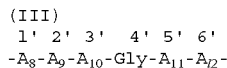

wherein $A_8$ and $A_{12}$ each independently represents an alanine, valine, leucine, isoleucine, serine, cysteine or methionine residue;

$A_9$ represents an aromatic amino acid residue, $A_{10}$ is selected from the same amino acid residues as in $A_3$, $A_{11}$ represents a tyrosine, phenylalanine, tryptophan, alanine, valine, leucine, isoleucine, serine, cysteine or methionine residue, provided that when both of the 1'-position and the 6'-position are cysteine residues, they may be bonded in a disulfide bond, (ii) a peptide selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group, and the peptide residues of (i) and (ii) represent a peptide residue which binds amino acid residues at the 7-position and the 9-position through a peptide bond;

and the cysteine residues at the 4-position and the 12-position may be bonded in a disulfide bond;

provided that, in the above polypeptide or a salt thereof, either of the amino acid residues of $A_1$, $A_3$, $A_4$, $A_5$, $A_6$ and $A_7$ is an alanine or citrulline residue; or (iii) a peptide residue containing a D-citrulline, D-alanine, citrulline, or alanine residue) or a salt thereof.

In the polypeptides of the formula (II) of the present invention, $A_1$ is preferably an arginine, alanine or citrulline residue; $A_2$ is preferably a tryptophan or naphthylalanine residue; $A_3$ is preferably arginine, alanine or citrulline residue; $A_4$ is preferably a lysine, alanine or citrulline residue; X is preferably a D-lysyl-proline, D-alanyl-proline, D-lysyl-alanine or D-citrullyl-proline residue; $A_5$ is preferably a tyrosine or alanine residue; $A_6$ is preferably an arginine, alanine or citrulline residue; $A_7$ is preferably an arginine residue.

Exemplary peptides of the formula (II) are peptides wherein $A_1$, $A_6$ and $A_7$ are arginine residues, $A_2$ is a naphthylalanine residue, $A_3$ is a citrulline residue, $A_4$ is a lysine residue, X is a D-lysyl-proline residue, and $A_5$ is a tyrosine residue, a polypeptide of the formula (II) wherein $A_1$, $A_3$, $A_6$ and $A_7$ are arginine residues, $A_2$ is a naphthylalanine residue, $A_4$ is a lysine residue, X is a D-citrullyl-proline residue, and $A_5$ is a tyrosine residue, a polypeptide of the formula (II) wherein $A_1$, $A_6$ and $A_7$ are arginine residues, $A_2$ is a naphthylalanine residue, $A_3$ is a citrulline residue, $A_4$ is a lysine residue, X is a D-citrullyl-proline residue, $A_5$ is a tyrosine residue, and a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-citrullyl-proline residue, $A_5$ is a tyrosine residue.

The peptides of formula (II) may be exemplified in another embodiment by a peptide of the formula (II) wherein $A_1$, $A_6$ and $A_7$ are arginine residues, $A_2$ is a naphthylalanine residue, $A_3$ is a alanine residue, $A_4$ is a lysine residue, X is a D-lysyl-proline residue, and $A_5$ is a tyrosine residue, a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-lysyl-proline residue, and $A_5$ is a tyrosine residue, a polypeptide of the formula (II) wherein $A_1$, $A_3$ and $A_7$ are arginine residues, $A_2$ is a naphthylalanine residue, $A_4$ is a lysine residue, X is a D-lysyl-proline residue, $A_5$ is a tyrosine residue, and $A_6$ is a citrulline residue, a polypeptide of the formula (II) wherein $A_1$ and $A_3$ are citrulline residues, $A_2$ is a naphthylalanine residue, $A_4$ is a lysine residue, X is a D-lysyl-proline residue, $A_5$ is a tyrosine residue, $A_6$ and $A_7$ are arginine residues, and a polypeptide of the formula (II) wherein $A_1$, $A_3$ and $A_7$ are arginine residues, $A_2$ is a naphthylalanine residue, $A_4$ is a lysine residue, X is a D-citrullyl-proline residue, $A_5$ is a tyrosine residue, and $A_6$ is a citrulline residue.

The amino acid of $A_7$ as presented in formula II herein is preferably one in which the carboxyl group is amidated for improving stability of the polypeptide in vivo such as in serum, etc.

A peptide of the present invention includes a peptide or its amide, ester or salt containing the amino acid sequence which is substantially the same amino acid sequence as the sequence of any of the above-mentioned peptides. Here, "substantially the same amino acid sequence" means an amino acid sequence that is qualitatively identical in the activity of the peptide or the biological activity of the peptide (e.g. MIP3α secretion) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (I), (II) and SEQ ID NOS:1-72 can have variances, so far as they have any of the above-mentioned properties. That is to say, in the present invention, any peptide (variant peptide) resulting from the variance in the amino acid sequence such as substitution, deletion or insertion (addition) etc. which brings about any significant change (i.e. a qualitatively different change, or a qualitatively identical but quantitatively significantly different change) in the physiological property or chemical property of the original (non-variant) peptide is deemed as substantially the same as the original (non-variant) peptide having no such variance, and, the amino acid sequence of such variant peptide is deemed as substantially the same as the amino acid sequence of the original (non-variant) peptide.

It is a well-known fact that generally, the changes such as substitution, deletion or insertion (addition) of an amino acid in a peptide sequence often do not make a significant change to physiological properties or chemical properties of such peptide. For example, it is generally considered that substitution of a certain amino acid by another amino acid of similar chemical properties results in a peptide having minimized deviation from the properties of the original peptide.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) basic amino acids carrying positive electric charge (examples: arginine, lysine, histidine, etc.); (iv) acidic amino acids carrying negative electric charge (examples: aspartatic acid, glutamic acid, etc.), and accordingly, amino acid substitution within each class can be conservative with regard to the property of a peptide (namely, substitution generating "substantially same" amino acid sequences).

In other words, "substantially the same amino acid sequences" may include:

(i) amino acid sequences wherein 1 or more, or, in other embodiments, 1 to 3 amino acids were substituted by other amino acids in the amino acid sequences indicated in the above-mentioned formula (I), (II) and SEQ ID NOS:1-72;

(ii) amino acid sequences wherein 1 or more, or, in other embodiments, 1 to 3 amino acids were deleted in the amino acid sequences indicated in the above-mentioned formula (I), (II) and SEQ ID NOS:1-72;

(iii) amino acid sequences wherein 1 or more or, in other embodiments, 1 to 3 amino acids were added (inserted) in the amino acid sequences indicated in the above-mentioned formula (I), (II) and SEQ ID NOS:1-72; or (iv) peptides including modifications to amino acids (particularly, the side chains thereof) among the peptides having the amino acid sequences indicated in above (i), (ii) or (iii), or esters, amides or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced activity. The peptides of the present invention include also these variant peptides or amides thereof, esters thereof or salts thereof.

Furthermore, among the peptides of the present invention are the peptide consisting of the amino acid sequence indicated in any of the above-mentioned formula (I), (II) and SEQ ID NOS:1-72, and the peptide containing the amino acid sequence sharing the homology of about 50 to 99.9% (preferably, 70 to 99.9%, more preferably 90 to 99.9%) with the foregoing amino acid sequence and having the activities of substantially the same nature as the peptide consisting of the amino acid sequence indicated in any of the above-mentioned formula (I), (II) and SEQ ID NOS:1-72, or amides thereof, esters thereof or salts thereof.

The amides, esters or salts of the peptide having the amino acid sequence indicated in any of the above-mentioned SEQ ID NOS:1-72 include the same ones as are exemplified for the peptide indicated in the above-mentioned formula (I). Preferably, the peptide having the amino acid sequence indicated in any of the above-mentioned SEQ ID NOS:1-72 is amidated at the carboxyl group of the C-terminal amino acid residue.

The peptides of the present invention including the peptide containing the amino acid sequence indicated in any of the above-mentioned SEQ ID NOS:1-72 can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:

(1) Bodanszky and Ondetti, *Peptide Synthesis*, Interscience Publishers, New York (1966).

(2) Schroeder and Luebke, *The Peptide*, Academic Press, New York (1965).

(3) Izumiya et al., *Peptide Synthesis*, Basics and Practice, Maruzen, Tokyo (1975).

(4) Yajima et al., *Protein Chemistry IV*, Tokyo Kagakudojin, Tokyo, pp. 205 (1977).

(5) Yajima and Zoku-Iyakuhin-no-Kaihatsu, *Peptide Synthesis*, Hirokawa Publishing Co., Tokyo, Vol. 14 (1991).

As practical methods for syntheses of peptides, the following examples can be given:

Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl) phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with, conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but it is particularly better to use carboxyimides. Among such carboxyimides are DCC, N,N'-diisopropylcarbodiimide, N-ethyl-N'-(3-dimethylaminopropyl)cabodiimde, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoing are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl—Z, Br—Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorbenzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this eterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, Cl2-Bzl, 2-nitrobenzyl, Br—Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBt] are used. Ingredients with activated amino group include, for example, corresponding phosphoric amide. As the methods to remove (eliminate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc., base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxy-terminal amino acid and then extending the peptide chain to the desired chain length on the side of amino group, a polypeptide eliminating the protective group of α-amino group of N-terminal of such peptide chain and a polypeptide eliminating the protective group of carboxyl group of C-terminal, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

Pharmaceutical Compositions and Kits

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philadelphia, Pa., $20^{th}$ ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient (e.g. intralesional injection).

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum, tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein.

In yet another aspect, there is provided a pharmaceutical composition comprising as active ingredients a peptide having an amino acid sequence as set forth in SEQ ID NO:1 or an analog or derivative thereof and rapamycin or a derivative thereof.

In another aspect, there is provided a kit comprising i) a peptide having an amino acid sequence as set forth in SEQ ID NO:1 or an analog or derivative thereof and ii) a chemotherapeutic agent comprising rapamycin or a derivative thereof.

In one embodiment, there is provided a pharmaceutical pack containing a course of anti-neoplastic treatment for one individual mammal comprising a container having a unit of a T-140 analog of the invention in unit dosage form, and a container having a unit of rapamycin.

In some embodiments, the combinations of the invention are provided in packs in a form ready for administration. In other embodiments, the combinations of the invention are provided in concentrated form in packs, optionally with the diluent required to make final solution(s) for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

In a particular embodiment, the kits further comprise instructions for administering said peptide and said chemotherapeutic agent to a subject afflicted with cancer, particularly with a tumor of hematopoietic or glial origin, as detailed herein.

Rapamycin, or sirolimus, is an immunosuppressive agent. Sirolimus is a macrocyclic lactone produced by *Streptomyces hygroscopicus*. The chemical name of sirolimus is (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29 (4H,6H,31H)-pentone. Its molecular formula is $C_{51}H_{79}NO_{13}$ and its molecular weight is 914.2. The structural formula of sirolimus is shown below:

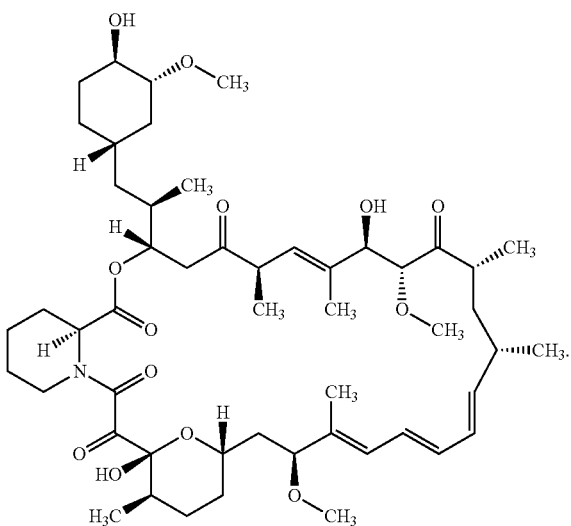

As defined herein, the term "rapamycin" defines a class of immunosuppressive compounds which contain the basic rapamycin nucleus (shown above). The rapamycins of this invention include compounds which may be chemically or biologically modified as derivatives of the rapamycin nucleus, while still retaining immunosuppressive properties. Accordingly, the term "rapamycin" includes esters, ethers, oximes, hydrazones, and hydroxylamines of rapamycin, as well as rapamycins in which functional groups on the rapamycin nucleus have been modified, for example through reduction or oxidation. The term "rapamycin" also includes pharmaceutically acceptable salts of rapamycins, which are capable of forming such salts, either by virtue of containing an acidic or basic moiety.

Rapamycin is currently available as RAPAMUNE® (Wyeth-Ayerst) Oral Solution and Tablets, indicated for the prophylaxis of organ rejection in patients receiving renal transplants.

Therapeutic Uses

In another aspect, the invention provides a method for treating a subject afflicted with a tumor selected from the group consisting of multiple myeloma and glioma, comprising administering to the subject a therapeutically effective amount of a peptide having an amino acid sequence as set forth in SEQ ID NO:1 or an analog or derivative thereof.

The invention is further directed to a method for inducing hematopoietic tumor cell death in a subject in need thereof, comprising administering to the subject a therapeutically effective amount of a peptide having an amino acid sequence as set forth in SEQ ID NO:1 or an analog or derivative thereof.

In one particular embodiment, the tumor is multiple myeloma. In another particular embodiment, the tumor is microglioma.

The invention is further directed to a method for inducing glial tumor cell death in a subject in need thereof, comprising administering to the subject a therapeutically effective amount of a peptide having an amino acid sequence as set forth in SEQ ID NO:1 or an analog or derivative thereof.

In one embodiment, the tumor is glioma.

In another aspect, there is provided a method for increasing the sensitivity of tumor cells to an anti-cancer agent in a subject in need thereof comprising administering to the subject a sensitizing-effective amount of a peptide having an amino acid sequence as set forth in SEQ ID NO:1 or an analog or derivative thereof in concurrent or sequential combination with the anti-cancer agent.

In another embodiment, the anti-cancer agent is a chemotherapeutic drug. Various chemotherapeutic drugs are known in the art, for example alkylators including, but not limited to, busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), and temozolamide (Temodar); anthracyclines, including, but not limited to doxorubicin (Adriamycin, Doxil, Rubex), mitoxantrone (Novantrone), idarubicin (Idamycin), valrubicin (Valstar), and epirubicin (Ellence); antibiotics, including, but not limited to, dactinomycin, actinomycin D (Cosmegen), bleomycin (Blenoxane), daunorubicin, and daunomycin (Cerubidine, DanuoXome); aromatase inhibitors, including, but not limited to anastrozole (Arimidex) and letroazole (Femara); bisphosphonates, including, but not limited to zoledronate (Zometa); cyclooxygenase inhibitors, including, but not limited to, celecoxib (Celebrex); estrogen receptor modulators including, but not limited to tamoxifen (Nolvadex) and fulvestrant (Faslodex); folate antagonists including, but not limited to methotrexate and tremetrexate; inorganic aresenates including, but not limited to arsenic trioxide (Trisenox); microtubule inhibitors (e.g. taxanes) including, but not limited to vincristine (Oncovin), vinblastine (Velban), paclitaxel (Taxol, Paxene), vinorelbine (Navelbine), epothilone B or D or a derivative of either, and discodermolide or its derivatives, nitrosoureas including, but not limited to procarbazine (Matulane), lomustine, CCNU (CeeBU), carmustine (BCNU, BiCNU, Gliadel Wafer), and estramustine (Emcyt); nucleoside analogs including, but not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), pentostatin (Nipent), cladribine (Leustatin, 2-CdA), gemcitabine (Gemzar), and capecitabine (Xeloda); osteoclast inhibitors including, but not limited to pamidronate (Aredia); platinum containing compounds including, but not limited to cisplatin (Platinol) and carboplatin (Paraplatin); retinoids including, but not limited to tretinoin, ATRA (Vesanoid), alitretinoin (Panretin), and bexarotene (Targretin); topoisomerase 1 inhibitors including, but not limited to topotecan (Hycamtin) and irinotecan (Camptostar); topoisomerase 2 inhibitors including, but not limited to etoposide, VP-16 (Vepesid), teniposide, VM-26 (Vumon), and etoposide phosphate (Etopophos); and tyrosine kinase inhibitors including, but not limited to imatinib (Gleevec).

For example, the following agents are used in the treatment of hematopoietic tumors such as lymphomas, and may be used in combination with the T-140 analogs of the invention:

DNA-Altering Drugs (Alkylating Agents)

These drugs change DNA, the building block of cells, to prevent cell growth, e.g. Bendamustine, Carboplatin (Paraplatin®), Carmustine (BCNU®), Chlorambucil (Leukeran®), Cisplatin (Platinol®), Cyclophosphamide injection (Cytoxan®), Cyclophosphamide oral (Cytoxan®), Dacarbazine (DTIC®), Ifosfamide (Ifex®), Lomustine (CCNU®), Mechlorethamine (nitrogen mustard, Mustargen®), Melphalan (Alkeran®) and Procarbazine (Matulane®).

Anti-Tumor Antibiotics

These drugs interact with DNA and decrease cell survival, e.g. Bleomycin (Blenoxane®), Doxorubicin (Adriamycin®, Rubex®), Doxorubicin, Liposomal (Doxil), Idarubicin (Idamycin®) and Mitoxantrone (Novantrone®).

Antimetabolites

These drugs interfere with normal cell growth, e.g. Chlorodeoxyadenosine (Cladribine®, also known as 2-chlorodeoxyadenosine; 2-CdA), Cytarabine IV (cytosine arabinoside, Ara-C, Cytosar), Fludarabine IV (Fludara®), Fludarabine oral (Fludara®), Gemcitabine (Gemzar®), Mercaptopurine oral (Purinethol®), Methotrexate oral (Rheumatrex®) Other name: amethopterin, Pentostatin IV (Nipent®) and Thioguanine oral (Lanvis®).

DNA Repair Enzyme Inhibitors

These drugs act on certain proteins (enzymes) that normally work to repair faulty DNA and therefore make cells more likely to die when they are injured, e.g. Etoposide oral (VP-16, VePesid®, Etopophos) and Etoposide IV (VP-16, VePesid®, Etopophos).

Microtubule Inhibitors

These drugs damage cell structures required for cells to divide, e.g. Vinblastine (Velban®), Vincristine (Oncovin®) and Vinorelbine (Navelbine®).

Steroidal (Corticosteroids)

Corticosteroids, including Prednisone, Prednisolone, Methylprednisolone and Dexamethasoneare are a group of synthetic hormones closely related to cortisol (a glucocorticoid), a natural hormone produced in the adrenal cortex.

Prednisone decreases inflammation by preventing white blood cells from functioning properly. More specifically, the drug interferes with lymphocytes (one of several types of white blood cells). The presence of white blood cells result in inflammation (for many reasons, damage to tissue, fungus, virus, bacteria, allergens and almost any foreign invader)—they go to a site and their presence inflames the area. Prednisone causes lymphocytes to break apart and die.

Examples: Dexamethasone (Decadron®), Methylprednisolone (Medrol®) and Prednisone (Deltasone®).

It should be understood, that the T-140 peptides of the invention may be administered to augment the anti-cancer effect of a chemotherapeutic drug, as well as of a combination of drugs. In another particular example, treating transformed indolent, or aggressive lymphomas that express CD20 may be performed by administering a T-140 analog of the invention in combination with the following drugs: Cyclophosphamide (Cytoxan®) Doxorubicin (Adriamycin®) Vincristine (Oncovin®) Prednisone (Deltasone®) (collectively known as CHOP chemotherapy) and optionally Rituxan® (an anti-CD20 monoclonal antibody, also known as rituximab).

Suitable dosages and administration routes of chemotherapeutic drugs are readily determined by the skilled artisan.

In another particular embodiment wherein the drug is rapamycin or a derivative thereof.

In another embodiment, the tumor is a hematopoietic tumor. In a particular embodiment, said tumor is multiple myeloma. In another particular embodiment, said tumor is microglioma. In another particular embodiment, said tumor is glioma.

In various embodiments of the present invention, the subject is selected from humans and non-human mammals. In a preferable embodiment, the subject is human.

In another aspect, the invention is directed to the use of a pharmaceutical composition comprising a peptide having an amino acid sequence as set forth in SEQ ID NO:1 or an analog or derivative thereof and optionally a chemotherapeutic drug (e.g. rapamycin), for the preparation of a medicament for treating a subject having a tumor selected from the group consisting of multiple myeloma, microglioma and glioma, for inducing hematopoietic tumor cell death, for inducing glial tumor cell death, and/or for increasing the sensitivity of tumor cells to an anti-cancer agent.

In another aspect, the invention is directed to a pharmaceutical composition comprising a peptide having an amino acid sequence as set forth in SEQ ID NO:1 or an analog or derivative thereof and optionally a chemotherapeutic drug (e.g. rapamycin) for treating a subject having a tumor selected from the group consisting of multiple myeloma, microglioma and glioma, for inducing hematopoietic tumor cell death, for inducing glial tumor cell death, and/or for increasing the sensitivity of tumor cells to an anti-cancer agent.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans. An exemplary dosage range for human use may be from about 0.05 to about 10 mg/kg per administration (e.g. subcutaneously, once or twice a day).

The following examples are presented in order to more fully illustrate some embodiments of the invention. They should, in no way be construed, however, as limiting the broad scope of the invention.

EXAMPLES

Reagents

AMD3100 was purchased from Sigma, Israel. 4F-benzoyl-TN14003 (SEQ ID NO:1) was synthesized by Novotide Ltd. In order to neutralize the activity of 4F-benzoyl-TN14003 in some experiments proteinase K was used as followed: 4F-benzoyl-TN14003 was incubated with Proteinase K (Dako, 1 mg/ml) for 20 min at 37° C. following by 10 min incubation at 95° C.

The label "4FB-TN14003" as it appears throughout the figures, is used to indicate 4F-benzoyl-TN14003 (SEQ ID NO:1).

Example 1

4F-Benzoyl-TN14003 Induces MIP3α Secretion from Prostate Cell Lines in a CXCR4 Agonist Manner A PC3 prostate cell line that overexpresses high levels of CXCR4 was generated. Single cell clones were generated from this PC3-CXCR4 cell line, and one of the clones (PC3-CXCR4.5), which showed a high and stable expression level of CXCR4, was selected for the experiments. FIG. 1A presents FACS histograms of PC3 cells (left panel) and a single cell clone with stable overexpression of CXCR4, GFP and luc genes (PC3-CXCR4.5, right panel) that were stained for the control (IgG2a-PE, full histograms) and CXCR4 (IgG2a-12G5, empty histograms) antibodies.

Figure 1B:
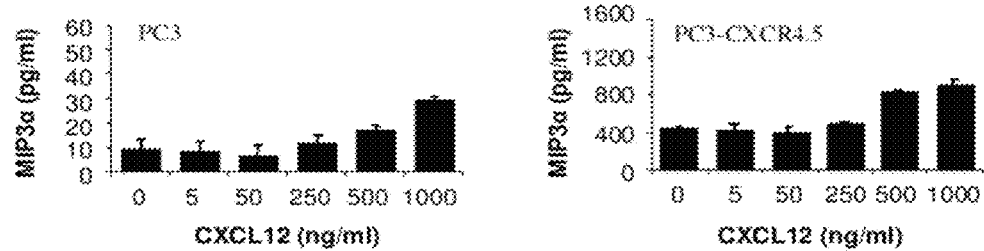
FIG. 1B illustrates MIP3α secretion, assessed by ELISA, of PC3 cells (left panel) and PC3-CXCR4.5 cells (right panel) stimulated with different concentrations of CXCL12 for 48 hours.

In this example, regulation of the chemokine MIP3α (macrophage inflammatory protein 3α) was examined. It was found that PC3-CXCR4.5 cells secreted higher levels of MIP3α than PC3 cells, and increasing doses of CXCL12 increased the secretion of MIP3α in both PC3 and PC3-CXCR4.5 cells (FIG. 1B). In FIG. 1B, PC3 (left panel) and PC3-CXCR4.5 (right panel) cells were stimulated with the indicated concentrations of CXCL12 for 48 hours and MIP3α secretion was assessed by ELISA. The results represent the average of triplicates±STDEV.

Figure 1C:
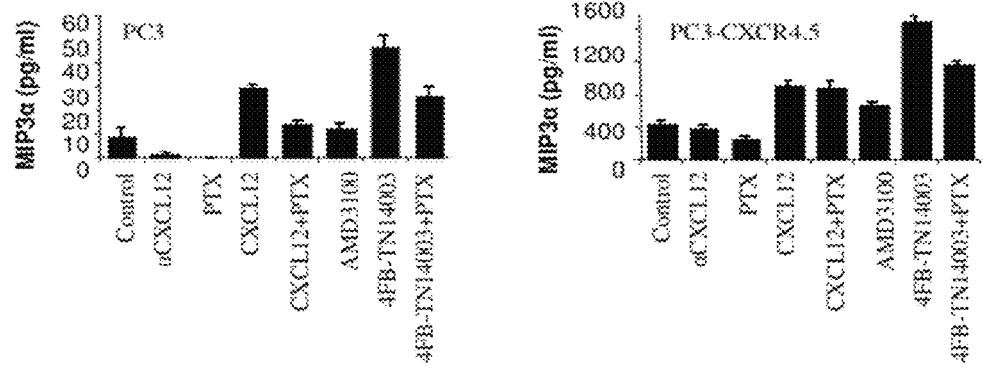
FIG. 1C illustrates MIP3α secretion, assessed by ELISA, of PC3 cells (left panel) and PC3-CXCR4.5 cells (right panel) treated with anti-CXCL12 antibodies, Pertussis toxin, AMD3100 or 4F-benzoyl-TN14003, alone or in combination with CXCL12.

In PC3 cells, treatment with neutralizing antibodies against CXCL12 (αCXCL12) or with Pertussis toxin (PTX; alone or in combination with CXCL12) effectively inhibited the secretion of MIP3α (FIG. 1C). In contrast, in PC3-CXCR4.5 cells, anti-CXCL12 antibodies did not quite affect the secretion level of MIP3α; with PTX treatment alone, secretion of MIP3α was decreased, but PTX in combination with CXCL12 did not demonstrate an inhibitory effect on the level of MIP3α (FIG. 1C). The effects of the CXCR4 antagonist AMD3100 and of 4F-benzoyl-TN14003 (4FB-TN14003), hitherto known as a CXCR4 antagonist, on MIP3α secretion were further tested. Surprisingly, 4F-benzoyl-TN14003, but not AMb3100 induced in both cell lines MIP3α secretion in an agonist manner (FIG. 1C). The effect of 4F-benzoyl-TN14003 was partially inhibited by PTX treatment in both cell lines (FIG. 1C). In FIG. 1C, CXCR4 signaling in PC3 (left panel) and PC3-CXCR4.5 (right panel) cells was inhibited with anti-CXCL12 antibodies (αCXCL12) and Pertussis toxin (PTX) treatments alone or in combination with CXCL12, as indicated. Secretion of MIP3α was assessed by ELISA. The results represent the average of triplicates±STDEV.

PC3-CXCR4.5 cells secreted higher levels of MIP3α than PC3 cells, and increasing doses of CXCL12 increased the secretion of MIP3α from these cells. Spontaneous secretion of MIP3α is CXCL12 and PTX independent in these cells. The spontaneous, CXCL12-induced and 4F-benzoyl-TN14003-induced secretion was found to be CXCR4 dependent, as determined by evaluation of CXCR4 and MIP3α expression following transfection with CXCR4-specific or control siRNA.

Example 2

Figure 2A:
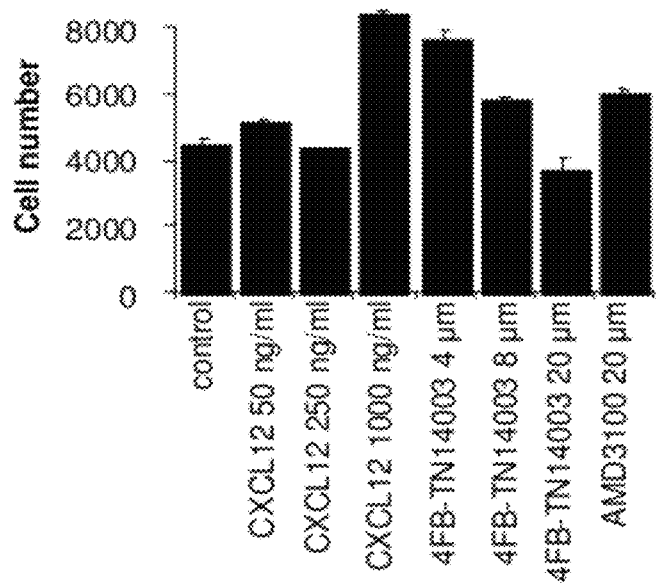
FIG. 2A, proliferation of human CD4+ T cells in response to increasing doses of CXCL12, or in response to the treatment with the CXCR4 antagonist AMD-3100 and 4F-benzoyl-TN14003.
Figure 2B:
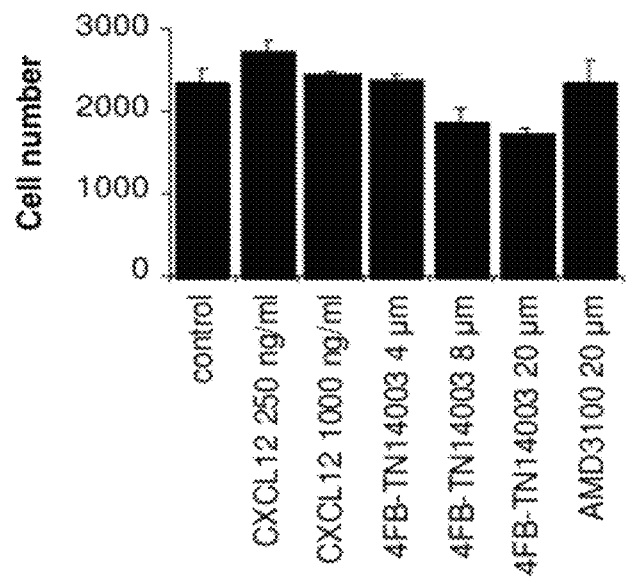
FIG. 2B, proliferation of human CD34+ hematopoietic stem cells.
Figure 2C:
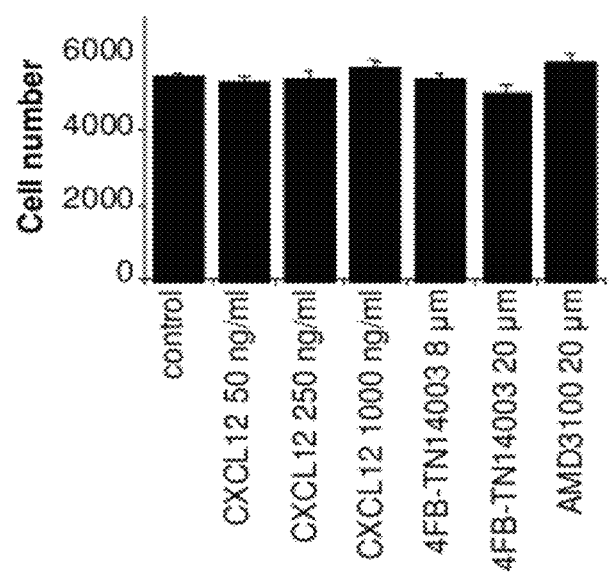
FIG. 2C, proliferation of human primary keratinocytes.

The Effect of 4F-Benzoyl-TN14003 and AMD-3100 on Cell Survival and Proliferation The effect of CXCR4 antagonists on the survival of freshly isolated normal $CD4^+$ T cells, $CD34^+$ stem cells and keratinocytes was examined. The proliferation and survival of keratinocytes was not inhibited by CXCR4 antagonists AMD-3100 (20 μM) and 4F-benzoyl-TN14003 (4-20 μM) or the natural ligand CXCL12 (FIG. 2C). The proliferation and survival of $CD4^+$ T cells was not inhibited by CXCR4 antagonists AMD-3100 (20 μM). However, both 4F-benzoyl-TN14003 (4-20 μM) and CXCL12, induced T cell proliferation (FIG. 2A). The proliferation and survival of $CD34^+$ stem cells was partially inhibited (−25%) by 4F-benzoyl-TN14003 (8, 20 μM), whereas, CXCL12 and AMD-3100 (20 μM) did not affect cell numbers (FIG. 2B). in FIG. 1, the results represent average of triplicates±STDEV.

Figure 3A:
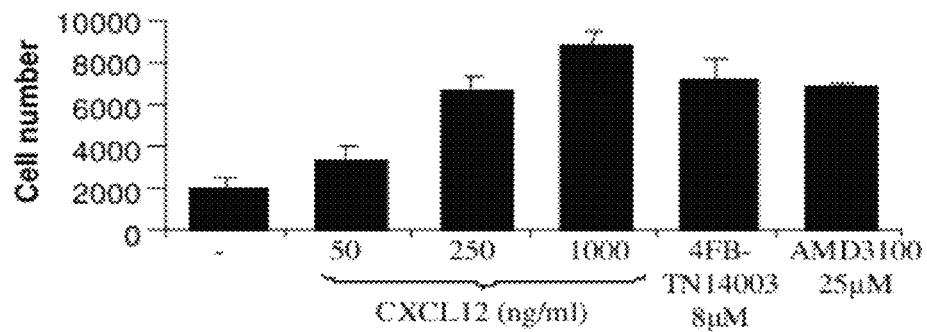
FIG. 3A, proliferation of PC3 cells in response to increasing doses of CXCL12, or in response to the treatment with a single dose of AMD-3100 and 4F-benzoyl-TN14003.
Figure 3B:
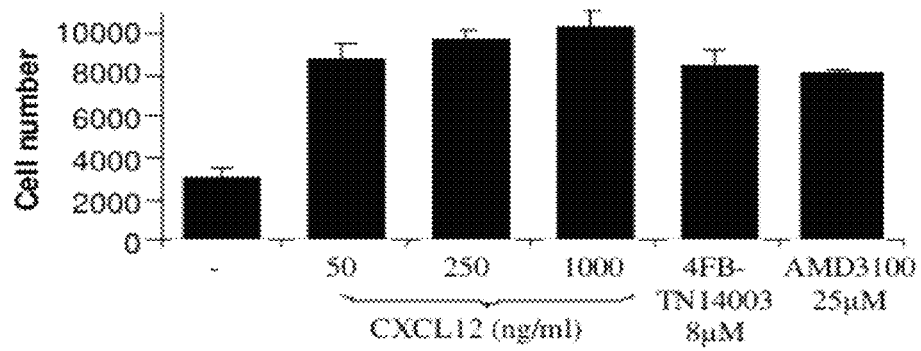
FIG. 3B, proliferation of PC3-CXCR4.5 cells in response to increasing doses of CXCL12, or in response to the treatment with a single dose of AMD-3100 and 4F-benzoyl-TN14003.
Figure 3C:
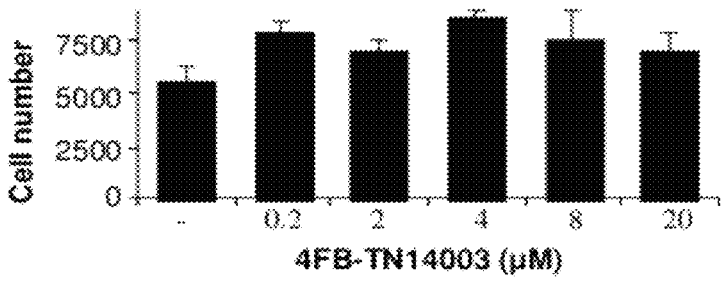
FIG. 3C, proliferation of PC3 cells in response to increasing doses of 4F-benzoyl-TN14003.
Figure 3D:
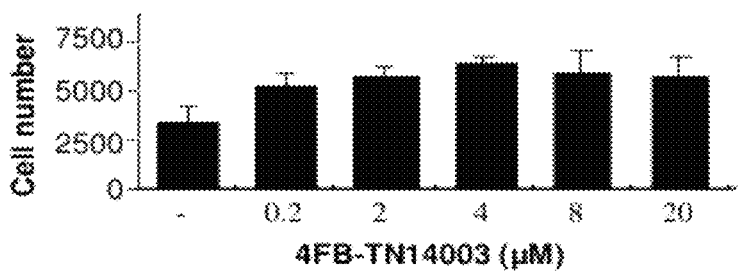
FIG. 3D, proliferation of PC3-CXCR4.5 cells in response to increasing doses of 4F-benzoyl-TN14003. The results represent average of triplicates ±STDEV.
Figure 4A:
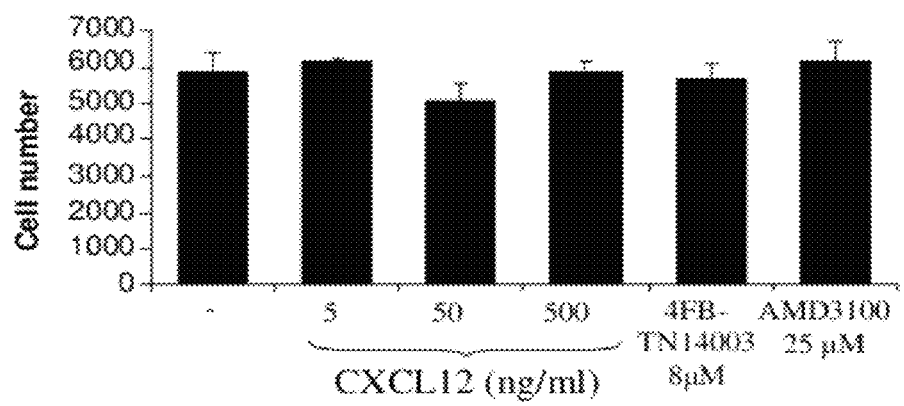
FIG. 4 demonstrates that cancer cell lines of epithelial origin, SKBR3 (breast carcinoma), U87 (glioblastoma) and 22RV1 (prostate carcinoma) do not demonstrate significant response in proliferation following stimulation with CXCL12, AMD-3100 or 4F-benzoyl-TN14003. Proliferation of cancer cell lines, SKBR3 (FIG. 4A), 22RV1 (FIG. 4B) and U87 (FIG. 4C), in response to increasing doses of CXCL12, or in response to the treatment with a single dose of CXCR4 antagonists, AMD-3100 and 4F-benzoyl-TN14003. The results represent average of triplicates±STDEV.
Figure 4B:
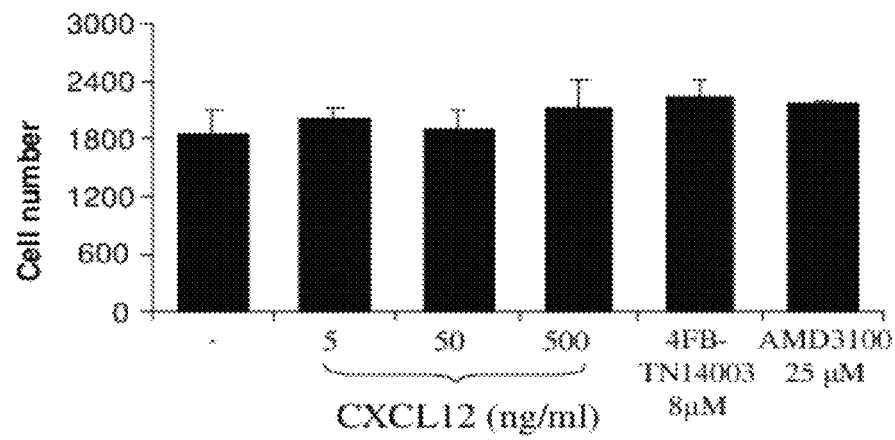
Figure 4C:
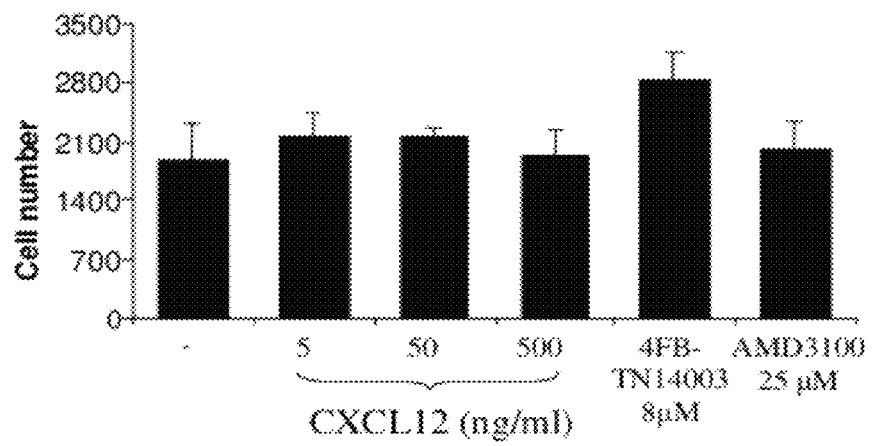

Next, the effect of the CXCR4 modulators on PC3 and PC3-CXCR4.5 prostate tumor cells was tested. Similarly to CXCL12, both AMD-3100 and 4F-benzoyl-TN14003 induced the proliferation of prostate cancer cells (FIG. 3A). The proliferation induced by 4F-benzoyl-TN14003 was dose-dependent (FIG. 3B). Other cell lines such as breast carcinoma, SKBR3, prostate carcinoma, 22Rv1, and glioblastoma, U-87, were either stimulated or not affected by CXCL12 and CXCR4 modulators AMD-3100 and 4F-benzoyl-TN14003 (FIGS. 4A-4C, respectively). These data suggest that 4F-benzoyl-TN14003 can increase proliferation of prostate cells PC3, and PC3-CXCR4.5 cells and can act as an agonist.

Overall, these results indicate that 4F-benzoyl-TN14003 does not induce epithelial tumor cell death and can in some cases stimulate growth of epithelial cells expressing CXCR4. CXCR4 is expressed on a majority of hematopoietic stem cells. Therefore the effect of CXCR4 antagonists on the survival and proliferation of a variety of blood borne hematopoietic tumor cell lines was tested.

Figure 5A:
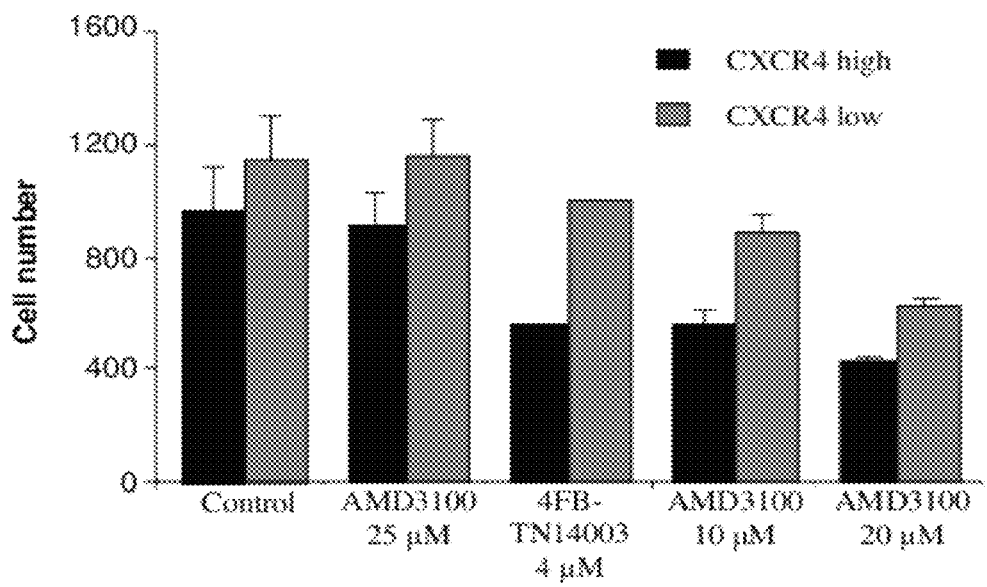
FIG. 5A, proliferation of human CML K562 cells that express low (gray columns) and high (black columns) levels of CXCR4 before (control) and after treatment with increasing doses of the CXCR4 antagonist AMD-3100 (25 µM) and 4F-benzoyl-TN14003 (4-20 µM). The results represent average of triplicates±STDEV.
Figure 5B:
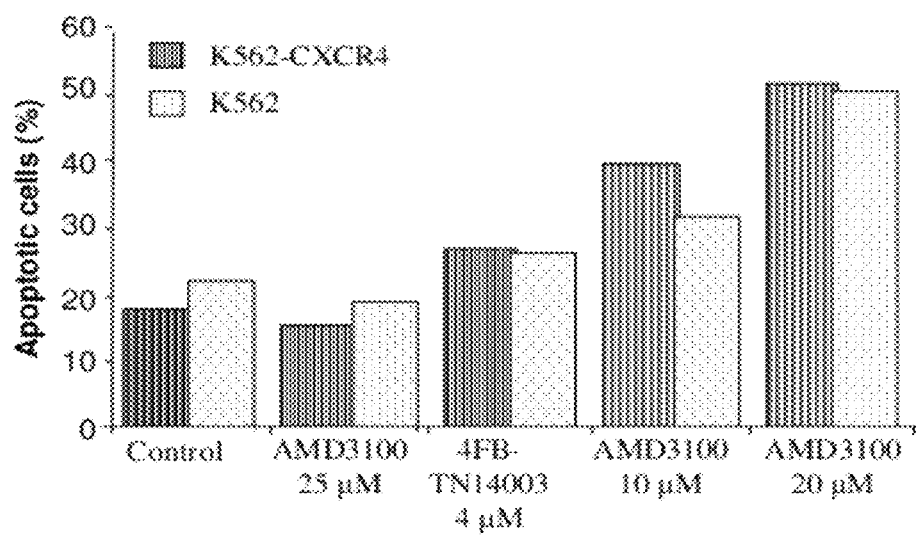
FIG. 5B, the percentage of apoptotic annexin positive cells determined by FACS of K562 cells or K562 cells overexpressing CXCR4 ("K562-CXCR4").

The proliferation and survival of the CML K562 cells or K562 cells that over-express CXCR4 (indicated "CXCR4 high" or "K562-CXCR4") was first studied. It was found that the CXCR4 modulator 4F-benzoyl-TN14003 (4-20 μM), but not AMD-3100, inhibited the growth and stimulated apoptotic cell death (measured by Annexin V assay in accordance with the manufacturer's recommendation; IQP, Groningen, Netherlands) of K562 cells that express low and high levels of CXCR4 (FIG. 5).

Figure 6A:
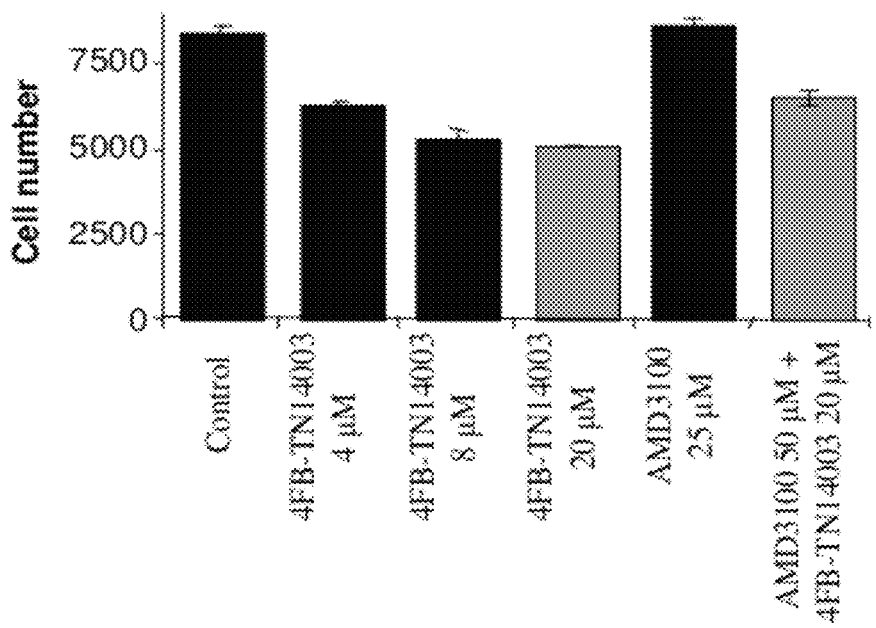
FIGS. 6A and 6C depict the results of different experiments measuring proliferation of human HL-60 cells before (control) and after treatment with increasing doses of the CXCR4 antagonist AMD-3100 (25 µM) and 4F-benzoyl-TN14003 (4-20 µM). The results represent average of triplicates±STDEV.
Figure 6B:
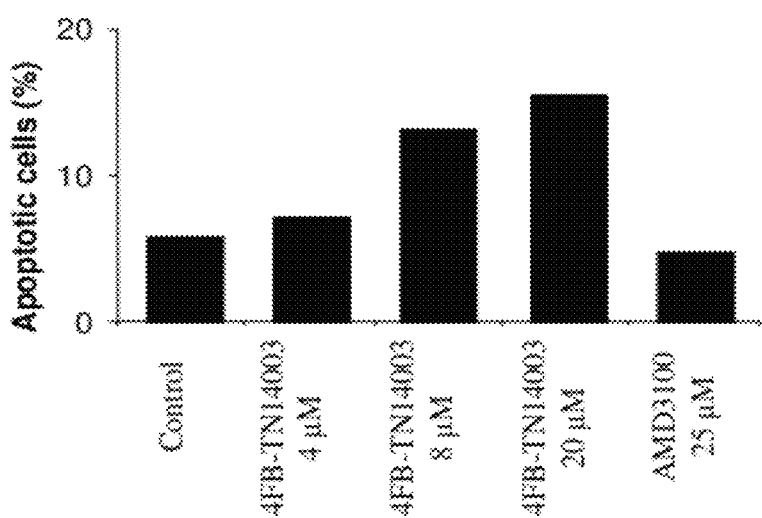
FIG. 6B, the percentage of apoptotic annexin positive cells determined by FACS. The effect of 4F-benzoyl-TN14003 on the survival of HL-60 and NB-4 cells can be inhibited by pretreatment of cells with the CXCR4 antagonist AMD-3100.
Figure 6C:
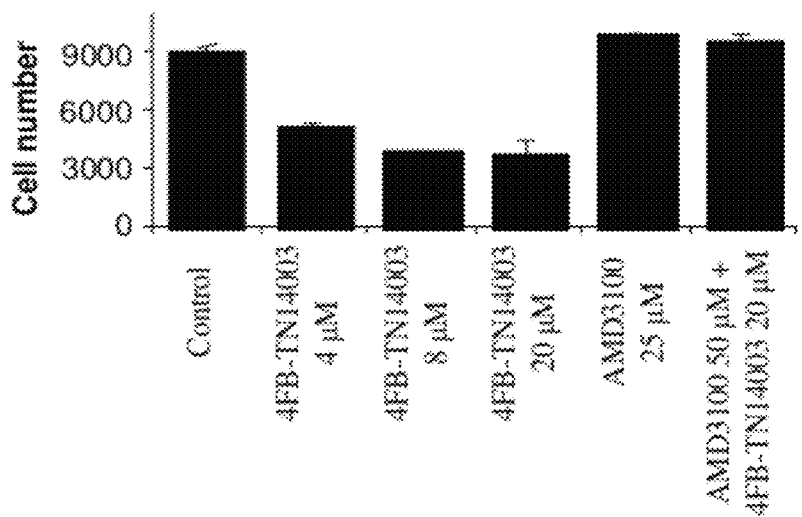
Figure 6D:
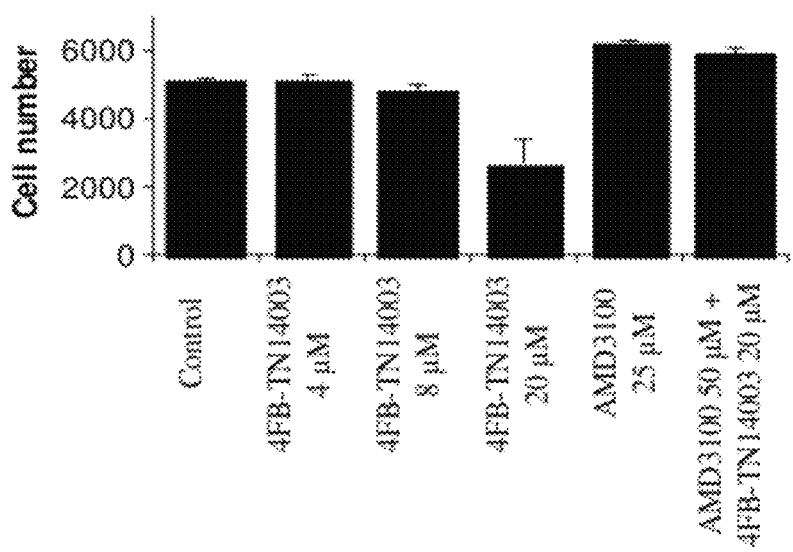
FIG. 6D, proliferation of human NB4 cells before and after treatment with increasing doses of the CXCR4 antagonist AMD-3100 (25 µM) and 4F-benzoyl-TN14003 (4-20 µM).
Figure 7A:
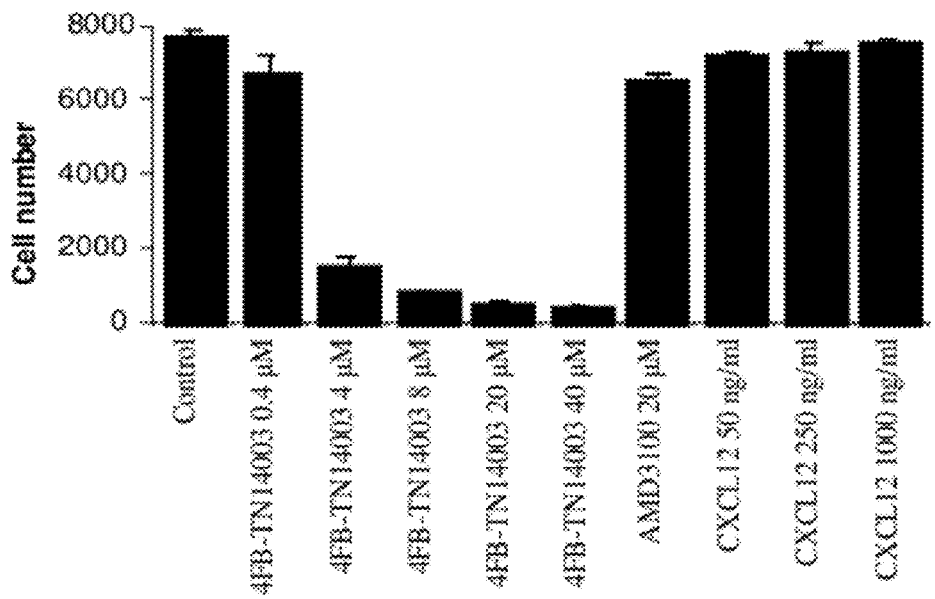
FIG. 7 depicts the Effect of 4F-benzoyl-TN14003 on the proliferation of RPMI8226, ARH77, U266, and NCI multiple myeloma (MM) cells. Proliferation of human RPMI8226 (FIG. 7A), ARH77 (FIG. 7C), U266 (FIG. 7E), NCI (FIG. 7G) MM cells before (control) and after treatment with increasing doses of the CXCR4 antagonists AMD-3100 (20 μM) and 4F-benzoyl-TN14003 4-20 μM). The results represent average of triplicates±STDEV. The percentage of apoptotic annexin positive cells was determined for each cell line by FACS (FIGS. 7B, 7D, 7F and 7H, respectively).
Figure 7B:
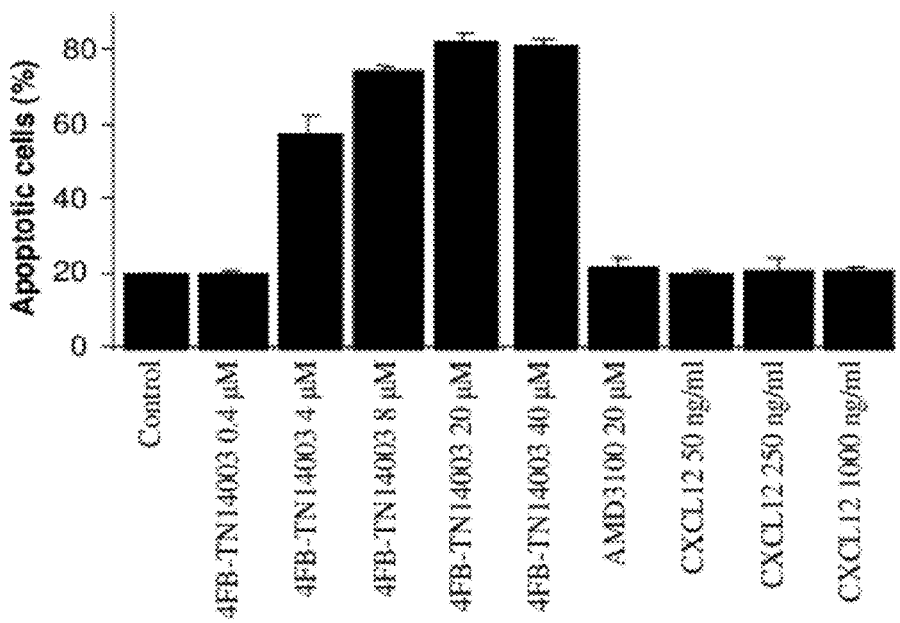
Figure 7C:
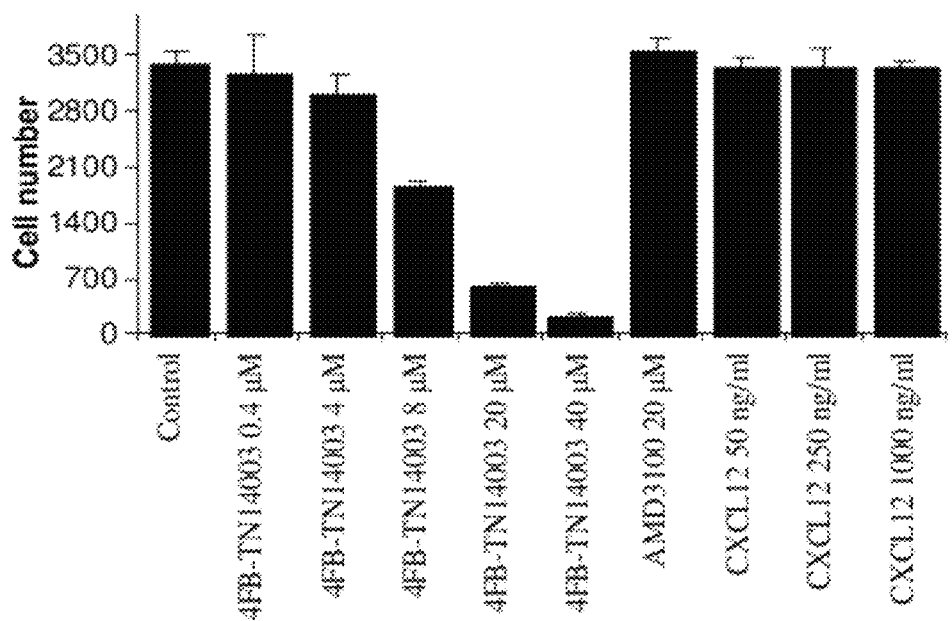
Figure 7D:
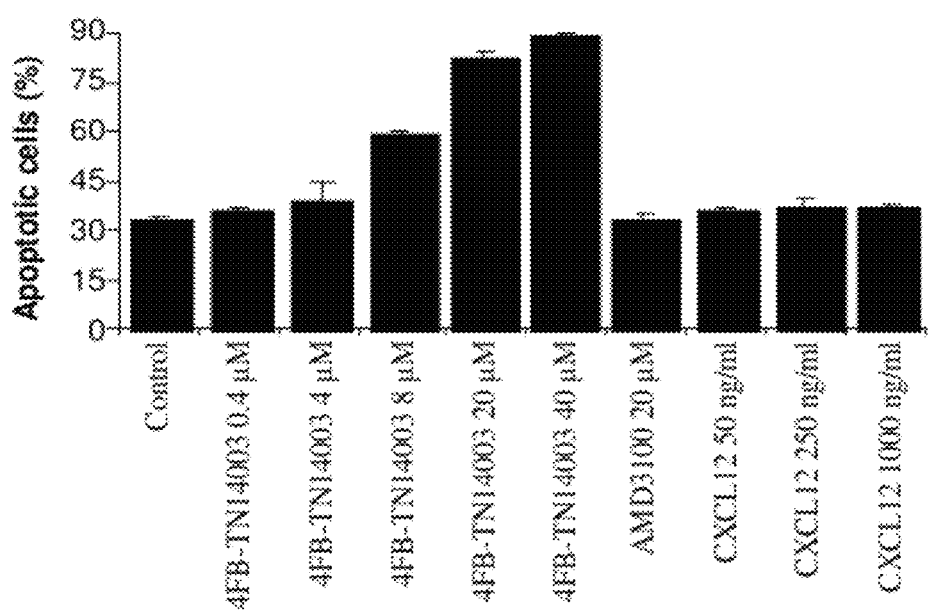
Figure 7E:
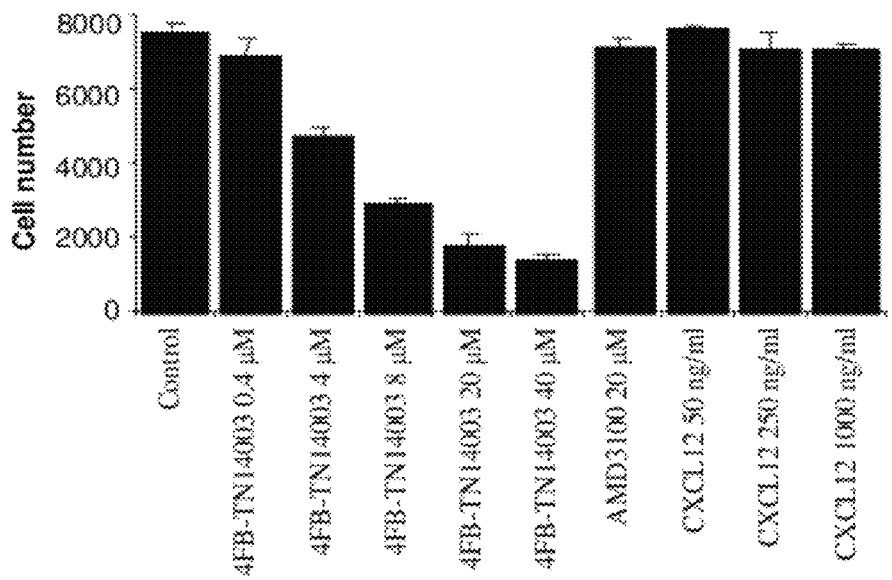
Figure 7F:
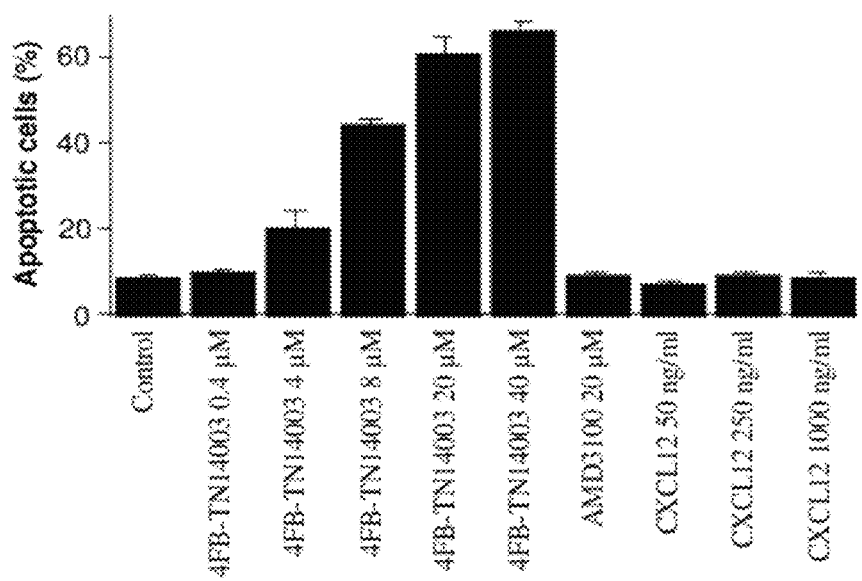
Figure 7G:
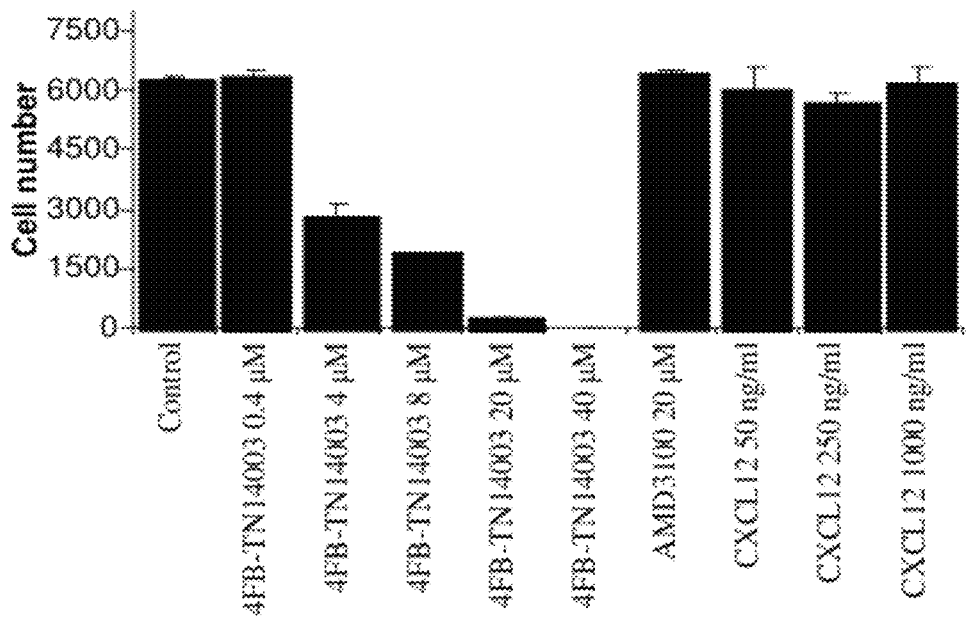
Figure 7H:
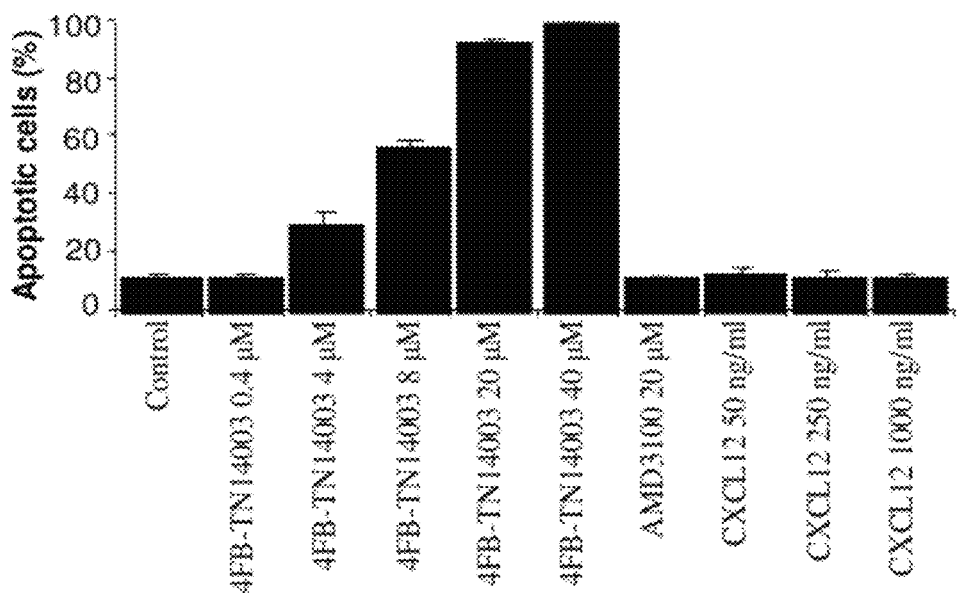

The inhibitory effect of 4F-benzoyl-TN14003 was further studied using the promyelocytic leukemic cell line HL-60 and the AML cell line NB4. The CXCR4 modulator 4F-benzoyl-TN14003 (4-20 μM), but not AMD-3100, was found to inhibit the growth and stimulate apoptotic cell death (measured by Annexin V assay) of HL-60 cells (FIGS. 6A and 6B, respectively). Pretreatment of HL-60 cells with AMD-3100 (50 μM) abolished the effect of 4F-benzoyl-TN14003 on these cells (FIGS. 6A and 6C depict two representative experiments). NB4 cells were less sensitive to 4F-benzoyl-TN14003 however; the inhibitory effect of 4F-benzoyl-TN14003 on NB4 cells was abolished by pretreatment with AMD-3100 (FIG. 6D).

The inhibitory effect of 4F-benzoyl-TN14003 was further studied using multiple myeloma (MM) cells. The inventors found that MM cells are the most affected human blood cancer tested. The CXCR4 antagonist 4F-benzoyl-TN14003 (0.4-40 μM), but not AMD-3100 or CXCL12, inhibited the growth and stimulated apoptotic cell death (measured by annexin assay) of RPMI8226, ARH77, U266, and NCI human MM cells (FIGS. 7A, 7B, 7C, 7D, 7E and 7F, respectively).

Figure 8A:
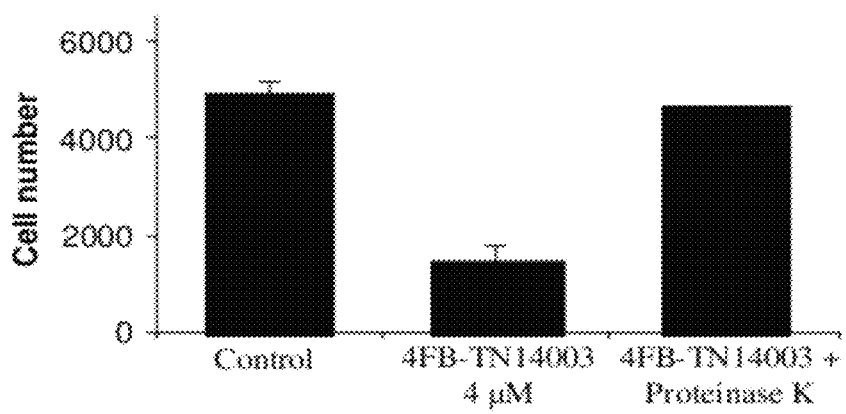
FIG. 8A, inhibition of the effect of 4F-benzoyl-TN14003 on proliferation of human RPMI8226 following treatment of the peptide with Proteinease K.
Figure 8B:
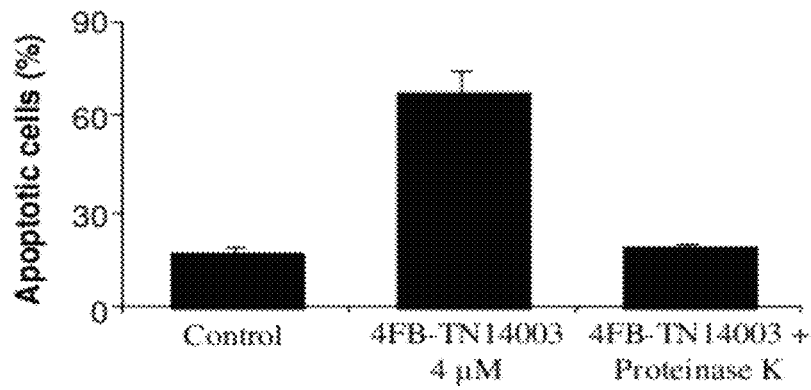
FIG. 8B, inhibition of the effect of 4F-benzoyl-TN14003 on apoptosis of human RPMI8226 following treatment of the peptide with Proteinease K.
Figure 8C:
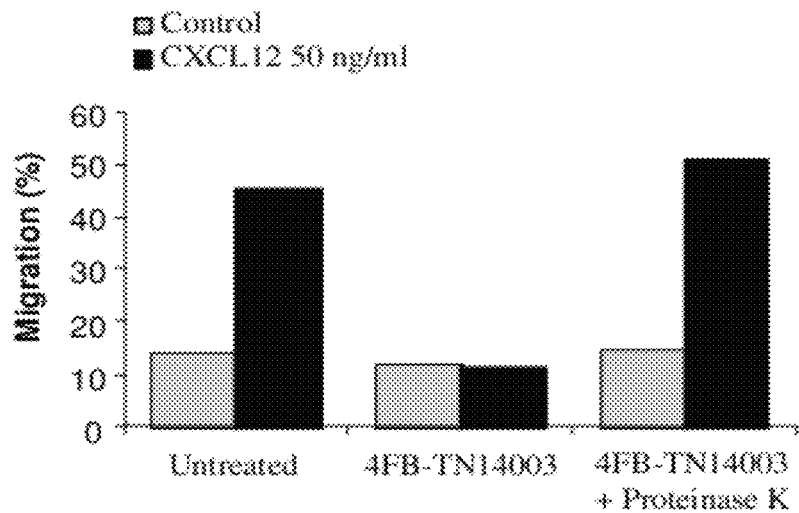
FIG. 8C, inhibition of the inhibitory effect of 4F-benzoyl-TN14003 on migration of Jurkat cells in response to CXCL12 following treatment of the peptide with Proteinease K.

To verify that the effect of 4F-benzoyl-TN14003 is due to the intact peptide, the peptide was incubated with proteinease K and the effect of treated peptide on the survival of human RPMI8226 MM cells (FIGS. 8A and 8B) and the migration of Human Jurkat cells in response to CXCL12 (50 ng/ml, black columns; FIG. 8C) was tested. As can be seen in FIG. 8, treatment of 4F-benzoyl-TN14003 with proteineuse K abolished the activity of the peptide.

Figure 9A:
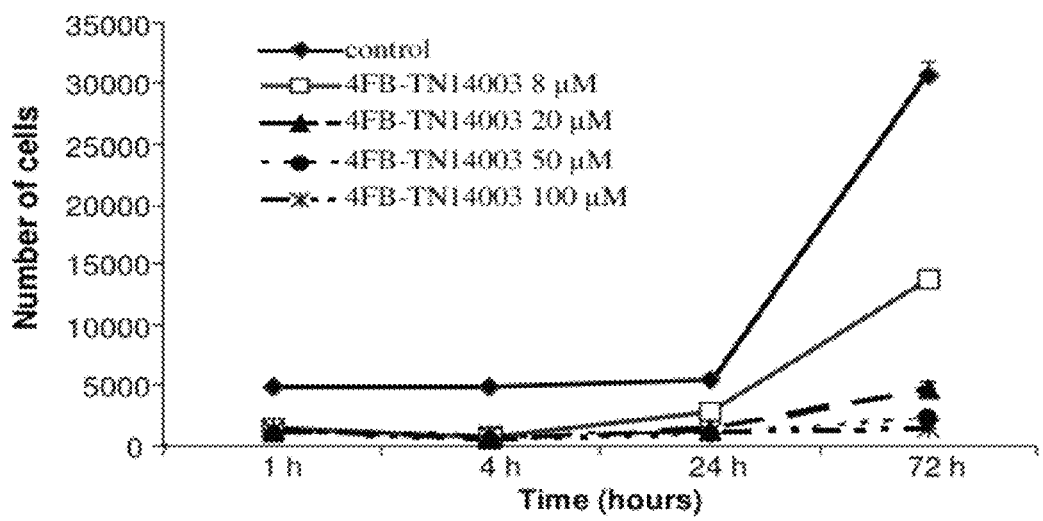
FIG. 9A, the effect of 4F-benzoyl-TN14003 on the number of cells.
Figure 9B:
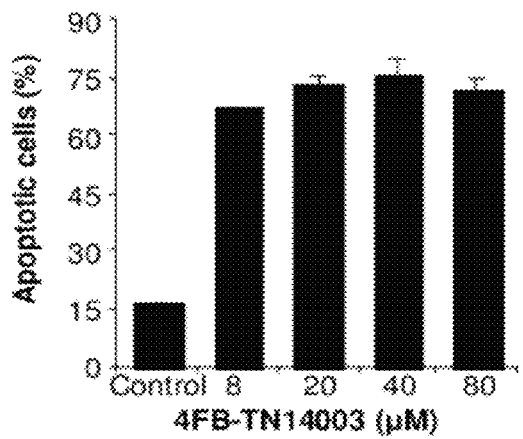
FIG. 9B, the number of apoptotic cells after 1 h of incubation with the peptide.
Figure 9C:
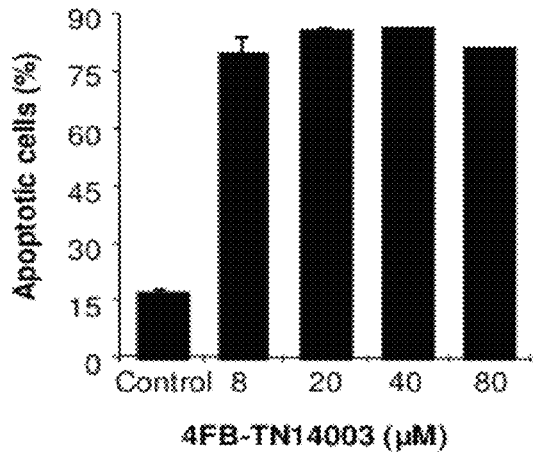
FIG. 9C, the number of apoptotic cells after 4 h.
Figure 9D:
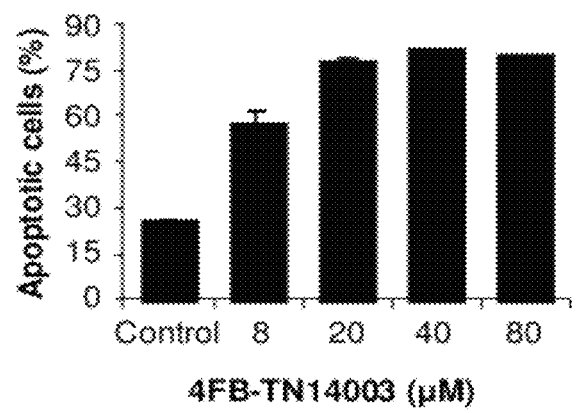
FIG. 9D, the number of apoptotic cells after 24 h.
Figure 9E:
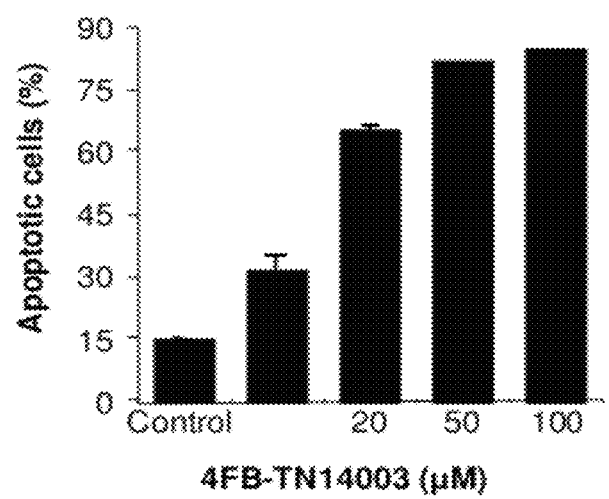
FIG. 9E, the number of apoptotic cells after 72 h.

To further test the effect of 4F-benzoyl-TN14003 on the proliferation and survival of RPMI8226MM cells, the cells were incubated in 10% FCS for 72 hr with different concentrations of 4F-benzoyl-TN14003. Under these conditions, 4F-benzoyl-TN14003 demonstrated a rapid and sustained anti-proliferative (FIG. 9A) death-induced (FIGS. 9B-9E 1-72 hr) effect on RPMI8226MM cells. In FIG. 9A, diamonds indicate control cells (incubated without 4F-benzoyl-TN14003); squares indicate cells incubated with 8 μM of the peptide; triangles indicate cells incubated with 20 μM of the peptide; circles indicate cells incubated with 50 μM of the peptide; and crosses indicate cells incubated with 100 μM of the peptide.

Figure 10A:
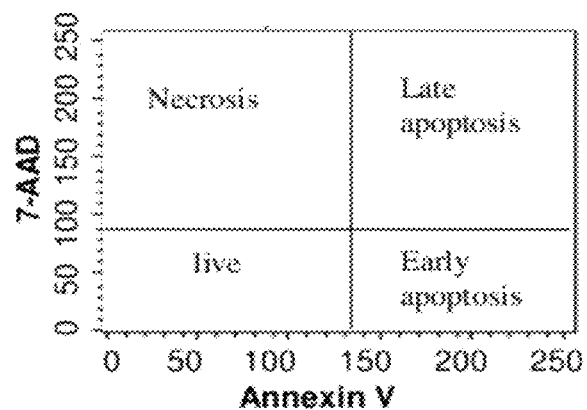
FIG. 10A indicates the different stages of apoptosis and necrosis.
Figure 10B:
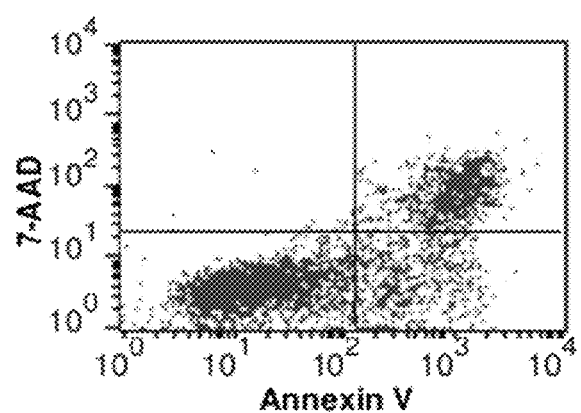
FIG. 10B shows untreated cells.
Figure 10C:
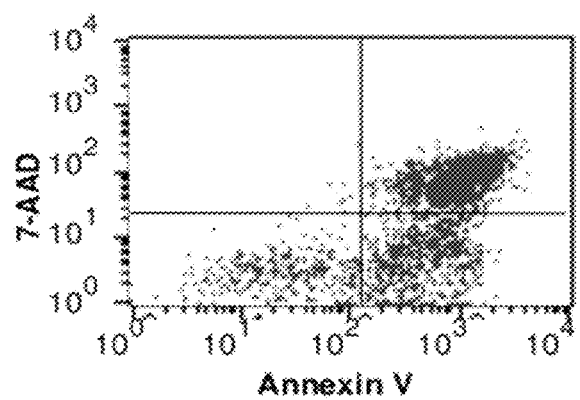
FIG. 10C shows RPMI8226 cells undergoing cell death in response to 4F-benzoyl-TN14003 (8 μM).

The effect of 4F-benzoyl-TN14003 on the proliferation and survival of RPMI8226MM cells may be mediated through induction of apoptotic cell death. Staining of RPMI8226 cells with 7AAD and annexin shows a clear increase in the population of cells that are $annexin^+7AAD^-$ (FIG. 10C) early apoptotic cells as well as $annexin^+7AAD^+$ late apoptotic death cells (FIG. 10C). FIG. 10A illustrates that live cells appear at the bottom left region of the plot, necrotic cells appear at the top left region, late apoptotic cells appear at the top right region and early apoptotic cells appear at the bottom right region.

Example 3

Figure 11A:
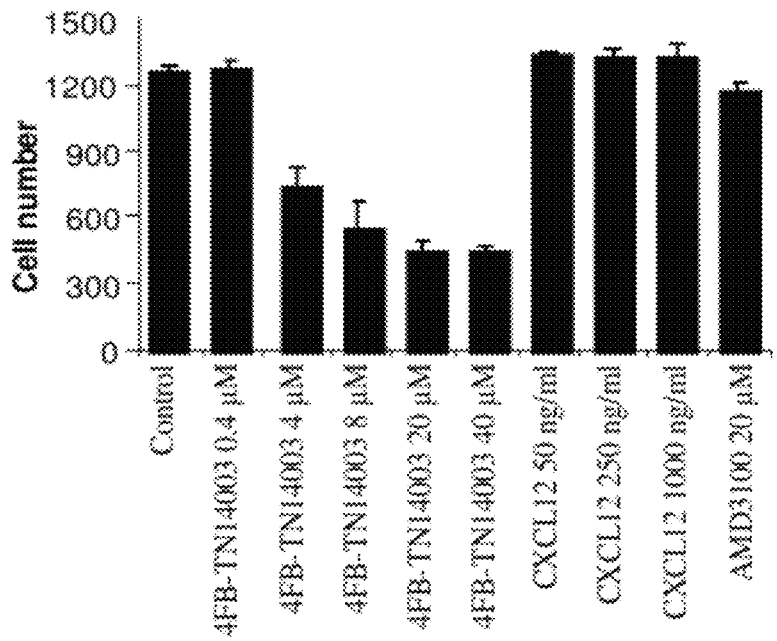
Figure 11B:
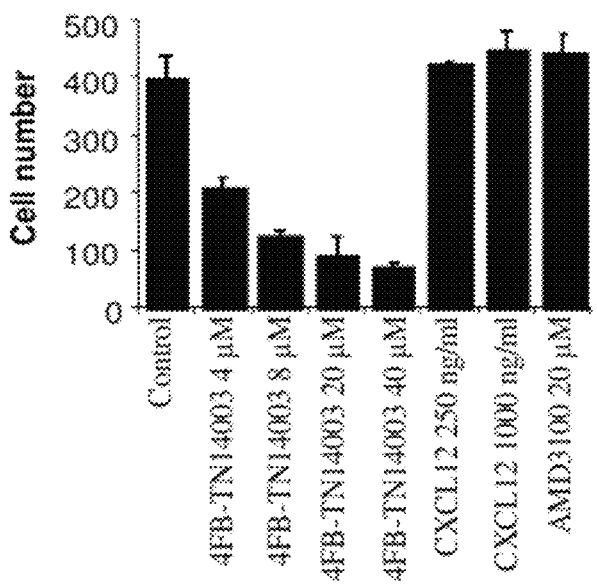
Figure 11C:
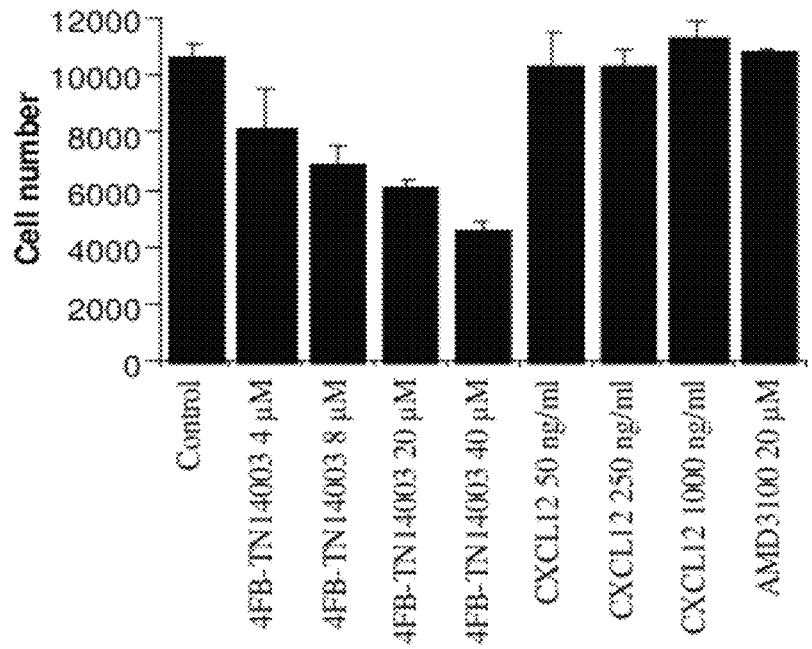
Figure 11D:
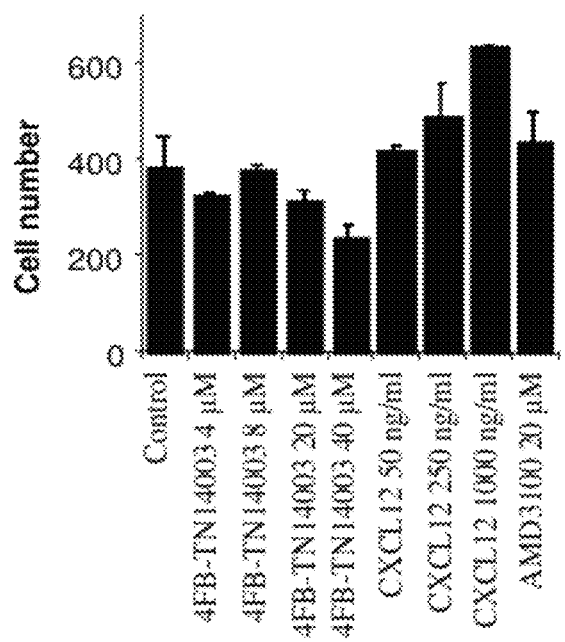

4F-Benzoyl-TN14003 Selectively and Rapidly Stimulates BM-Derived MM Cell Death Based on the previous results, the effect of 4F-benzoyl-TN14003 on the proliferation and survival of freshly isolated bone marrow cells of patients with multiple myeloma (MM) was studied. Bone marrow (BM) derived samples that have high percentage of MM were sensitive to treatment with 4F-benzoyl-TN14003 (FIG. 11A-11C); however, normal BM samples or BM samples with low percentage of MM cells were not sensitive to treatment with 4F-benzoyl-TN14003 (FIG. 11D).

Figure 12A:
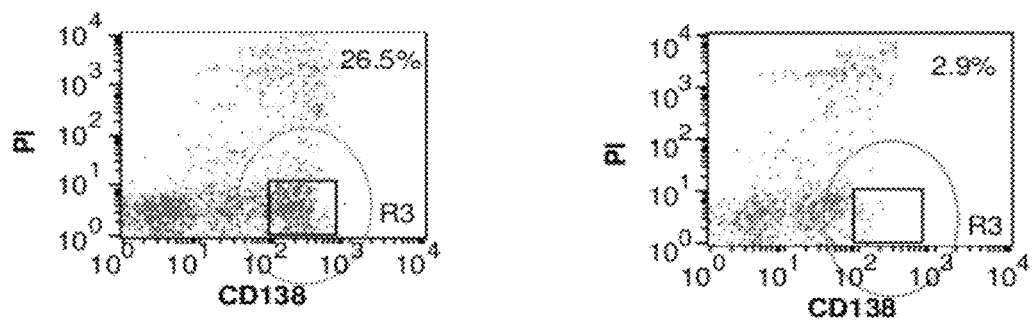
FIG. 12A, the effect of 4F-benzoyl-TN14003 on the survival of BM derived CD138+ cells (R3).
Figure 12B:
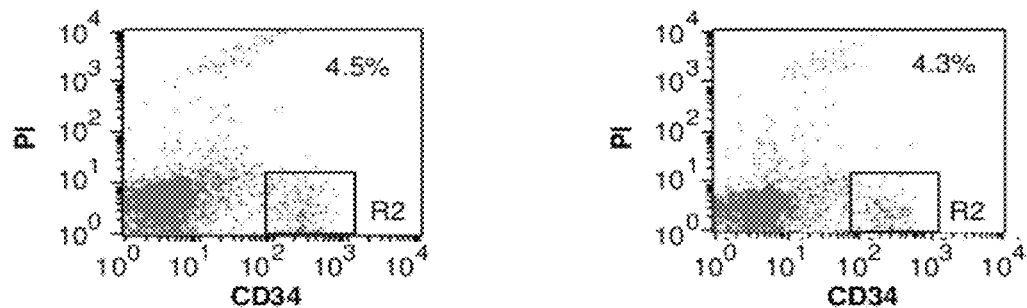
FIG. 12B, the effect of 4F-benzoyl-TN14003 on the survival of BM derived CD34+ cells (R2). Left panels, untreated cells; right panels, 4F-benzoyl-TN14003-treated cells.

Incubation of BM cells from MM patients with 8 µM of 4F-benzoyl-TN14003 for 24 hr induced apoptosis of CD138$^+$ MM cells (FIG. 12A, R3) whereas the percentage of CD34$^+$ cells in these samples remained unaffected (FIG. 12B, R2).

Example 4

4F-benzoyl-TN14003 Synergized with Rapamycin to Induce MM and Glioma Cell Death One candidate target molecule for anti-tumor therapy is represented by the phosphoprotein mammalian target of rapamycin, mTOR (also known as FRAP [FKBP12-rapamycin-associated protein], RAFT [rapamycin and FKBP-12 target], or RAPT), in which the PI3-K/Akt pathway has been suggested to affect the mTOR phosphorylation state and catalytic activity. Rapamycin binds to its cellular receptor, the immunophilin FK506 binding protein 12 (FKBP12), to form a complex that interacts with mTOR, thereby blocking its activity. Mitogen-activated signaling through mTOR phosphorylates the serine/threonine kinase p70S6K and the translational repressor eukaryotic initiation factor (eIF) 4E binding protein (4EBP1) also known as PHAS-I. Activated p70S6K directly phosphorylates the 40S ribosomal protein S6, which correlates with enhanced translation of transcripts with 5-terminal oligo-pyrimidine sequences that encode components of the translational machinery. Multi-site phosphorylation of 4EBP1 results in its dissociation from eIF4E, thereby allowing eIF4E to participate in assembly of a translational initiation complex leading to translational up-regulation of proteins required for cell cycle progression from G1 to S phase. Currently, rapamycin derivatives such as CCI-779, are in clinical testing for MM (Phase II). Recently, it was shown that rapamycin can sensitize MM cell lines as well as primary MM cells to dexamethasone-induced apoptosis, an effect being associated with a concomitant down-regulation of cyclin D2 and the key anti-apoptotic protein survivin.

Figure 13:
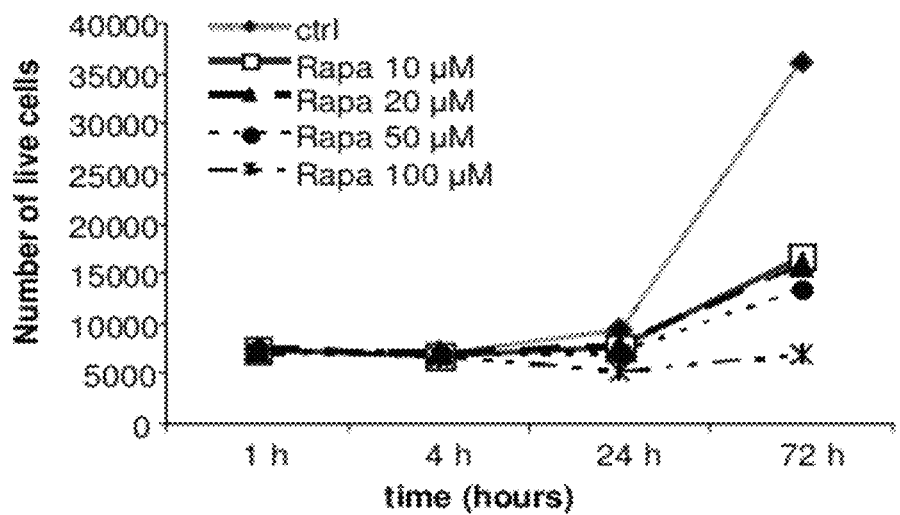
FIG. 13 presents the effect of Rapamycin on the proliferation and survival of RPMI8226MM cells. Diamonds represent untreated cells ("ctrl"); squares represent cells treated with 10 μM rapamycin ("Rapa 10 μM"); triangles represent cells treated with 20 μM rapamycin; circles represent cells treated with 50 μM rapamycin; and crosses represent cells treated with 1000 μM rapamycin.

Rapamycin at concentration of 10-100 µM can induce cell cycle arrest of RPMI8226MM cells. However, it can poorly induce apoptotic cell death of these cells (FIG. 13).

Figure 14:
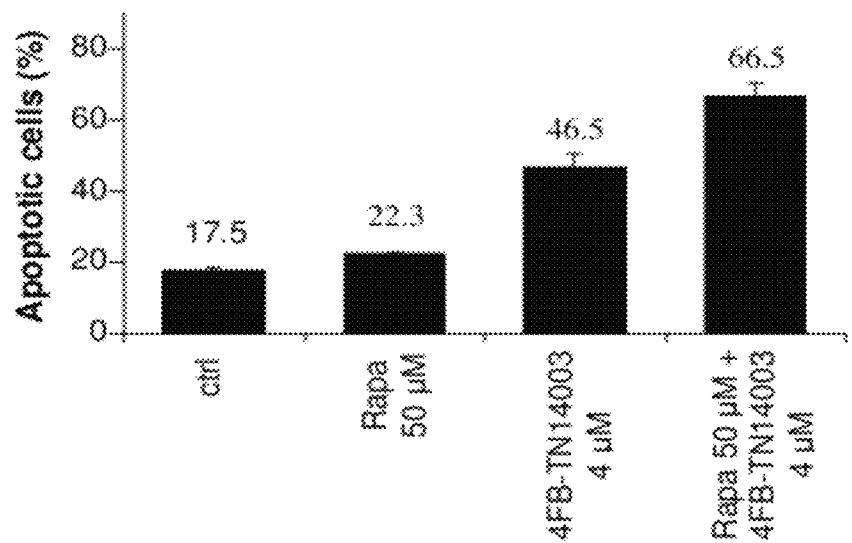
FIG. 14 depicts the effect of rapamycin in combination with 4F-benzoyl-TN14003 on the proliferation and survival of RPMI8226MM cells.

Herein, it was tested whether rapamycin can sensitize MM cell lines to 4F-benzoyl-TN14003-induced apoptosis. In a concentration of 50 rapamycin ("Rapa") stimulated 4.8% cell death over control (22.3% compared to 17.5%). In contrast to rapamycin, 4F-benzoyl-TN14003 induced 28.9% cell death over control. When both agents were used in combination, they synergized to induce 48.9% cell death over control (FIG. 14).

Figure 15A:
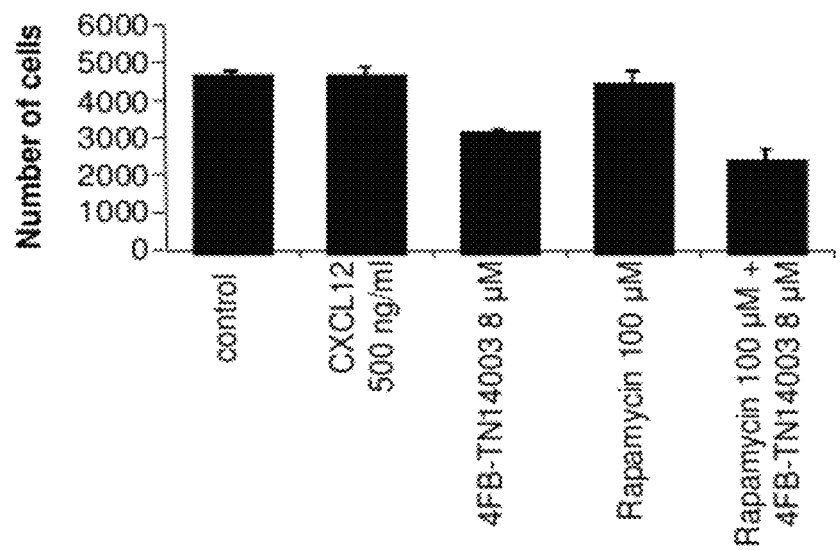
FIG. 15A, the effect of 4F-benzoyl-TN14003 on cell survival.
Figure 15B:
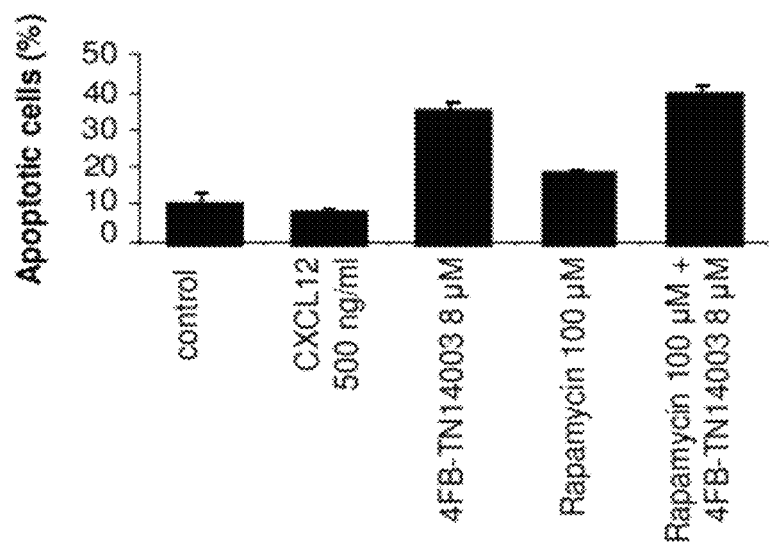
FIG. 15B, the effect of 4F-benzoyl-TN14003 on cell death.

The ability of 4F-benzoyl-TN14003 to induce tumor cell death was also demonstrated for glioma cells. U87 cells were treated with 4F-benzoyl-TN14003 and tested for their survival (FIG. 15A) and death (FIG. 15B). The results indicate that 4F-benzoyl-TN14003 synergizes with rapamycin to induce apoptosis in U87 cells (measured by an Annexin V assay).

Example 5

Animal Pharmacology Studies—4F-Benzoyl-TN14003 Demonstrates an In Vivo Anti-Tumor Effect Against Human NB4 Leukemic Cells in a Xenograft Model In a number of in-vivo studies, 4F-benzoyl-TN14003 was found to demonstrate in vivo anti-tumor effects against human NB4 and K562 leukemic cells in a xenograft model as detailed herein.

Figure 16:
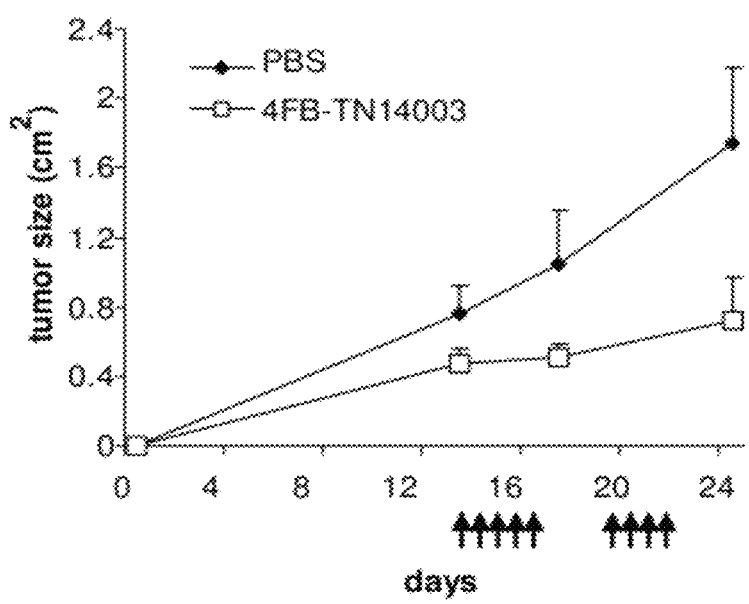
FIG. 16 shows the effect of i.p. injection of 4F-benzoyl-TN14003 (8 mg/Kg) on NB4 derived tumor growth.

Acute promyelocytic leukemia (APL)-derived NB4 cell is extensively used as an in vitro and in vivo model system for studying human leukemia. To investigate the therapeutic anti-tumor potential of the CXCR4 antagonist 4F-benzoyl-TN14003 against human leukemic cells, $10 \times 10^6$ NB4 cells were injected subcutaneously (s.c) into immunodeficient nude mice (n=5). After 14 days, tumors were established at the size of 0.4 cm$^2$, and mice were divided into 4F-benzoyl-TN14003-treated (8 mg/Kg, open squares) and PBS-treated (control, full diamonds) groups. The 4F-benzoyl-TN14003 drug solution was administered intraperitoneal (i.p) each day for 5 days, followed by 2 days without drug, and then 4 additional daily injections (total of 9 injections, FIG. 16). As can be seen in FIG. 16, in mice that were treated with 4F-benzoyl-TN14003, tumor growth was arrested.

Figure 17A:
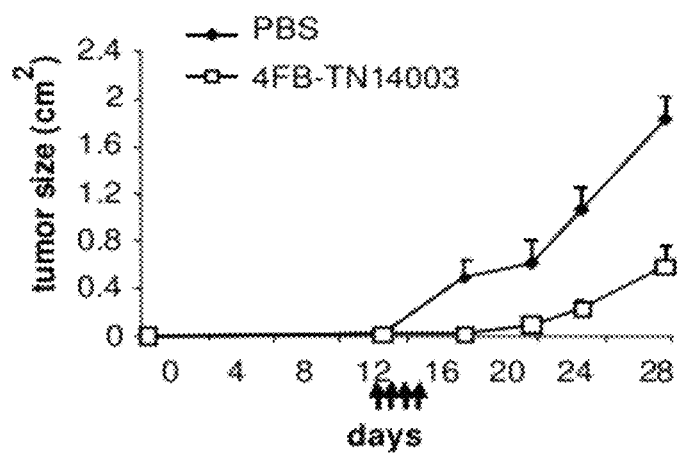
FIG. 17A, effect on tumor size.

To further test the effect of 4F-benzoyl-TN14003 against human leukemic cells, $5 \times 10^6$ NB4 cells were injected subcutaneously (s.c) into immunodeficient nude mice (n=5). After 14 days, tumors were very small, at the size of 0.02 cm$^2$, and mice were divided into 4F-benzoyl-TN14003-treated (open squares) and PBS-treated (control, full diamonds) groups. The 4F-benzoyl-TN14003 drug solution was administered subcutaneously (8 mg/Kg) each day for 4 days (total of 4 injections, FIG. 17A). On day 20, all control mice developed tumors (0.49±0.1 cm$^2$), whereas in the treated mouse group, only 1 mouse developed a small tumor.

Figure 17B:
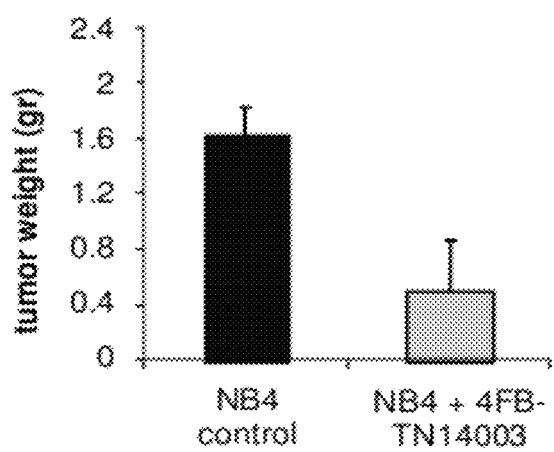
FIG. 17B, effect on tumor weight.

On day 31, all control mice developed big tumors in size (FIG. 17A) and weight (FIG. 17B), whereas in the treated group, 4/5 mice developed smaller tumors in size and weight.

These results suggest potential therapeutic anti-leukemic use of 4F-benzoyl-TN 14003.

Example 6

4F-Benzoyl-TN14003 Demonstrates an In Vivo Anti-Tumor Effect Against Human K562 Leukemic Cells in a Xenograft Model To further investigate the use of 4F-benzoyl-TN14003 in CML tumor development in vivo, an animal model for CML was established in NOD/SCID mice. The NOD/SCID mice model is a powerful predictor of the clinical course of leukemia and can provide a good model system to explore the feasibility of different therapeutic programs. This model enables monitoring the progression and localization of leukemic cells in vivo so that a small number of tumor cells could be detected and the patterns of growth and distribution be studied over time. Current animal models of human leukemic diseases require injection of a large number of target cells. In addition to that, monitoring therapeutic drugs (i.e. STI571) over time on the same animal has not been possible and it usually requires the unnecessary sacrifice of a large number of animals for each experiment. Monitoring leukemic tumor growth, metastases, and response to therapeutic interventions in animal models of minimal disease states is critical for the development of effective strategies that target small numbers of leukemic cells, thus avoiding minimal residual disease.

Figure 18A:
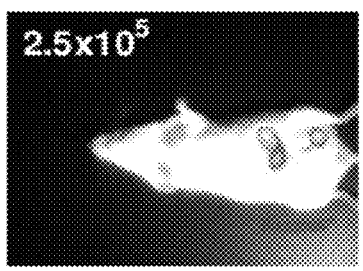
FIG. 18A, $2.5 \times 10^5$ injected cells.
Figure 18B:
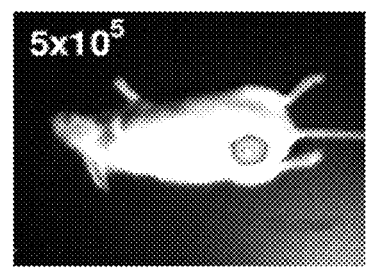
FIG. 18B, $5 \times 10^5$ injected cells.
Figure 18C:
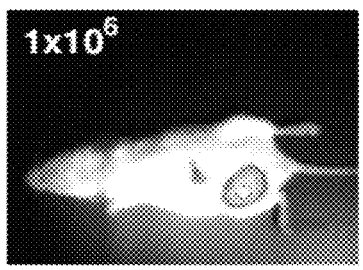
FIG. 18C, $10^6$ injected cells.
Figure 18D:
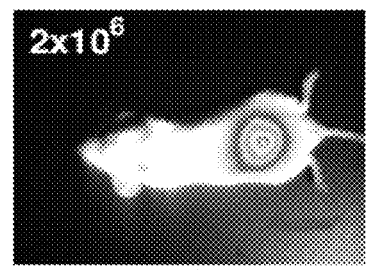
FIG. 18D, $2 \times 10^6$ injected cells.

Herein, a novel in vivo model system is presented, which is noninvasive, direct, and facilitates sensitive quantification of the distribution of leukemic cells in a live animal. In order to monitor the progression and localization of leukemic cells in vivo, the human CML tumor cell lines K562 (K562L) was stably transduced with a retrovirus carrying the luciferase gene. This cell line was injected IP into NOD/SCID mice ($2.5 \times 10^5$, $5 \times 10^5$, $10^6$, $2 \times 10^6$ per mouse; FIGS. 18 A-D, respectively) that were pretreated with a sub-lethal dose of radiation in order to diminish any natural killer cell activity and enhance acceptance of the tumor cells. Twenty-four hr after injection of the cells, the light generated internally by the luciferase expressed in the tumor cells and then transmitted through the animal's tissues was monitored externally using a cooled charge-coupled device camera (CCCD). The substrate luciferin was provided exogenously via IP injection. As few as $2.5 \times 10^5$ leukemic tumor cells distributed throughout the peritoneal cavity were detectable externally (FIG. 18A). Quantitation was achieved by integrating the signal intensity using the Metaview software. The integrated light detected from the animals was proportional to the number of cells injected IP (FIG. 18).

Figure 19:
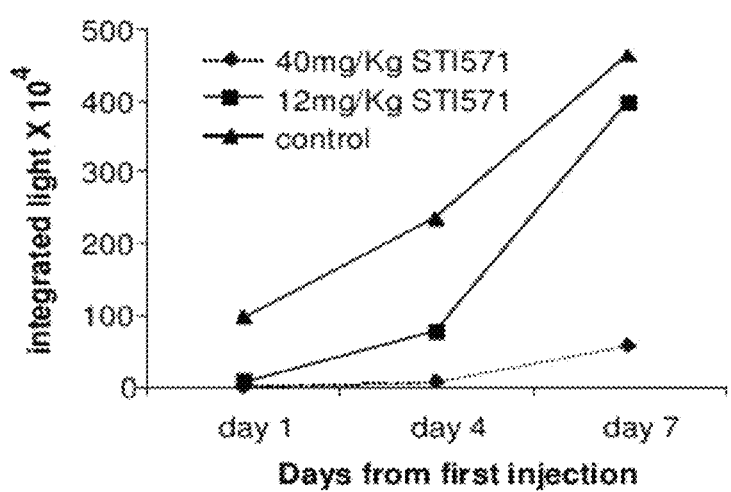
FIG. 19 demonstrates that STI571 inhibits tumor development of K562L in vivo over time. STI571 (12 mg/Kg, or 40 mg/Kg per mouse), which inhibits selectively the tyrosine-kinase activity of c-abl, was injected together with K562L cells ($2 \times 10^6$/mice). Mice were further treated with STI571 on days 3, and 5 following injection of the cells and the amount of light emission was evaluated using the CCCD camera on Days 1, 4 and 7 after cell injection.
Figure 20A:
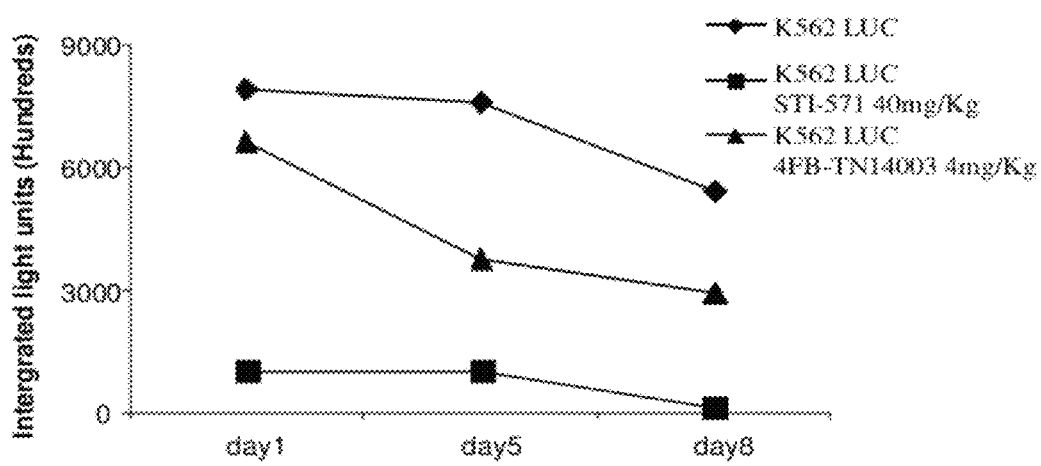
FIG. 20 demonstrates that STI571 and 4F-benzoyl-TN14003 inhibit tumor development of K562L cells in vivo. STI571 (40 mg/Kg) and 4F-benzoyl-TN14003 (4 mg/Kg), were injected IP with K562L cells. The development of tumors was evaluated 24 hr later using the CCCD camera. Mice were further treated with STI571 and 4F-benzoyl-TN14003 on days 3 and 5 and the amount of light they emitted was evaluated using the CCCD camera on days 5 and 8 after injection of the cells.
Figure 20B:
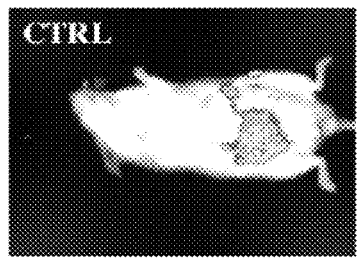
Figure 20C:
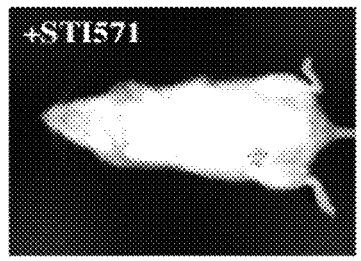
Figure 20D:
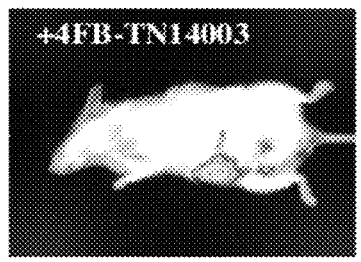

Two therapeutic approaches were studied using this model. The drug therapy for CML, STI571 (Gleevec® provided by Novartis), a synthetic pyrimidine derivative, which inhibits selectively the tyrosine-kinase activity of c-abl and BCR-ABL, was explored in this model system. In addition, the effect of 4F-benzoyl-TN14003 on the growth of cells in vivo was investigated. As demonstrated in FIG. 19, STI571 at 40 mg/Kg (diamonds) stimulated a significant reduction in signal intensities in the treated groups over time.

Further, the effect of 4F-benzoyl-TN14003 on K562L tumor development was studied. 4F-benzoyl-TN14003 was injected i.p into NOD/SCID mice in the amount of 4 mg/Kg per mouse/per injection. The first injection of 4F-benzoyl-TN14003 was given immediately after the injection of K562-luc cells in an opposite route of injection on the peritoneum. Further injections of 4F-benzoyl-TN14003 were given every three days. Mice were monitored under the CCCD camera, 24 hr after each injection at serial time points, every three days. As can be seen in FIG. 20, a 50% inhibition in K562L tumor development over time was detected.

Figure 21:
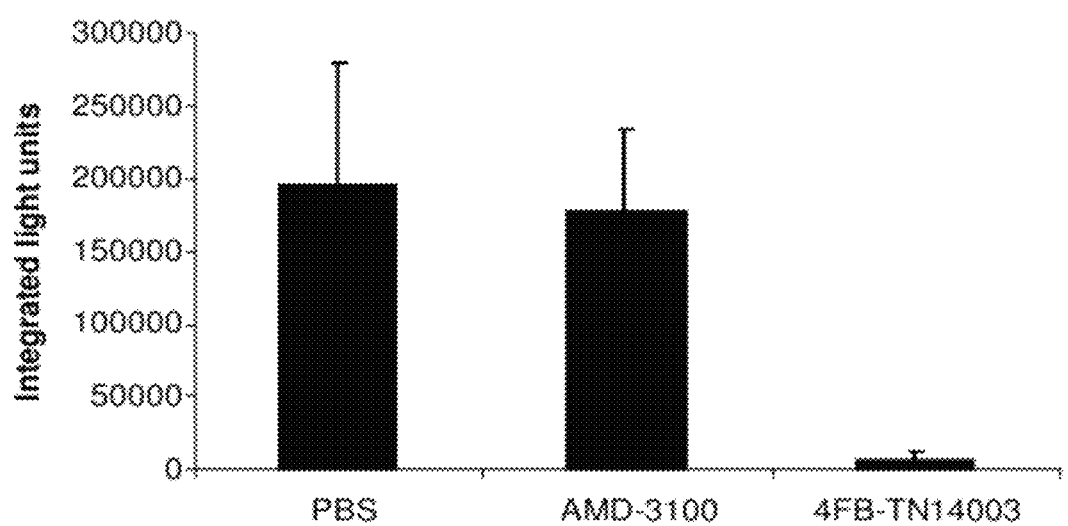
FIG. 21 shows that 4F-benzoyl-TN14003 inhibits tumor development of K562L cells in vivo. 4F-benzoyl-TN14003 (2 mg/Kg) and AMD-3100 (4 mg/Kg) were injected i.p on days 2, 5, 7, 11 following injection of K562L cells. The development of tumors was evaluated on day 17 using the CCCD camera.

To further support the potential use of 4F-benzoyl-TN14003 in treating K562 CM cells in vivo, an additional experiment comparing its activity to the CXCR4 inhibitor AMD-3100 was performed. 4F-benzoyl-TN14003 was injected i.p into NOD/SCID mice in the amount of 2 mg/Kg whereas AMD-3100 was injected 4 mg/Kg per mouse/per injection. The first injection was given 2 days after the injection of K562-luc cells. Further injections were given on days 5, 7 and 11. Mice (n=3) were monitored under the CCCD camera on day 17 after injection of cells. As can be seen in FIG. 21, a >90% inhibition in K562L tumor development over time was measured upon 4F-benzoyl-TN14003 treatment, but not when AMD-3100 was administered.

Example 7

Figure 22A:
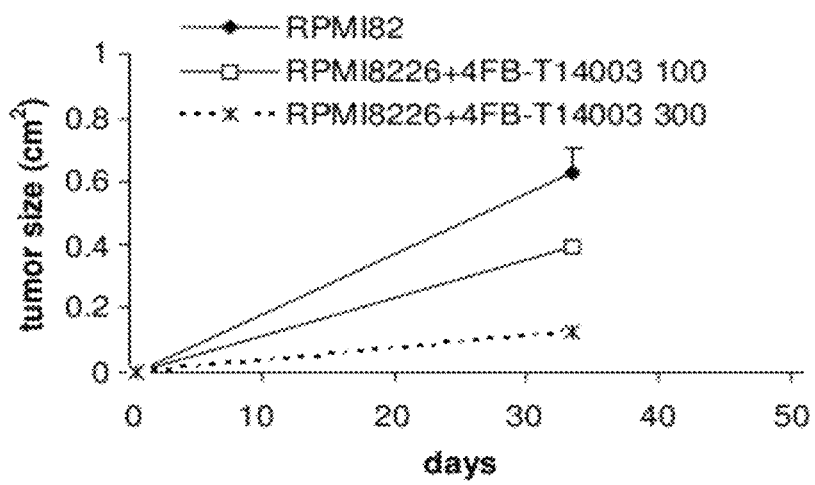
FIG. 22A, reduction of RPMI8226 tumor size upon s.c. administration of 4F-benzoyl-TN14003.

4F-Benzoyl-TN14003 Demonstrates In Vivo Anti-Tumor Effect Against Human of RPMI8226 Cells MM Cells in a Xenograft Model RPMI8226 MM cells are used as an in vitro and in vivo model system for studying human MM. To investigate the therapeutic anti-tumor potential of 4F-benzoyl-TN14003 against human MM cells, $5 \times 10^6$ NB4 cells were injected subcutaneously (s.c) into immunodeficient SCID/Bz mice (n=8 for each group, p<0.05). Tumors were treated S.C. with two concentration of 4F-benzoyl-TN14003 (100 or 300 microgram/mouse) for 21 days. The 4F-benzoyl-TN14003 drug solution was administered SC each day for 21 days, followed by 14 days without drug. After 35 days, tumors in the control group were established at the size of 0.7 cm$^2$, and in the treated mice tumors were reduced (FIG. 22A). In FIG. 22A, diamonds represent RPMI8226 tumors from untreated mice, squares represent RPMI8226 tumors from mice treated with 100 μg of 4F-benzoyl-TN14003, and crosses represent RPMI8226 tumors from mice treated with 300 μg of 4F-benzoyl-TN14003.

Figure 22B:
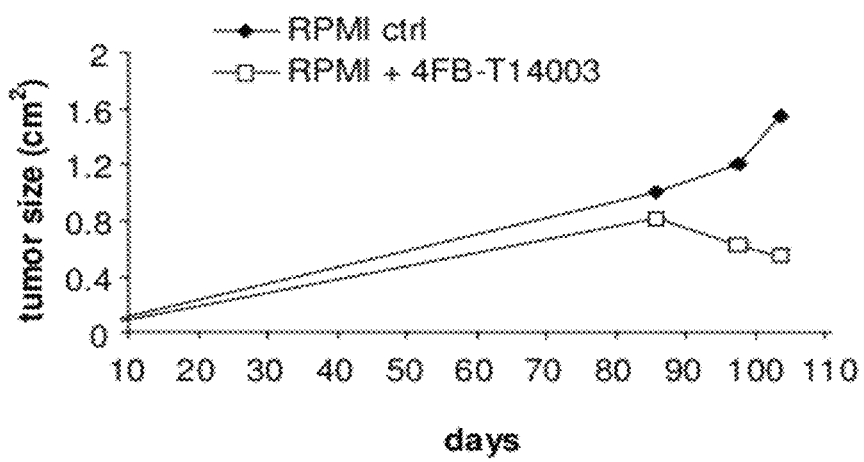
FIG. 22B, reduction of tumor size in established RPMI8226 tumors upon s.c. administration of 4F-benzoyl-TN14003.

To further test the effect of 4F-benzoyl-TN14003 on human MM tumors in vivo, established tumors having a similar size were treated for 7 days with 300 microgram/mouse of 4F-benzoyl-TN14003. As can be seen in FIG. 22B, treatment with 4F-benzoyl-TN14003 stimulated the reduction of the tumor size (n=1). In FIG. 22B, diamonds represent tumors from untreated mice, and squares represent RPMI8226 tumors from mice treated with 4F-benzoyl-TN14003.

Figure 23:
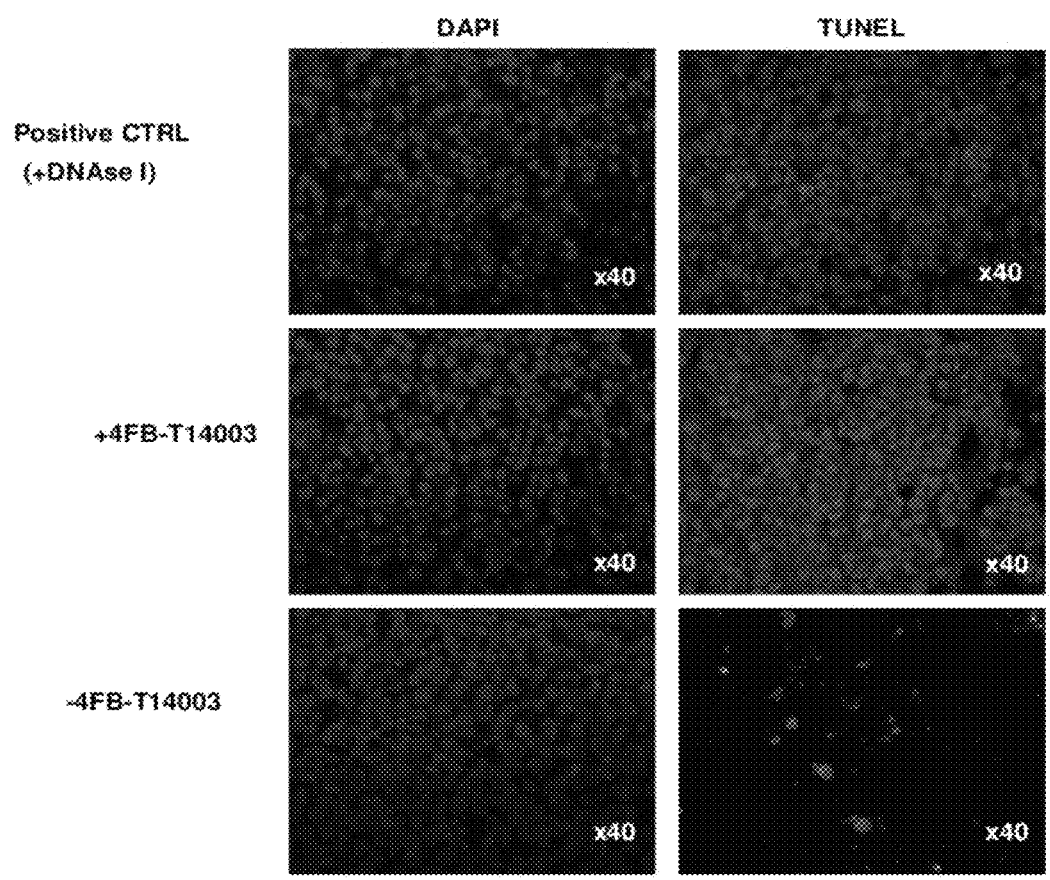
FIG. 23 demonstrates that 4F-benzoyl-TN14003 stimulates apoptotic MM cell death in vivo.

The effect of 4F-benzoyl-TN 14003 on tumor cells in vivo was further tested by injection of 4F-benzoyl-TN14003 (300 microgram/mouse) and 24 hr later collecting the tumors and staining for apoptosis using the TUNEL assay. Clear massive apoptosis induced by 4F-benzoyl-TN14003 is seen in FIG. 23. In FIG. 23, top left and top right panels, respectively, depict DAPI staining or TUNEL staining of a positive control sample (treated with DNAse I); middle left and middle right panels, respectively, depict DAPI staining or TUNEL staining of a sample obtained from 4F-benzoyl-TN14003 treated mice; and bottom left and bottom right panels, respectively, depict DAPI staining or TUNEL staining of a sample obtained from control mice (not treated with 4F-benzoyl-TN14003).

REFERENCES

Avniel, S. et al., *J. Invest. Dermatol.* 2006, 126(2): 468-76.
Balkwill, F. *Semi. in Canc. Biol.* 2004, 14: 171-179.
Broxmeyer, H. E. et al., *J. Exp. Med.* 2005, 201(8): 1307-1318.
Dar, A. et al., *Nat. Immunol.* 2005. 6(10): 1038-1046.
Flomenberg, N. et al., *Blood,* 2005, 106(5): 1867-1874.
Kim, C. H. and Broxmeyer H. E., *Blood,* 1998, 91(1): 100-110.
Kollet, O. et al., *Blood,* 2002, 100(8): 2778-2786.
Lack, N. A. et al., *Clin. Pharmacol. Ther.* 2005, 77(5): 427-436.
Lapidot, T. and Kollet, O., *Leukemia,* 2002 16(10): 1992-2003.
Lapidot, T. et al., *Blood,* 2005, 106(6): 1901-1910.
Levesque, J. P. et al., *J. Clin. Invest.* 2003, 111(2): 187-196.
Martin, C. et al., *Immunity,* 2003, 19(4): 583-593.
Muller, A. et al., *Nature,* 2001, 410: 50-56.
Nagasawa, T. et al., *Proc. Nat. Aca. Sci.* 1994, 91: 2305-2309.
Peled, A., et al., *Science,* 1999, 283(5403): 845-848.
Phillips, R. et al., *Amer. J. Respir. Critic. Care Med.* 2003, 167: 1676-1686.
Princen, K. and Schols, D., *Cytokine Grow. Fac. Rev.* 2005, 16(6): 659-677.
Rossi, D. and Zlotnik, A., *Ann. Rev. Immun.* 2000, 18: 217-242.

Tamamura, H. et al., *Biochem. Biophys. Res. Commun.* 1998, 253(3): 877-882.
Tamamura, H. et al., *Org. Biomol. Chem.* 2003, 1: 3663-3669.
Tamamura, H. and Fujii, N., *Expert Opin. Ther. Targets*, 2005, 9(6): 1267-1282.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating lymphoma in a subject, comprising administering to the subject a therapeutically effective amount of an anti-CD20 antibody and a peptide having an amino acid sequence as set forth in SEQ ID NO:1, thereby treating the lymphoma.

2. The method of claim 1, wherein said anti-CD20 antibody comprises rituximab.

3. A method for inducing lymphoma cell death in a subject in need thereof, comprising administering to the subject a therapeutically effective amount of an anti-CD20 antibody and a peptide having an amino acid sequence as set forth in SEQ ID NO:1, thereby inducing lymphoma cell death.

4. The method of claim 3, wherein said anti-CD20 antibody comprises rituximab.

5. A method for increasing the sensitivity of lymphoma cells to an anti-CD20 antibody, comprising administering to a subject in need thereof a sensitizing-effective amount of a peptide having an amino acid sequence as set forth in SEQ ID NO:1 in concurrent or sequential combination with the anti-CD20 antibody, thereby increasing the sensitivity of lymphoma cells to the anti-CD20 antibody.

6. The method of claim 5, wherein said anti-CD20 antibody comprises rituximab.

* * * * *